United States Patent [19]

Bang et al.

[11] Patent Number: 4,775,624

[45] Date of Patent: Oct. 4, 1988

[54] VECTORS AND COMPOUNDS FOR EXPRESSION OF HUMAN PROTEIN C

[75] Inventors: Nils U. Bang; Robert J. Beckmann; S. Richard Jaskunas, all of Indianapolis; Mei-Huei T. Lai, Carmel; Shelia P. Little; George L. Long, both of Indianapolis; Robert F. Santerre, Zionsville, all of Ind.

[73] Assignee: Eli Lilly and Company, Indianapolis, Ind.

[21] Appl. No.: 699,967

[22] Filed: Feb. 8, 1985

[51] Int. Cl.[4] .................. C12N 9/64; C12N 15/00; C12P 21/00; C07H 15/12

[52] U.S. Cl. .................................. 435/226; 435/68; 435/70; 435/172.3; 435/240.25; 435/253; 435/320; 435/832; 435/849; 435/886; 935/14; 935/29; 935/32; 536/27

[58] Field of Search ............... 536/27; 435/68, 70, 435/172.3, 317, 241, 253, 226

[56] References Cited

U.S. PATENT DOCUMENTS 4,382,028 5/1983 Paget .............................. 260/112 R
4,438,032 3/1984 Gold et al. ..................... 260/112 R

OTHER PUBLICATIONS

W. Kisiel, 1979, *J. Clin. Invest.* 64: 761.
J. Stenflo and P. Fernlund, 1982, *J. Biol. Chem.* 257(20): 12170.
J. Stenflo and P. Fernlund, 1982, *J. Biol. Chem.* 257(20): 12180.
J. Gardiner and J. Griffin, 1983, *Progress in Hematology*, XIII: 265.
C. T. Esmon, 1983, *Blood* 62(6): 1155.
D. Foster and E. Davie, 1984, *Proc. Natl. Acad. Sci. U.S.A.* 81: 4766.
Long et al., 1984, *Proc. Natl. Acad. Sci. U.S.A.* 81: 5653.

*Primary Examiner*—Thomas G. Wiseman
*Assistant Examiner*—Thomas D. Mays
*Attorney, Agent, or Firm*—Gerald V. Dahling; Leroy Whitaker

[57] ABSTRACT

The present invention comprises novel DNA compounds which encode human protein C activity. A variety of eukaryotic and prokaryotic recombinant DNA expression vectors have been constructed that comprise the novel protein C activity-encoding DNA and drive expression of protein C activity when transformed into an appropriate host cell. The novel expression vectors can be used to produce protein C derivatives, such as non-carboxylated, non-glycosylated, or non-hydroxylated protein C, and to produce protein C precursors, such as nascent or zymogen protein C, and to produce sub-fragments of protein C, such as active or inactive light and heavy chain. The recombinant-produced protein C activity is useful in the treatment and prevention of a variety of vascular disorders.

82 Claims, 20 Drawing Sheets

Restriction Site and Function Map of Plasmid pHC7
(5945 bp)

Restriction Site and Function Map of
Plasmid pHC7
(5945 bp)**

Restriction Site and Function Map of
Plasmid pSV2-HPC8
(6592 bp)**

Restriction Site and Function Map of Plasmid pL133
(5655 bp)

Restriction Site and Function Map of Plasmid pL132
(7.14 kb)

Restriction Site and Function Map of
Plasmid pL141
(7.6 kb)**

Restriction Site and Function Map of Plasmid pL142
(5.9 kb)**

Restriction Site and Function Map of
Plasmid pMSV-HPC
(13.7 kb)**

Restriction Site and Function Map of Plasmid pMMTdeltaBPV-HPC
(8.3 kb)

Restriction Site and Function Map of
Plasmid pL151
(8.0 kb)

Plasmid 103 (Figure 10)

Hind III
S1 Nuclease
Bam HI Linkers
T₄ DNA Ligase
Bam HI
T₄ DNA Ligase

Eco RI Partial Digestion
S1 Nuclease
Hind III Linkers
T₄ DNA Ligase
Hind III
T₄ DNA Ligase

Figure 12

Plasmid 105 (Figure 11)

↓ Sal I
↓ Bam HI
| Alkaline
↓ Phosphatase

Plasmid pKEN 111 (101 in Figure 10)

↓ Hpa I
| Sal I Linkers
↓ T₄ DNA Ligase
↓ Sal I
↓ Pvu II
| Bam HI Linkers
↓ T₄ DNA Ligase
↓ Bam HI ≈950bp Fragment
Sal I, Bam HI Ends pKEN021

Plasmid 106: Hind III, lpp^p, Xba I, Eco RI, Bam HI, 3'lpp, Sal I, Ap^R

Bam HI
Xba I
Alkaline Phosphatase

Plasmid 107: Hind III, lpp^p, Xba I, Ap^R, Bam HI, Sal I

Plasmid pNM789
(117 in Figure 16)

↓ Pvu II Partial Digestion
↓ Bam HI
↓ Alkaline Phosphatase

Synthetic Fragment

T₄ DNA Ligase

Restriction Site and Function Map of
Plasmid pCZ101
(10.8 kb)**

Restriction Site and Function Map of
Plasmid pCZ10
(8.7 kb)**

Restriction Site and Function Map of
Plasmid pCZ459
(9.9 kb)**

VECTORS AND COMPOUNDS FOR EXPRESSION OF HUMAN PROTEIN C

SUMMARY OF THE INVENTION

The present invention provides novel DNA compounds and recombinant DNA cloning vectors that encode human protein C activity. The vectors allow expression of the novel DNA compounds in either eukaryotic or prokaryotic host cells. The present invention also provides host cells transformed with these novel cloning vectors. The transformed host cells express human protein C or precursors, derivatives, or subfragments thereof. Many of the present DNA compounds can be used to produce protein C derivatives never before synthesized either in nature or in the laboratory, and the present invention also comprises these unique proteins.

Protein C, a vitamin K dependent protein of blood plasma, is a protein of major physiological importance. In consort with other proteins, protein C functions as perhaps the most important down-regulator of blood coagulation resulting in thrombosis. In other words, the protein C enzyme system represents a major physiological mechanism for anticoagulation. The mechanism of action of the activated form of protein C and the mechanism of activation of the inactive zymogen into the active protease have been clarified in recent years (for review, see J. E. Gardiner and J. H. Griffin, *Progress in Hematology*, Vol. XIII, pp. 265–278, ed. Elmer B. Brown, Grune and Stratton, Inc., 1983).

To understand how activated protein C downregulates blood coagulation, the following brief description of the coagulation enzyme system is provided. The coagulation system is best looked at as a chain reaction involving the sequential activation of zymogens into active serine proteases eventually producing the enzyme, thrombin, which through limited proteolysis converts plasma fibrinogen into the insoluble gel, fibrin. Two key events in the coagulation cascade are the conversion of clotting factor X to Xa by clotting factor IXa and the conversion of prothrombin into thrombin by clotting factor Xa. Both of these reactions occur on cell surfaces, most notably the platelet surface, and both reactions require cofactors. The major cofactors, factors V and VIII, in the system circulate as relatively inactive precursors, but when the first few molecules of thrombin are formed, thrombin loops back and activates the cofactors through limited proteolysis. The activated cofactors, Va and VIIIa, accelerate both the conversion of prothrombin into thrombin and also the conversion of factor X to factor Xa by approximately five orders of magnitude. Activated protein C overwhelmingly prefers two plasma protein substrates which it hydrolyzes and irreversibly destroys. These plasma protein substrates are the activated forms of the clotting cofactors, Va and VIIIa. Activated protein C only minimally degrades the inactive precursors, clotting factors V and VIII. Activated protein C in dogs has been shown to sharply increase circulating levels of the major physiological fibrinolytic enzyme, tissue plasminogen activator. Activated protein C has been shown in vitro to enhance the lysis of fibrin in human whole blood, and recent experiments suggest that this effect is mediated through the interaction with a newly discovered inhibitor of tissue plasminogen activator. Therefore, activated protein C may represent an important adjunct in in vivo fibrinolysis in man.

The activation of protein C involves thrombin, the final serine protease in the coagulation cascade, and an endothelial cell membrane-associated glycoprotein called thrombomodulin. Thrombomodulin forms a tight, stoichiometric complex with thrombin. Thrombomodulin, when complexed with thrombin, totally changes the functional properties of thrombin. Thrombin normally clots fibrinogen, activates platelets, and converts clotting cofactors V and VIII to their activated forms, Va and VIIIa. Finally, thrombin acts on protein C to activate it but only very slowly and very inefficiently. In contrast, thrombin complexed with thrombomodulin does not clot fibrinogen, does not activate platelets, and does not convert clotting factors V and VIII to their activated counterparts. Thrombin in complex with thrombomodulin activates protein C, and the rate constant of protein C activation by thrombomodulin-thrombin is some 20,000 fold higher than the rate constant for thrombin alone.

An important cofactor for activated protein C is protein S, another vitamin K-dependent plasma protein, and protein S substantially increases activated protein C-mediated hydrolysis of factors Va and VIIIa.

Activated protein C is a novel antithrombotic agent with a wider therapeutic index than available anticoagulants, such as heparin and the oral hydroxycoumarin type anticoagulants. Neither protein C nor activated protein C is effective until thrombin is generated at some local site. Activated protein C is virtually ineffective without thrombin, because thrombin is needed to convert clotting factors V to Va and VIII to VIIIa; the activated forms of these two cofactors are the preferred substrate for activated protein C. The protein C zymogen, when infused into patients, will remain inactive until thrombin is generated and complexed with thrombomodulin; for without thrombomodulin-thrombin, the protein C zymogen is not converted into its active counterpart. Thus, protein C or activated protein C is an *on-demand* anticoagulant of wide clinical utility for use as an alternative to heparin and the hydroxycoumarins. These conventional anticoagulants, in contrast to protein C, maintain a constant anticoagulant state for as long as they are given to the patient, thereby substantially increasing the risk of bleeding complications over that predicted for protein C or activated protein C.

The biological and potential therapeutic importance of protein C can be deduced from clinical observations. In congenital homozygous protein C deficiency, affected family members die in early childhood from purpura fulminans, an often lethal form of disseminated intravascular coagulation. In heterozygous protein C deficiency, affected members suffer severe, recurrent thromboembolic episodes. It is well established clinically that plasma protein concentrates designed to treat hemophilia B or factor IX deficiency and which contain protein C as an impurity are effective in the prevention and treatment of intravascular clotting in homozygous as well as heterozyous protein C deficiency. Protein C levels have also been noted to be abnormally low in thrombotic states and in disease states predisposing to thrombosis, such as disseminated intravascular coagulation, major trauma, major surgery, and cancer.

Human protein C is a serine protease zymogen present in blood plasma and synthesized in the liver. For expression of complete biological activity, protein C requires a post-translational modification for which vitamin K is needed. The mature, two-chain, disulfide-linked, protein C zymogen arises from a single-chain precursor by limited proteolysis. This limited proteolysis is believed to include cleavage of a signal peptide of ~33 amino acid residues (residues 1-33, below) during secretion of the nascent polypeptide from the liver, removal of a pro peptide of ~9 amino acid residues (residues 34-42), and removal of amino acid resdues 198 and 199 to form the two chains observed in the zymogen. The activation of the zymogen into the active serine protease involves the proteolytic cleavage of an ARG-LEU peptide bond (residues 211 and 212). This latter cleavage releases a dodecapeptide (residues 200-211) constituting the amino-terminus of the larger chain of the two-chain molecule. Protein C is significantly glycosylated; the mature enzyme contains ~23% carbohydrate. Protein C also contains a number of unusual amino acids, including γ-carboxyglutamic acid and β-hydroxyaspartic acid. γ-carboxyglutamic acid (gla) is produced from glutamic residues with the aid of a hepatic microsomal carboxylase which requires vitamin K as a cofactor. Since prokaryotes usually neither glycosylate, γ-carboxylate, nor β-hydroxylate proteins expressed from recombinant genes, the present invention is significant in that it allows for the first time the synthesis of protein C derivatives which have not undergone many of the post-translational modifications of normal human protein C. These unique derivatives have enormous research and clinical value, as discussed more fully below.

For purposes of the present invention, as disclosed and claimed herein, the following terms are as defined below.

ApR—the ampicillin-resistant phenotype or gene conferring same.

ep—a DNA segment comprising the SV40 early promoter of the t-antigen (F) gene, the t-antigen binding sites, and the SV40 origin of replication.

Functional Polypeptide—a recoverable bioactive heterologous or homologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bio-inactivating polypeptide which can be specifically cleaved.

G418R—the G418-resistant phenotype or gene conferring same. May also be identified as KmR.

IVS—DNA encoding an intron, also called an intervening sequence.

MSV LTR—a DNA segment comprising the promoter activity of the Murine Sarcoma virus long terminal repeat.

Nascent protein—the polypeptide produced upon translation of a mRNA transcript, prior to any post-translational modifications.

pA—a DNA sequence encoding a polyadenylation signal.

Promoter—a DNA sequence that directs transcription of DNA into RNA.

Protein C activity—any property of human protein C responsible for biological function or antihuman protein C antibody-binding activity.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which a promoter has been incorporated.

Replicon—A DNA sequence that controls and allows for autonomous replication of a plasmid or other vector.

Restriction Fragment—any linear DNA sequence generated by the action of one or more restriction endonuclease enzymes.

RSV LTR—a DNA segment comprising the promoter activity of the Rous Sarcoma virus long terminal repeat.

Sensitive Host Cell—a host cell grow in the presence of a given antibiotic or other toxic compound without a DNA segment that confers resistance thereto.

Structural Gene—any DNA sequence that encodes a functional polypeptide, inclusive of translational start and stop signals.

TcR—the tetracycline-resistant phenotype or gene conferring same.

Transformation—the introduction of DNA into a recipient host cell that changes the genotype of the recipient cell.

Transformant—a recipient host cell that has undergone transformation.

Translational Activating Sequence—any DNA sequence, inclusive of that encoding a ribosome binding site and translational start codon, such as 5'-ATG-3', that provides for the translation of a mRNA transcript into a peptide or polypeptide.

Zymogen—an enzymatically inactive precursor of a proteolytic enzyme.

DETAILED DESCRIPTION OF THE INVENTION

The present invention comprises novel DNA compounds encoding human protein C activity. Depicting only the coding strand of the molecule for convenience, the novel compounds comprise the sequence:

| | 5'-$R^1{}_N$—$R_M$—GCC | AAC | TCC | TTC | CTG | GAG | GAG | CTC | CGT | CAC | AGC |
|---|---|---|---|---|---|---|---|---|---|---|---|
| AGC | CTG | GAG | CGG | GAG | TGC | ATA | GAG | GAG | ATC | TGT | GAC | TTC | GAG |
| GAG | GCC | AAG | GAA | ATT | TTC | CAA | AAT | GTG | GAT | GAC | ACA | CTG | GCC |
| TTC | TGG | TCC | AAG | CAC | GTC | GAC | GGT | GAC | CAG | TGC | TTG | GTC | TTG |
| CCC | TTG | GAG | CAC | CCG | TGC | GCC | AGC | CTG | TGC | TGC | GGG | CAC | GGC |
| ACG | TGC | ATC | GAC | GGC | ATC | GGC | AGC | TTC | AGC | TGC | GAC | TGC | CGC |
| AGC | GGC | TGG | GAG | GGC | CGC | TTC | TGC | CAG | CGC | GAG | GTG | AGC | TTC |
| CTC | AAT | TGC | TCG | CTG | GAC | AAC | GGC | GGC | TGC | ACG | CAT | TAC | TGC |
| CTA | GAG | GAG | GTG | GGC | TGG | CGG | CGC | TGT | AGC | TGT | GCG | CCT | GGC |
| TAC | AAG | CTG | GGG | GAC | GAC | CTC | CTG | CAG | TGT | CAC | CCC | GCA | GTG |
| AAG | TTC | CCT | TGT | GGG | AGG | CCC | TGG | AAG | CGG | ATG | GAG | AAG | AAG |
| CGC | AGT | CAC | CTG | AAA | CGA | GAC | ACA | GAA | GAC | CAA | GAA | GAC | CAA |
| GTA | GAT | CCG | CGG | CTC | ATT | GAT | GGG | AAG | ATG | ACC | AGG | CGG | GGA |
| GAC | AGC | CCC | TGG | CAG | GTG | GTC | CTG | CTG | GAC | TCA | AAG | AAG | AAG |
| CTG | GCC | TGC | GGG | GCA | GTG | CTC | ATC | CAC | CCC | TCC | TGG | GTG | CTG |

-continued

| | | | | | | | | | | | | |
|---|---|---|---|---|---|---|---|---|---|---|---|---|
| ACA | GCG | GCC | CAC | TGC | ATG | GAT | GAG | TCC | AAG | AAG | CTC | CTT | GTC |
| AGG | CTT | GGA | GAG | TAT | GAC | CTG | CGG | CGC | TGG | GAG | AAG | TGG | GAG |
| CTG | GAC | CTG | GAC | ATC | AAG | GAG | GTC | TTC | GTC | CAC | CCC | AAC | TAC |
| AGC | AAG | AGC | ACC | ACC | GAC | AAT | GAC | ATC | GCA | CTG | CTG | CAC | CTG |
| GCC | CAG | CCC | GCC | ACC | CTC | TCG | CAG | ACC | ATA | GTG | CCC | ATC | TGC |
| CTC | CCG | GAC | AGC | GGC | CTT | GCA | GAG | CGC | GAG | CTC | AAT | CAG | GCC |
| GGC | CAG | GAG | ACC | CTC | GTG | ACG | GGC | TGG | GGC | TAC | CAC | AGC | AGC |
| CGA | GAG | AAG | GAG | GCC | AAG | AGA | AAC | CGC | ACC | TTC | GTC | CTC | AAC |
| TTC | ATC | AAG | ATT | CCC | GTG | GTC | CCG | CAC | AAT | GAG | TGC | AGC | GAG |
| GTC | ATG | AGC | AAC | ATG | GTG | TCT | GAG | AAC | ATG | CTG | TGT | GCG | GGC |
| ATC | CTC | GGG | GAC | CGG | CAG | GAT | GCC | TGC | GAG | GGC | GAC | AGT | GGG |
| GGG | CCC | ATG | GTC | GCC | TCC | TTC | CAC | GGC | ACC | TGG | TTC | CTG | GTG |
| GGC | CTG | GTG | AGC | TGG | GGT | GAG | GGC | TGT | GGG | CTC | CTT | CAC | AAC |
| TAC | GGC | GTT | TAC | ACC | AAA | GTC | AGC | CGC | TAC | CTC | GAC | TGG | ATC |
| CAT | GGG | CAC | ATC | AGA | GAC | AAG | GAA | GCC | CCC | CAG | AAG | AGC | TGG |
| GCA | CCT | TAG—3' | | | | | | | | | | | | wherein
A is deoxyadenyl,
G is deoxyguanyl,
C is deoxycytidyl,
T is thymidyl,
R is 5'-GCC CAC CAG GTG CTG CGG ATC CGC, AAA CGT-3' or 5'-CAC CAG GTG CTG CGG ATC CGC AAA CGT-3'
R¹ is

| | | | | | | | | |
|---|---|---|---|---|---|---|---|---|
| 5'-ATG | TGG | CAG | CTC | ACA | AGC | CTC | CTG | TTC GTG |
| GCC | ACC | TGG | GGA | ATT | TCC | GGC | ACA | CCA GCT CCT |
| CTT | GAC | TCA | GTG | TTC | TCC | AGC | AGC | GAG CGT—3' |
| or 5'-ATG | TGG | CAG | CTC | ACA | AGC | CTC | CTG | TTC GTG |
| GCC | ACC | TGG | GGA | ATT | TCC | GGC | ACA | CCA GCT CCT |
| CTT | GAC | TCA | GTG | TTC | TCC | AGC | AGC | GAG CGT GCC—3' |

M is 0 or 1, and
N is 0 or 1,
provided that when M is 0, N must necessarily also be 0; and that when R is 5'-GCC CAC CAG GTG CTG CGG ATC CGC AAA CGT-3',
R¹ must necessarily be

| | | | | | | | | |
|---|---|---|---|---|---|---|---|---|
| 5'-ATG | TGG | CAG | CTC | ACA | AGC | CTC | CTG | TTC GTG |
| GCC | ACC | TGG | GGA | ATT | TCC | GGC | ACA | CCA GCT CCT |
| CTT | GAC | TCA | GTG | TTC | TCC | AGC | AGC | GAG CGT—3'; | and that when
R is 5'-CAC CAG GTG CTG CGG ATC CGC AAA CGT-3',
R¹ must necessarily be

| | | | | | | | | |
|---|---|---|---|---|---|---|---|---|
| 5'-ATG | TGG | CAG | CTC | ACA | AGC | CTC | CTG | TTC GTG |
| GCC | ACC | TGG | GGA | ATT | TCC | GGC | ACA | CCA GCT CCT |
| CTT | GAC | TCA | GTG | TTC | TCC | AGC | AGC | GAG CGT GCC—3'. |

The compounds of the present invention encode human protein C, and the heretofore unknown amino acid sequence of nascent human protein C when M and N are 1. The amino acid sequence, numbered to facilitate further discussion, of nascent human protein C is:

```
                        5                  10                 15
H₂N—MET TRP GLN LEU THR SER LEU LEU PHE VAL ALA THR TRP GLY ILE
              20                 25                 30
    SER GLY THR PRO ALA PRO LEU ASP SER VAL PHE SER SER GLU ARG
         35                 40                 45
    ALA HIS GLN VAL LEU ARG ILE ARG LYS ARG ALA ASN SER PHE LEU GLU
         50                 55                 60
    GLU LEU ARG HIS SER SER LEU GLU ARG GLU CYS ILE GLU GLU ILE CYS
    65                 70                 75                 80
    ASP PHE GLU GLU ALA LYS GLU ILE PHE GLN ASN VAL ASP ASP THR LEU
                     85                 90                 95
    ALA PHE TRP SER LYS HIS VAL ASP GLY ASP GLN CYS LEU VAL LEU PRO
                    100                105                110
    LEU GLU HIS PRO CYS ALA SER LEU CYS CYS GLY HIS GLY THR CYS ILE
```

```
                    115                     120                     125
        ASP GLY ILE GLY SER PHE SER CYS ASP CYS ARG SER GLY TRP GLU GLY 130                     135                     140
        ARG PHE CYS GLN ARG GLU VAL SER PHE LEU ASN CYS SER LEU ASP ASN 145                     150                     155                     160
        GLY GLY CYS THR HIS TYR CYS LEU GLU GLU VAL GLY TRP ARG ARG CYS 165                     185                     190
        SER CYS ALA PRO GLY TYR LYS LEU GLY ASP ASP LEU LEU GLN CYS HIS 180                     185                     190
        PRO ALA VAL LYS PHE PRO CYS GLY ARG PRO TRP LYS ARG MET GLU LYS 195                     200                     205
        LYS ARG SER HIS LEU LYS ARG ASP THR GLU ASP GLN GLU ASP GLN VAL 210                     215                     220
        ASP PRO ARG LEU ILE ASP GLY LYS MET THR ARG ARG GLY ASP SER PRO 225                     230                     235                     240
        TRP GLN VAL VAL LEU LEU ASP SER LYS LYS LYS LEU ALA CYS GLY ALA 245                     250                     255
            VAL LEU ILE HIS PRO SER TRP VAL LEU THR ALA ALA HIS CYS MET ASP 260                     265                     270
        GLU SER LYS LYS LEU LEU VAL SRG LEU GLY GLU TYR ASP LEU ARG ARG 275                     280                     285
        TRP GLU LYS TRP GLU LEU ASP LEU ASP ILE LYS GLU VAL PHE VAL HIS 290                     295                     300
        PRO ASN TYR SER LYS SER THR THR ASP ASN ASP ILE ALA LEU LEU HIS 305                     310                     315                     320
        LEU ALA GLN PRO ALA THR LEU SER GLN THR ILE VAL PRO ILE CYS LEU 325                     330                     335
        PRO ASP SER GLY LEU ALA GLU ARG GLU LEU ASN GLN ALA GLY GLN GLU 340                     345                     350
        THR LEU VAL THR GLY TRP GLY TYR HIS SER SER ARG GLU LYS GLU ALA 355                     360                     365
        LYS ARG ASN ARG THR PHE VAL LEU ASN PHE ILE LYS ILE PRO VAL VAL 370                     375                     380
        PRO HIS ASN GLU CYS SER GLU VAL MET SER ASN MET VAL SER GLU ASN 385                     390                     395                     400
        MET LEU CYS ALA GLY ILE LEU GLY ASP ARG GLN ASP ALA CYS GLU GLY 405                     410                     415
        ASP SER GLY GLY PRO MET VAL ALA SER PHE HIS GLY THR TRP PHE LEU 420                     425                     430
        VAL GLY LEU VAL SER TRP GLY GLU GLY CYS GLY LEU LEU HIS ASN TYR 435                     440                     445
        GLY VAL TYR THR LYS VAL SER ARG TYR LEU ASP TRP ILE HIS GLY HIS 450                     455                     460
                ILE ARG ASP LYS GLU ALA PRO GLN LYS SER TRP ALA PRO—COOH
``` wherein
H₂N- is the amino-terminus,
—COOH is the carboxy-terminus,
ALA is Alanine,
ARG is Arginine,
ASN is Asparagine,
ASP is Aspartic acid,
CYS is Cysteine,
GLN is Glutamine,
GLU is Glutamic Acid,
GLY is Glycine,
HIS is Histidine,
ILE is Isoleucine,
LEU is Leucine,
LYS is Lysine,
MET is Methionine,
PHE is Phenylalanine,
PRO is Proline,
SER is Serine,
THR is Threonine,
TRP is Tryptophan,
TYR is Tyrosine, and
VAL is Valine.

The DNA compounds of the present invention are derived from cDNA clones prepared from human liver mRNA that encodes human protein C activity. In constructing the cDNA clones, a 5' poly G sequence, a 3' poly C sequence, and both 5' and 3' PstI restriction enzyme recognition sequences were constructed at the ends of the protein C-encoding cDNA. Two of these cDNA clones were manipulated to construct a DNA molecule comprising both the coding sequence of nascent human protein C and also portions of the DNA encoding the untranslated mRNA at the 5' and 3+ ends of the coding region. This DNA molecule was inserted into the PstI site of plasmid pBR322 to construct plasmid pHC7. Plasmid pHC7 thus comprises both the coding sequence above, wherein M and N both equal 1, and, again depicting only one strand of the molecule, also contains these additional sequences:

```
5'-C TGC AGG GGG GGG GGG GGG GGG GGG CTG TCA TGG CGG CAG GAC
    GGC GAA CTT GCA GTA TCT CCA CGA CCC GCC CCT ACA GGT GCC
    AGT GCC TCC AGA-3'
``` and

```
5'-CGA CCC TCC CTG CAG GGC TGG GCT TTT GCA TGG CAA TGG ATG GGA
    CAT TAA AGG GAC ATG TAA CAA GCA CAC CCC CCC CCC CCC CCC CCC
    CCC CCC CCT GCA G—3'
``` wherein
A is deoxyadenyl,
G is deoxyguanyl,
C is deoxycytidyl, and
T is thymidyl,
at the 5' and 3' ends, respectively, of the coding strand of the nascent human protein C coding sequence. Due to the complementary nature of DNA base-pairing, the sequence of one strand of a double-stranded DNA molecule is sufficient to determine the sequence of the opposing strand. Plasmid pHC7 can be conventionally isolated from E. coli K12 RR1/pHC7, a strain deposited with and made part of the permanent stock culture collection of the Northern Regional Research Laboratory (NRRL), Peoria, Ill. A culture of E. coli K12 RR1/pHC7 can be obtained from the NRRL under the accession number NRRL B-15926. A restriction site and function map of plasmid pHC7 is presented in FIG. 1 of the accompanying drawings.

As stated above, a variety of recombinant DNA expression vectors comprising the protein C activity-encoding DNA have been constructed. The present vectors are of two types: those designed to transform eukaryotic, especially mammalian, host cells; and those designed to transform E. coli. The eukaryotic or mammalian vectors exemplified herein can also transform E. coli, but the eukaryotic promoter present on these plasmids for transcription of the protein C activity-encoding DNA functions inefficiently in E. coli.

The present DNA compounds which encode nascent human protein C are especially preferred for the construction of vectors for transformation of, and expression of protein C activity in, mammalian and other eukaryotic host cells. Many mammalian host cells possess the necessary cellular machinery for the recognition and proper processing of the signal peptide present on the amino-terminus of nascent human protein C. Some mammalian host cells also provide the post-translational modifications, such as glycosylation, γ-carboxylation, and β-hydroxylation, as are observed in human protein C present in blood plasma. A wide variety of vectors exist for the transformation of eukaryotic host cells, and the specific vectors exemplified below are in no way intended to limit the scope of the present invention.

The pSV2-type vectors comprise segments of the SV0 genome that constitute a defined eukaryotic transcription unit—promoter (ep), intervening sequence (IVS), and polyadenylation (pA) site. In the absence of SV40 t-antigen, the plasmid pSV2-type vectors transform mammalian and other eukaryotic host cells by integrating into the host cell chromosomal DNA. A variety of plasmid pSV2-type vectors have been constructed (see Eukaryotic Viral Vectors, edited by Gluzman, published by Cold Spring Harbor Laboratories, Cold Spring Harbor, N.Y., 1982), such as plasmids pSV2-gpt, pSV2-neo, pSV2-dhfr, and pSV2-β-globin, in which the SV40 promoter drives transcription of an inserted gene. These vectors are available either from the American Type Culture Collection (ATCC) in Rockville, Md. or from the Northern Regional Research Laboratory (NRRL) in Peoria, Ill.

Plasmid pSV2-HPC8 is a vector of the present invention derived from plasmid pSV2-gpt (ATCC 37145), plasmid pHC7, and two synthetic linkers. The designation "gpt" refers to the E. coli xanthine-guanosine phosphoribosyl transferase gene present on plasmid pSV2-gpt. Plasmid pSV2-HPC8 was constructed by first preparing a HindIII-ApaI restriction fragment, derived from plasmid pHC7 and comprising the amino-terminal half of the nascent protein C coding sequence and a synthetic linker; then preparing an ApaI-BglII restriction fragment, derived from plasmid pHC7 and comprising the carboxy-terminal half of the nascent protein C coding sequence and a synthetic linker; and then inserting the two restriction fragments into HindIII-BglII-cleaved plasmid pSV2-gpt. A more detailed description of the construction of plasmid pSV2-HPC8 is provided in Example 2; a restriction site and function map of the plasmid is presented in FIG. 2 of the accompanying drawings.

Plasmid pSV2-HPC8 was used as a starting material in the construction of plasmid pL133, along with plasmid pSV2-β-globin (NRRL B-15928). Two restriction fragments of plasmid pSV2-HPC8, an ~0.29 kb HindIII-SalI fragment and an ~1.15 kb SalI-BglII fragment, comprising the entire nascent protein C coding region were ligated into HindIII-BglII-cleaved plasmid pSV2-β-globin. The resulting plasmid, designated pL133, has entirely replaced the β-globin coding region with the nascent protein C coding region. A more detailed description of the construction of plasmid pL133 is presented in Example 3; a restriction site and function map of the plasmid is presented in FIG. 3 of the accompanying drawings.

Plasmid pL132 was constructed in a manner analogous to the construction of plasmid pL133, except that the plasmid pSV2-HPC8 HindIII-SalI and SalI-BglII restriction fragments were introduced into plasmid pSV2-neo (ATCC 37149). "Neo" signifies the presence on the plasmid of a neomycin resistance-conferring gene, which also confers G418 resistance. This construction, described in Example 4, creates a polycistron, with both the nascent protein C and the G418 resistance-conferring coding sequences being transcribed as a polycistronic mRNA initiated by the same SV40 early promoter. Because G418 is toxic to most eukaryotic and other host cells, plasmid pL132 transformants can be selected by screening for G418 resistance. A restriction site and function map of plasmid pL132 is presented in FIG. 4 of the accompanying drawings.

Plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification, described in a review article by Schimke, 1984, Cell 37:705-713, can involve DNA sequences closely contiguous with the dhfr gene. Plasmid pL141 is a vector of the present invention comprising both the dhfr gene and also the nascent protein C structural gene under the control of the SV40 early promoter.

To construct plasmid pL141, a single BamHI site on plasmid pSV2-dhfr was converted to an XhoI site, yielding plasmid pSV2-dhfr-X. Two restriction fragments of plasmid pL133, an ~0.64 kb PvuII-BstEII fragment and an ~2.7 kb BstEII-EcoRI fragment, comprising the nascent protein C structural gene, were isolated and, after first converting the PvuII-BstEII fragment into an XhoI-BstEII fragment, ligated into EcoRI-XhoI-cleaved plasmid pSV2-dhfr-X. The resultant plasmid, designated pL141, is illustrated in FIG. 5 of the accompanying drawings; the construction is also described in Example 5.

Illustrative plasmids of the present invention which were constructed for expression of protein C activity in mammalian and other eukaryotic host cells also utilize promoters other than the SV40 early promoter. The present invention is in no way limited to the use of the particular eukaryotic promoters exemplified herein. Other promoters, such as the SV40 late promoter or promoters from eukaryotic genes, such as, for example, the estrogen-inducible chicken ovalbumin gene, the interferon genes, the glucocorticoid-inducible tyrosine aminotransferase gene, the thymidine kinase gene, and the major early and late adenovirus genes, can be readily isolated and modified for use on recombinant DNA expression vectors designed to produce protein C in eukaryotic host cells. Eukaryotic promoters can also be used in tandem to drive expression of protein C. Furthermore, a large number of retroviruses are known that infect a wide range of eukaryotic host cells. Long terminal repeats in the retrovirus DNA often encode promoter activity and can be used, in place of the SV40 early promoter described above, to drive expression of human protein C.

Plasmid pRSVcat (ATCC 37152) comprises portions of the long terminal repeat of the Rous Sarcoma virus (RSV), a virus known to infect chicken and other host cells. The RSV long terminal repeat sequences can be isolated on an ~0.76 kb NdeI-HindIII restriction fragment of plasmid pRSVcat. When cloned into the ~5.1 kb NdeI-HindIII fragment of plasmid pL133, the promoter in the RSV long terminal repeat (Gorman et al., 1982, P.N.A.S. 79:6777) replaces the SV40 early promoter and is positioned correctly to drive transcription and expression of the nascent human protein C structural gene. The resultant plasmid, designated pL142, is illustrated in FIG. 6 of the accompanying drawings.

The construction of plasmid pL142 is also described in Example 6.

Another plasmid of the present invention utilizes the Rous Sarcoma virus long terminal repeat promoter to drive expression of protein C and contains the dhfr gene for purposes of selection and gene amplification. The plasmid, designated pL151, was constructed by ligating the ~4.2 kb EcoRI-XhoI restriction fragment of plasmid pSV2-dhfr-X to the ~1.06 kb BstEII-NdeI restriction fragment of plasmid pL142 and to the ~2.74 kb BstEII-EcoRI restriction fragment of plasmid pL133. In order to accomplish the ligation and construction of plasmid pL151, the NdeI site of the pL142 restriction fragment used in the ligation was converted to an XhoI site by the addition of DNA linkers. The construction of plasmid pL151 is described in Example 9, below, and a restriction site and function map of the plasmid is presented in FIG. 9 of the accompanying drawings.

Plasmid pMSVi (NRRL B-15929) comprises the long terminal repeats of the Murine Sarcoma virus (MSV), a virus known to infect mouse and other host cells. Cloning the ~1.4 kb BclI restriction fragment of plasmid pSV2-HPC8 into the single BglII restriction enzyme recognition sequence of plasmid pMSVi places the nascent protein C structural gene under the control of the MSV long terminal repeat promoter. The resulting plasmid, designated pMSV-HPC, is illustrated in FIG. 7 of the accompanying drawings. The construction of plasmid pMSV-HPC is also described in Example 7.

The mouse metallothionein (MMT) promoter has also been well characterized for use in eukaryotic host cells. The MMT promoter is present in the 15 kb plasmid pdBPV-MMTneo (ATCC 37224), which is the starting material for the construction of another plasmid of the present invention, designated pMMTΔBPV-HPC. To construct plasmid pMMTΔBPV-HPC, plasmid pdBPV-MMTneo was first digested with BamHI and then religated to form plasmid pMMTΔBPV. This BamHI deletion removes ~8 kb of bovine papillomavirus (BPV) DNA. Plasmid pMMTΔBPV was then digested with BglII, and the ~1.4 kb BclI restriction fragment of plasmid pSV2-HPC8 was ligated into the BglII-digested plasmid. The resulting plasmid, designated pMMTΔBPV-HPC, comprises the nascent protein C structural gene positioned for transcription and expression from the MMT promoter. Immediately adjacent to and downstream of the nascent protein C structural gene in plasmid pMMTΔBPV-HPC is the G418 resistance-conferring gene, which is controlled by the metallothionein promoter and allows for selection of hosts transformed with plasmid pMMTΔBPV-HPC. The construction of plasmid pMMTΔBPV-HPC is described in Example 8; a restriction site and function map of the plasmid is presented in FIG. 8 of the accompanying drawings.

The vectors described above, excluding plasmid pHC7, can be transformed into and expressed in a variety of eukaryotic, especially mammalian, host cells. Because plasmids pSV2-HPC8, pL142, and pL133 possess no selectable marker with which to isolate and identify stable transformants, these vectors are most useful for purposes of transient assay, as described in Example 14 below, or for purposes of cotransformation, a procedure disclosed in U.S. Pat. No. 4,399,216, issued Aug. 26, 1983 and incorporated herein by reference. All of the vectors, including plasmid pHC7, comprise sequences that allow for replication in E. coli, as it is usually more efficient to prepare plasmid DNA in *E. coli* than in other host organisms.

Expression of the nascent human protein C structural gene contained on the above-described vectors occurs in those host cells in which the particular promoter associated with the nascent human protein C structural gene functions. The SV40 early promoter, the Rous Sarcoma virus long terminal repeat promoter, the Murine Sarcoma virus long terminal repeat promoter, and the mouse metallothionein promoter function in a wide variety of host cells. Preferred host cells for plasmids pSV2-HPC8, pL133, pL132, pL151, pL141, pMSV-PC, pMMTΔBPV-HPC and pL142 are listed in Table I, along with appropriate comments.

ity and can be used to study post-translational modification.

These novel derivatives can also be used as antigen to stimulate protein C-specific antibody production or can be used in protein C assays. Many assays use competitive antibody-binding to measure levels of a protein in a sample. Thus, radioactively (or other) labelled, prokaryotic-produced, human protein C can be used as the "competing molecule" in an assay for protein C in blood plasma. Skilled artisans will readily understand that the ability to conduct such assays is essential during any in- or out-patient therapeutic course of treatment involving protein C and for diagnostic purposes in patients with coagulation problems.

TABLE I

Preferred Host Cells for Plasmids pSV2-HPC8, pL133, pL132, pL151, pL141, pMSV-HPC, pMMTΔBPV-HPC, and pL142.

| | Origin | Source | Comments |
|---|---|---|---|
| Host Cell | | | |
| HepG-2 | Human Liver Hepatoblastoma | *ATCC # HB 8065 | U.S. Pat. No. 4,393,133 describes the use of this cell line. |
| *Aedes aegypti* | Mosquito Larvae | ATCC # CCL 125 | |
| CV-1 | African Green Monkey Kidney | ATCC # CCL 70 | |
| LLC-MK$_2$ original | Rhesus Monkey Kidney | ATCC # CCL 7 | |
| LLC-MK$_2$ derivative | Rhesus Monkey Kidney | ATCC # CCL 7.1 | Grows faster than ATCC # CCL 7 |
| 3T3 | Mouse Embryo Fibroblasts | ATCC # CCL 92 | |
| CHO-K1 | Chinese Hamster Ovary | ATCC # CCL 61 | Proline-requiring. Derivatives of CHO-K1, such as the dhfr$^-$ derivative DXB11, can be generated from this host. |
| *Antheraea eucalypti* | Moth ovarian tissue | ATCC # CCL 80 | |
| HeLa | Human Cervix Epitheloid | ATCC # CCL 2 | |
| RPMI8226 | Human Myeloma | ATCC # CCL 155 | IgG lambda-type light chain secreting |
| H4IIEC3 | Rat Hepatoma | ATCC # CRL 1600 | Derivatives, such as 8-azaguanine-resistant FAZA host cells, can be generated from this host. |
| C127I | Mouse Fibroblast | ATCC # CRL 1616 | |
| HS-Sultan | Human Plasma Cell Plasmocytoma | ATCC # CRL 1484 | |

*American Type Culture Collection, 12301 Parklawn Drive, Rockville, Maryland 20852-1776

Preferred transformants of the present invention are: HepG-2/pL132, HepG-2/pMSV-HPC, HepG-2/pL141, HepG-2/pL151, HepG-2/pMMTΔBPV-HPC, H4IIEC3/pL141, H4IIEC3/pL132, H4IIEC3/pMMTΔBPV-HPC, H4IIEC3/pMSV-HPC, H4IIEC3/pL151, LLC-MK$_2$/pL132, LLC-MK$_2$/pMMTΔBPV-HPC, LLC-MK$_2$/pL141, LLC-MK$_2$/pL151, C127I/pMMTΔBPV-HPC, C127/pMSV-HPC, C127I/pL151, 3T3T3/pL132, 3T3/pL141, 3T3/pL151, RPMI8226/pMSV-HPC, RPMI8226/pMMTΔBPV-HPC, RPMI8226/pL132, RPMI8226/pL141, RPMI8226/pL151, CHO-K1/pMSV-HPC, CHO-K1/pMMTΔBPV-HPC, CHO-K1/pL132, CHO-K1/pL141, CHO-K1/pL151, CHO-K1(dhfr$^-$)/pMSV-HPC, CHO-K1(dhfr$^-$)/pMMTΔBPV-HPC, CHO-K1(dhfr$^-$)/pL151

The present DNA compounds can also be expressed in prokaryotic host cells such as, for example, *E. coli*, *Bacillus*, and *Streptomyces*. Since prokaryotic host cells usually do not glycosylate, γ-carboxylate, or β-hydroxylate mammalian proteins made from recombinant genes, a variety of novel human protein C derivatives can be produced by expressing the present protein C activity-encoding DNA in prokaryotic host cells. The novel protein C derivatives expressed in prokaryotic host cells show varying degrees of protein C activ- Furthermore, the anticoagulant activity of human protein C can be separated from the profibrinolytic activity of human protein C by removing the γ-carboxylated glutamic acid residues from the protein. Activated human protein C contains several γ-carboxylated glutamic acid (gla) residues clustered near the aminoterminus of the light chain, and removal of these residues destroys the anticoagulant activity but not the profibrinolytic activity of the resulting "gla-less" protein C. The present invention provides for the production of gla-less protein C in two distinct ways: (1) by deleting the DNA encoding amino acid residues 1–83, the "gla-domain" of human protein C, of the nascent human protein C structural gene and expressing the deleted DNA in eukaryotic (or prokaryotic) host cells; or (2) by expressing the nascent human protein C structural gene, or a subfragment or derivative thereof, in *E. coli* or other suitable prokaryotic host cells which do not γ-carboxylate recombinant-produced human protein C.

Before expressing the protein C activity-encoding DNA compounds of the present invention in prokaryotic host cells, the eukaryotic signal peptide-encoding DNA was removed. Theoretically, the first 33 amino acid residues at the amino-terminus of nascent human protein C act as a signal peptide to direct secretion of protein C from the liver into the bloodstream. The present invention is not limited to the use of a particular eukaryotic signal peptide for expression of protein C activity in eukaryotic host cells. As a general rule, prokaryotes do not efficiently process eukaryotic signal peptides; therefore, it would probably be somewhat inefficient to express the signal peptide-encoding portion of the nascent human protein C structural gene in prokaryotes. Although not specificallly exemplified herein, the present invention also comprises the fusion of a prokaryotic signal peptide-encoding DNA to the protein C activity-encoding DNA of teh present invention for expression and secretion of protein C activity in porkaryotes.

As stated above, amino acid residues 1–33 of nascent human protein C may encode a "signal" for extracellular secretion and are not present in active protein C. Residues 34–42 of nascent human protein C, which comprises the pro peptide of human protein C, are also removed during the processing and activation of the protein and are believed to be responsible for the correct folding and modification of the molecule. Residues 33–42 of nascent human protein C are encoded in the prokaryotic expression vector exemplified below, but the present invention also comprises the prokaryotic expression vector encoding residues 34–42, and not residue 33, of nascent human protein C.

However, the present invention is not limited to the expression of a particular protein C derivative. The present DNA compounds are readily modified to delete that portion encoding amino acid residues 1–42 or 1–83 of nascent human protein C for expression of the resulting derivative. Furthermore, the present compounds are easily manipulated to separate the DNA encoding the active human protein C light chain (amino acid residues 43–197) from the DNA encoding the active human protein C heavy chain (amino acid residues 212–461), for the construction of vectors that drive expression of either the light or heavy chain of active human protein C. In this manner, the two chains can be independently produced in suitable, whether eukaryotic or prokaryotic, host cells and then chemically recombined to synthesize active human protein C.

In addition to the proteolytic processing described above involving amino acid residues 1–42, 198, and 199 of nascent human protein C, the activation of the protein C zymogen also involves the removal of amino acid residues 200–211. This processing occurs naturally in vivo and, more specifically, is believed to occur in the bloodstream. A variety of useful protein C derivatives exist during activation, any of which could be encoded on a recombinant DNA expression vector. Such a vector would allow the recombinant production of an inactive form of human protein C that could be activated in the human circulatory system or in accordance with the procedure of Example 15.

Separate production and subsequent chemical recombination of the light and heavy chains of human protein C can also be used to create a variety of other useful protein C derivatives. For instance, producing a light chain molecule comprising either amino acid residues 33–197, 34–197, or 43–197 of nascent human protein C and chemically recombining that light chain with a heavy chain molecule comprising either amino acid residues 200–461 or 212–461 of nascent human protein C produces a protein C derivative that would either be active or active upon cleavage of the peptides comprising residues 33–42 or 34–42 and 200–211, and such cleavage naturally occurs in the human circulatory system.

Plasmid pCZ460 is a plasmid of the present invention designed to express protein C activity in *E. coli.* Plasmid pCZ460 was constructed from plasmid pCZ101, plasmid pHC7, and a variety of DNA linkers. Plasmid pCZ101 was described and disclosed in U.S. patent application Ser. No. 634,920, filed July 26, 1984. A brief description of the construction of plasmid pCZ101 is provided below and a detailed description is provided in Examples 10 and 11 and FIGS. 10–17. A restriction site and function map of pCZ101 is presented in FIG. 18 of the accompanying drawings.

The plasmid pCZ101 starting material is ~10.8 kb and is constructed by ligating the ~0.6 kb XbaI-BamHI fragment of plasmid pNM789B into similarly digested plasmid pIM-I'-A3. The latter plasmid, which contains the transcriptional and translational activating sequence of the *E. coli* lipoprotein gene as well as a runaway replicon, can be obtained from *E. coli* K12 RV308/pIM-I'-A3, a strain deposited and made part of the permanent stock culture collection of the Northern Regional Research Laboratory under the accession number NRRL B-15733.

The plasmid pNM789B starting material is derived from plasmid pKEN111 in accordance with the steps illustrated and described in FIGS. 10–17 and Example 10 below. Plasmid pKEN111 can be obtained from *E. coli* K12 CC620/pKEN111, a strain part of the permanent stock culture collection of the Northern Regional Research Laboratory under the accession number NRRL B-15011. Plasmid pNM789B also contains the promoter and translational activating sequence of the *E. coli* lipoprotein gene and, in addition, the coding sequence, including an appropriately positioned translational stop signal, for a fusion protein comprising bovine growth hormone (bGH) and a nine amino acid residue polypeptide at the bGH amino-terminus. Ligation of the fusion protein-coding sequence, contained in the XbaI-BamHI fragment, to appropriately cleaved plasmid pIM-I'-A3 results in the aforementioned plasmid pCZ101 starting material.

Through a variety of manipulations, described in Example 12, a synthetic XbaI-NdeI linker was introduced downstream from the lpp promoter in plasmid pCZ101. The resulting plasmid, designated pCZ11, was further modified by the addition of another DNA linker encoding a methioninyl residue and amino acid residues 33–39 of nascent human protein C (as numbered above). This plasmid, designated pCZ451, was then cut with BamHI, and then the ~1.2 kb BamHI fragment of plasmid pHC7, encoding amino acid residues 39–445, was inserted to yield plasmid pCZ455. Plasmid pCZ455 was further modified to remove an extra NdeI linker inadvertently attached during an earlier construction step, yielding plasmid pCZ459.

Plasmid pCZ459 comprises the lpp promoter positioned for expression of DNA encoding a methionyl residue and amino acid residues 33–445 of nascent human protein C. In *E. coli* K12 RV308, at temperatures where copy number control is lost (> ~25° C.), plasmid pCZ459 expresses a functional polypeptide of molecular weight of about 50 kilodaltons which comprises a methionyl residue, amino acid residues 33–445 of nascent human protein C, and about 36 amino acid residues encoded by plasmid DNA initially isolated from the *E. coli* lpp gene. A restriction site and function map of plasmid pCZ459 is presented in FIG. 20 of the accompanying drawings.

DNA encoding amino acid residues 446–461 of the carboxy-terminus of human protein C was introduced into plasmid pCZ459 to give plasmid pCZ460. The construction of plasmid pCZ460 was accomplished by first inserting the ~0.88 kb PstI restriction fragment of plasmid pHC7, comprising the carboxy-terminus-encoding DNA, into plasmid pUC19 (commercially available from Pharmacia, Inc., 800 Centennial Dr., Piscataway, NJ 08854) to yield plasmid pUC19HC. Plasmid pUC19HC comprises an ~80 bp BamHI restriction fragment from which the carboxy-terminus-encoding DNA of the protein C structural gene can be isolated. Plasmid pUC19HC was cleaved with BamHI, and the ~80 bp BamHI fragment was isolated and inserted into plasmid pCZ459 to yield plasmid pCZ460. Plasmid pCZ460 encodes and drives expression of a polypeptide identical to nascent protein C, except for the absence of amino acid residues 2–32. The construction of plasmids pUC19HC and pCZ460 is described in more detail in Example 13.

Expression of human protein C activity in *E. coli* is in no way limited to the use of a particular promoter, since the choice of a specific promoter is not critical to the operability of the present invention. Promoters which can be substituted for the previously exemplified lipoprotein promoter include, but are not limited to, the *E. coli* lactose (lac), the *E. coli* trp, bacteriophage $\lambda P_L O_L$, and bacteriophage $\lambda P_R O_R$ promoters. In addition, one or more promoters can be used in tandem, such as, for example, the trp and lac promoters, or hybrid promoters, such as the tac promoter, can be used to drive expression of the protein C structural gene. All of the aforementioned promoters have been previously characterized, are well known in the art, and can be constructed either synthetically or from known plasmids.

Plasmid pCZ460 replication is determined by a thermoinducible runaway replicon disclosed in both GB Patent Publication No. 1,557,774 and Uhlin et al., 1979, Gene 6:91. At temperatures below 30° C., especially 25° C., the replicon maintains a relatively low copy number of about 10–15 copies per cell. When the temperature is raised to 37° C., copy number control is lost and plasmids containing the replicon amplify to 1000–2000 copies per cell. The particular runaway replicon exemplified herein is contained in the previously described plasmid pIM-I'-A3 starting material. Skilled artisans will understand that the present invention is not limited to the use of any particular runaway replicon or copy number mutant. Other inducible runaway or high copy number replicons can be obtained by appropriate selection or can be constructed in accordance with the procedure disclosed in International Publication No. WO82/02901. Such replicons can be used to construct expression vectors that are also within the scope of the present invention.

The cloning of foreign genes, such as the human protein C derivative gene of the present invention, into vectors containing a runaway replicon results, upon induction and loss of copy number control, in a greatly increased rate of protein synthesis and the concomitant formation of intracellular proteinaceous granules. The granules are highly homogeneous in their protein composition, with the desired protein product comprising at least 50% and often exceeding 80% by dry weight of the granule. The present granules can be readily isolated from cell lysates and are stable to washing in low concentrations of urea or detergents. Washing removes proteins that bind non-specifically to the granule.

However, the present invention is not limited to the use of a runaway replicon-containing plasmid for expression of protein C activity in *E. coli*. Many replicons, such as those from plasmids pBR322, pBR328, pACYC184, and the like, are known in the art and are suitable for the construction of recombinant DNA cloning and expression vectors designed to drive expression of the protein C-encoding DNA compounds of the present invention. Neither is the present invention limited to the actual selectable markers present on the plasmids exemplified herein. A wide variety of selectable markers exist, both for eukaryotic and prokaryotic host cells, that are suitable for use on a recombinant DNA cloning or expression vector comprising a DNA compound (or sequence) of the present invention.

Many modifications and variations of the present illustrative DNA sequences and plasmids are possible. For example, the degeneracy of the genetic code allows for the substitution of nucleotides throughout polypeptide coding regions as well as for the substitution of the

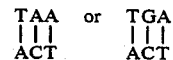

translational stop signals for the

translational for stop signal specifically exemplified. Such sequences can be deduced from the now-known amino acid or DNA sequence of human protein C and can be constructed by following conventional synthetic procedures. Such synthetic methods can be carried out in substantial accordance with the procedures of Itakura et al., 1977, Science 198:1056 and Crea et al., 1978, Proc. Nat. Acad. Sci. USA 75:5765. Therefore, the present invention is in no way limited to the DNA sequences and plasmids specifically exemplified.

The prokaryotic expression vectors and method of this invention can be applied to a wide range of host organisms, especially Gram-negative prokaryotic organisms such as *Escherichia coli*, *E. coli* K12, *E. coli* K12 RV308, *E. coli* K12 HB101, *E. coli* K12 C600, *E. coli* K12 RR1, *E. coli* K12 RR1ΔM15, *E. coli* K12 MM294, and the like. Although all of the embodiments of the present invention are useful, some of the vectors and transformants are preferred. A preferred transformant is *E. coli* K12 RV308/pCZ460.

Those skilled in the art will recognize that the expression vectors of this invention are used to transform either eukaryotic or prokaryotic host cells, such that a polypeptide with human protein C activity is expressed by the host cell. If the host cell is transformed with a vector comprising a promoter that functions in the host cell and drives transcription of the nascent human protein C structural gene, and if the host cell possesses the cellular machinery with which to process the signal peptide, protein C activity can be isolated from the media. Under other expression conditions, such as when plasmid pCZ460 is in *E. coli* RV308, the protein C activity must be isolated from the host cell.

As stated above, protein C produced by recombinant methodology will have a profound effect on the treatment of thrombotic disease. Persons who are homozygous or heterozygous for protein C deficiency suffer from severe thrombosis and are presently treated with clotting Factor IX concentrate, which contains protein C. For treatment of these human protein C-deficient homozygotes, assuming ~3000 ml of blood plasma and some diffusion into the extravascular space, recombinant-produced protein C can be administered twice daily at levels ranging from 5 mg to 100 mg per dose, assuming the zymogen form of the enzyme is administered. Heterozygotes for protein C deficiency will need lower doses of protein C than homozygotes, ranging from 2.5 mg to 50 mg per dose of the zymogen form of the enzyme.

Recombinant-produced protein C will also be useful in the prevention and treatment of a wide variety of acquired disease states involving intravascular coagulation, including deep vein thrombosis, pulmonary embolism, peripheral arterial thrombosis, emboli originating from the heart or peripheral arteries, acute myocardial infarction, thrombotic strokes, and disseminated intravascular coagulation. Experimental and clinical data suggest that conventional anticoagulants, particularly warfarin, are useful in the treatment of invasive cancers and act to prevent or reduce the distant metastatic lesions of these malignancies. Recombinant-produced protein C represents an attractive alternative to conventional anticoagulants in these clinical situations for the reasons detailed below.

Deep vein thrombosis and pulmonary embolism can be treated with conventional anticoagulants, but a far more attractive clinical approach is to prevent the occurrence of thromboembolic complications in identified high risk patients, such as, for example, patients undergoing surgery, patients who are chronically bedridden, and patients with congestive heart failure. Over 50% of surgical patients age 50 and over 20% of all surgical patients in general suffer from deep vein thrombosis following surgery, and about 20% of all post-surgical cases of deep vein thrombosis are complicated by one or more pulmonary emboli. Presently, low doses of heparin (e.g. 5,000 units every 8 hours) are administered both pre- and post-surgery to prevent deep vein thrombosis. Low-dose heparin occasionally causes heavy bleeding during and after surgery. Since activated protein C is more selective than heparin, being active only when and where thrombin is generated and fibrin thrombi are formed, protein C will be more effective and less likely to cause bleeding complications than heparin when used prophylactically for the prevention of deep vein thrombosis. The dose of recombinant-produced protein C for prevention of deep vein thrombosis is in the range from 1-10 mg/day, and administration of protein C should begin 6 hours prior to surgery and continue until the patient becomes mobile. In established, objectively-documented, deep vein thrombosis and/or pulmonary embolism, the dose of activated protein C ranges from 1-10 mg as a loading dose followed by a continuous infusion in amounts ranging from 3-30 mg/day. Similar dosage schedules are applicable for the treatment of peripheral arterial thrombi. Because of the lower likelihood of bleeding complications from activated protein C infusions, activated protein C can replace heparin intra- and post-surgically in conjunction with thrombectomies or embolectomies, surgical procedures which are often necessary to save ischemic limbs from amputation in the setting of an acute arterial obstruction.

Arterial emboli originating from the heart are frequent complications in diseases of the heart involving heart valves, in patients with artifical heart valves, in acute myocardial infarction, and in certain types of heart arrhythmias. The treatment of these problems with conventional oral anticoagulants is not always entirely effective, and as always when oral anticoagulants are used, the risk of bleeding complications is substantial. Activated protein C administered long-term, in doses comparable to those for the treatment of established deep vein thrombin-pulmonary embolism, through continuous infusion using portable pump systems has substantial utility in the prevention of cardiogenic emboli.

Similarly, emboli originating from thrombi in peripheral arteries, most notably the carotid arteries, are not treated or prevented satisfactorily with currently used regimens, which include drugs capable of suppressing platelet function, oral anticoagulants, or combinations thereof. As in the case of cardiogenic emboli, activated protein C administered long term in the same manner as outlined for cardiogenic emboli has major potential in the prevention of emboli originating from carotid artery thrombi and resulting in embolic strokes.

Recombinant protein C is also useful in the treatment of thrombotic strokes. Today, strokes are not usually treated with conventional anticoagulants. Treatment of strokes with either heparin or oral anticoagulants, although occasionally beneficial, carries a high risk for bleeding into the infarcted brain area, thereby aggravating the neurological deficit accompanying the stroke. Because of its low potential for causing bleeding complications and its selectivity, protein C can be given to stroke victims and is beneficial in preventing the local extension of the occluding arterial thrombus, thereby reducing the neurological deficit resulting from the stroke. The amount of active protein C administered will vary with each patient depending on the nature and severity of the stroke.

Recombinant-produced activated protein C will be a useful treatment in acute myocardial infarction because of the ability of activated protein C to enhance in vivo fibrinolysis. Activated protein C can be given with tissue plasminogen activator during the acute phases of the myocardial infarction. After the occluding coronary thrombus is dissolved, activated protein C can be given for additional days or weeks to prevent coronary reocclusion. In acute myocardial infarction, the patient is given a loading dose of 1-10 mg of activated protein C at the time tissue plasminogen activator treatment is initiated followed by a continuous infusion of activated protein C in amounts ranging from 3-30 mg/day.

Protein C zymogen or activated protein C is useful in the treatment of disseminated intravascular coagulation. As mentioned above, the levels of protein C in disseminated intravascular coagulation are severely reduced, probably through a mechanism which involves the widespread activation of the protein by thrombomodulin-thrombin and the subsequent catabolism or inactivation of the activated enzyme. Heparin and the oral anticoagulants have been given to patients with disseminated intravascular coagulation in extensive clinical trials, but the results of these trials have been disappointing. Characteristically, patients with disseminated intravascular coagulation have widespread thrombi involving the microcirculation with concomitant and often severe bleeding problems, which result from "consumption" of essential clotting factors, which have been first activated and then inactivated during the formation of widespread microcirculatory fibrin thrombi. In disseminated intravascular coagulation, protein C has a distinct advantage over conventional anticoagulants. Because of its selectivity, protein C will not aggravate the bleeding problems associated with disseminated intravascular coagulation, as do heparin and the oral anticoagulants, but retards or inhibits the formation of additional microvascular fibrin deposits. The protein C zymogen, rather than the activated serine protease, is the preparation of choice in disseminated intravascular coagulation; the substantial quantities of thrombomodulin-thrombin present in the microcirculation of these patients will insure complete activation of the zymogen into the active serine protease. The doses required are comparable to those used in homozygous or heterozygous protein C deficiency, depending on the quantities of protein C present in the circulation at the time of the start of treatment.

Evidence has been presented that conventional anticoagulant drugs, particularly warfarin, are useful in the treatment of invasive malignant tumors. Many tumor cells produce substances which trigger the activation of the coagulation system resulting in local fibrin deposits. These fibrin deposits function as "nests" in which cancer cells can divide to form metastatic lesions. In one clinical study, it was shown that patients receiving warfarin in addition to cancer chemotherapy for treatment of small cell carcinoma of the lung live longer and have less extensive metastatic lesions than patients receiving chemotherapy alone. However, the cancer chemotherapy utilized in this study was less intensive than that considered optimal in clinical oncology today. The more intensive forms of cancer chemotherapy almost always produce a sharp drop in the platelet count, and thrombocytopenia combined with warfarin therapy puts the patient in an unacceptably high risk for serious bleeding complications. Activated protein C, being more selective than conventional anticoagulants and having a far higher therapeutic index than either heparin or the oral anticoagulants, can be given relatively safely to the thrombocytopenic patient, thus enabling the treatment of patients with invasive cancers with effective intensive chemotherapy in combination with activated protein C. Treatment of invasive cancers with activated protein C will follow a dosage regimen comparable to that used in deep vein thrombosis-pulmonary embolism.

The compounds of the present invention can be formulated according to known methods to prepare pharmaceutically useful compositions, whereby the human protein C product of the present invention is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences* 16th ed., 1980, Mack Publishing Co., edited by Osol et al., which is hereby incorporated by reference. Such compositions will contain an effective amount of protein C together with a suitable amount of carrier vehicle in order to prepare pharmaceutically acceptable compositions suitable for effective administration to the host. The protein C composition can be administered parenterally, or by other methods that ensure its delivery to the bloodstream in an effective form.

The following examples further illustrate the invention disclosed herein. The examples describe the procedures for the construction of the present invention, and explanations of the procedures are provided where appropriate.

BRIEF DESCRIPTION OF THE FIGURES

FIGS. 10-17—the construction of plasmid pNM789B.

EXAMPLE 1

Figure 1:
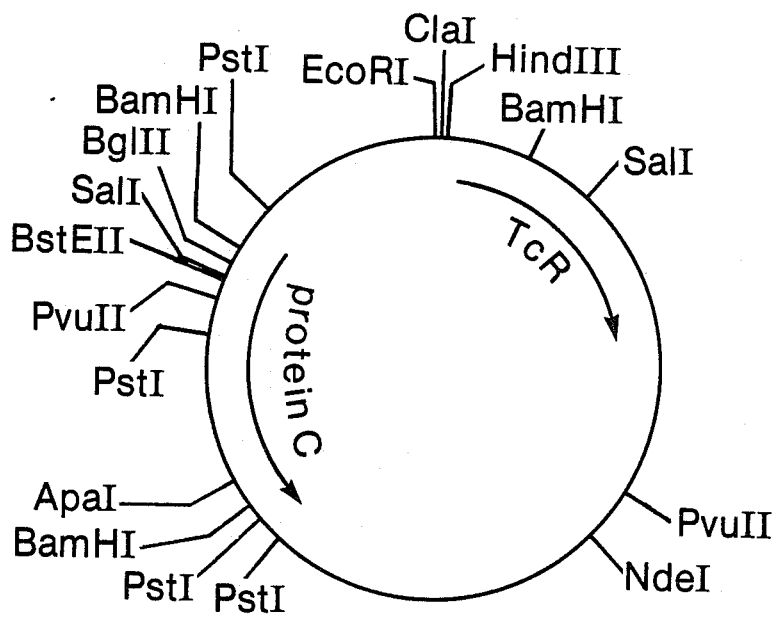
FIG. 1—the restriction site and function map of plasmid pHC7.

Culture of *E. coli* K12 RR1/pHC7 and Isolation of Plasmid pHC7

A. Culture of *E. coli* K12 RR1/pHC7

One liter of L-broth (10 g peptone, 10 g NaCl, and 5 g yeast extract) containing 15 μg/ml tetracycline was inoculated with a culture of *E. coli* RR1/pHC7 (NRRL B-15926) and incubated in an air-shaker at 37° C. until the optical density (O.D.) at 590 nm was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

B. Isolation of Plasmid pHC7

The culture prepared in Example 1A was centrifuged in a Sorvall GSA rotor (DuPont Co., Instrument Products, Biomedical Division, Newtown, CN 06470) at 6000 rpm for 5 minutes at 4° C. The resulting supernatant was discarded, and the cell pellet was washed in ~0 ml of TES buffer (10 mM Tris-HCl, pH=7.5; 10 mM NaCl; and 1 mM EDTA) and then repelleted. After discarding the supernatant again, the cell pellet was frozen in a dry ice-ethanol bath and then thawed. The thawed cell pellet was resuspended in 10 ml of a 25% sucrose/50 mM EDTA solution. After adding and mixing: 1 ml of a 5 mg/ml lysozyme solution; 3 ml of 0.25M EDTA, pH=8.0; and 100 μl of 10 mg/ml RNAse A, the solution was incubated on ice for 15 minutes. Three ml of lysing solution (prepared by mixing 3 ml 10% Triton-X 100; 75 ml 0.25M EDTA, pH=8.0; 15 ml of 1M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman 7360 N. Lincoln Ave., Lincolnwood, IL 60646). After adding 30.44 g of CsCl and ~1 ml of a 5 mg/ml ethidium bromide solution, the solution volume was adjusted to 40 ml and decanted into a Vti50 ultracentrifuge tube (Beckman). After sealing the tube, the solution was centrifuged in a Vti50 rotor at 42,000 rpm for ~16 hours. The resulting plasmid band, visualized with ultraviolet light, was isolated and then placed in a ti75 tube and rotor (Beckman) and centrifuged at 55,000 rpm for 16 hours. Any necessary volume adjustments were made using TES containing 0.761 g/ml CsCl. The plasmid band was again isolated, the ethidium bromide extracted with salt-saturated isopropanol, and diluted 1:3 with TES buffer. Two volumes of ethanol were then added to the solution, followed by incubation overnight at $-20°$ C. The plasmid DNA was pelleted by centrifuging the solution in an SS34 rotor (Sorvall) for 15 minutes at 10,000 rpm.

The ~1 mg of plasmid pHC7 DNA obtained by this procedure was suspended in 1 ml of TE buffer (10 mM Tris-HCl, pH=8.0 and 1 mM EDTA) and stored at $-20°$ C. A restriction site and function map of plasmid pHC7 is presented in FIG. 1 of the accompanying drawings.

EXAMPLE 2

Construction of Plasmid pSV2-HPC8

A. Isolation of the ~1.25 kb BanI Restriction Fragment of Plasmid pHC7

Fifty $\mu$l of the plasmid pHC7 DNA prepared in Example 1 were mixed with 5 $\mu$l (~50 Units) of restriction enzyme BanI, 10 $\mu$l of 10X BanI reaction buffer (1.5M NaCl; 60 mM Tris-HCl, pH=7.9; 60 mM MgCl$_2$; and 1 mg/ml BSA), and 35 $\mu$l of H$_2$O and incubated until the digestion was complete. The BanI-digested plasmid pHC7 DNA was then electrophoresed on a 3.5% polyacrylamide gel (29:1, acrylamide:bis-acrylamide), until the ~1.25 kb BanI restriction fragment was separated from the other digestion products. The DNA bands were visualized by first staining the gel with a dilute solution of ethidium bromide and then viewing the gel with ultraviolet light.

The region of the gel containing the ~1.25 kb BanI restriction fragment was cut from the gel, placed in a test tube, and broken into small fragments. One ml of extraction buffer (500 mM NH$_4$OAc, 10 mM MgOAc, 1 mM EDTA, 1% SDS, and 10 mg/ml tRNA) was added to the tube containing the fragments, which was placed at 37° C. overnight. Centrifugation was used to pellet the debris, and the supernatant was transferred to a new tube. The debris was washed once with 200 $\mu$l of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then the DNA was pelleted by centrifugation.

Approximately 8 $\mu$g of the ~1.25 kb BanI restriction fragment were obtained by this procedure. The purified fragment was suspended in 10 $\mu$l of TE buffer and stored at $-20°$ C.

B. Construction of the HindIII-BclI-BanI Linker

The DNA fragments used in the construction of the linker were synthesized either by using a Systec 1450A DNA Synthesizer (Systec Inc., 3816 Chandler Drive, Minneapolis, MN) or an ABS 380A DNA Synthesizer (Applied Biosystems, Inc., 850 Lincoln Centre Drive, Foster City, CA 94404). Many DNA synthesizing instruments are known in the art and can be used to make the fragments. In addition, the fragments can also be conventionally prepared in substantial accordance with the procedures of Itakura et al., 1977, Science, 198:1056 and Crea et al., 1978, Proc. Nat. Acad. Sci. USA, 75:5765.

Five hundred picomoles of each single strand of the linker were kinased in 20 $\mu$l of reaction buffer containing: 15 units (~0.5 $\mu$l) T4 polynucleotide kinase, 2 $\mu$l 10X ligase buffer (300 mM Tris-HCl, pH=7.8; 100 mM MgCl$_2$; 100 mM dithiothreitol; and 1 mg/ml BSA), 10 $\mu$l 500 $\mu$M ATP, and 7.5 $\mu$l H$_2$O. The kinase reaction was incubated at 37° C. for 30 minutes, and the reaction was terminated by incubation at 100° C. for 10 minutes. In order to ensure complete kination, the reaction was chilled on ice, 2 $\mu$l of 0.2M dithiothreitol, 2.5 $\mu$l of 5 mM ATP, and 15 units of T4 polynucleotide kinase were added, mixed, and the reaction mix incubated another 30 minutes at 37° C. The reaction was stopped by another 10 minute incubation at 100° C. and then chilled on ice.

Although kinased separately, the two single strands of the DNA linker were mixed together after the kinase reaction. In order to anneal the strands, the kinase reaction mixture was incubated at 100° C. for 10 minutes in a water bath containing ~150 ml of water. After this incubation, the water bath was shut off and allowed to cool to room temperature, a process taking about 3 hours. The water bath, still containing the tube of kinased DNA, was then placed in a 4° C. refrigeraoor overnight. This process annealed the single strands. The linker constructed had the following structure:

The linker was stored at $-20°$ C. until use.

C. Construction of the ~1.23 kb HindIII-ApaI Restriction Fragment

The ~8 $\mu$g of ~1.25 kb BanI fragment isolated in Example 2A were added to and mixed with the ~50 $\mu$l of linker (~500 picomoles) constructed in Example 2B, 1 $\mu$l T4 DNA ligase (~10 units), 10 $\mu$l 10X ligase buffer, 10 $\mu$l 10 mM ATP, and 19 $\mu$l H$_2$O, and the resulting ligation reaction was incubated at 4° C. overnight.

The ligation reaction was stopped by a 10 minute incubation at 65° C. The DNA was pelleted by adding NaOAc to 0.3M final concentration and 2 volumes of ethanol, chilling in a dry ice-ethanol bath, and then centrifuging the solution.

The DNA pellet was dissolved in 10 $\mu$l 10X ApaI reaction buffer (60 mM NaCl; 60 mM Tris-HCl pH=7.4; 60 mM MgCl$_2$; and 60 mM 2-mercaptoethanol), 5 $\mu$l (~50 units) restriction enzyme ApaI, and 85 $\mu$l of H$_2$O, and the reaction was placed at 37° C. for two hours. The reaction was then stopped and the DNA pelleted as above. The DNA pellet was dissolved in 10 μl 10× HindIII reaction buffer (500 mM NaCl; 500 mM Tris-HCl, pH=8.0; and 100 mM MgCl₂), 5 μl (~50 units) restriction enzyme HindIII, and 85 μl of H₂O, and the reaction was placed at 37° C. for two hours.

After the HindIII digestion, the reaction mixture was loaded onto a 3.5% polyacrylamide gel, and the desired μ1.23 kb HindIII-ApaI restriction fragment was isolated in substantial accordance with the teaching of Example 2A. Approximately 5 μg of the desired fragment were obtained, suspended in 10 μl of TE buffer, and stored at −20° C.

D. Isolation of the ~0.88 kb PstI Restriction Fragment of Plasmid pHC7

Fifty μl of the plasmid pHC7 DNA prepared in Example 1 were mixed with 5 μl (~50 units) of restriction enzyme PstI, 10 μl of 10× PstI reaction buffer (1.0M NaCl; 100 mM Tris-HCl, pH=7.5; 100 mM MgCl₂; and 1 mg/ml BSA), and 35 μl of H₂O and incubated at 37° C. for two hours. The PstI-digested plasmid pHC7 DNA was then electrophoresed on a 3.5% polyacrylamide gel, and the desired ~0.88 kb fragment was purified in substantial accordance with the procedure of Example 2A. Approximately 5 μg of the desired fragment were obtained, suspended in 10 μl of TE buffer, and stored at −20° C.

E. Construction of the PstI-BclI-BglII Linker

The following linker was constructed and prepared for ligation in substantial accordance with the procedure of Example 2B:

F. Construction of the ~0.19 kb ApaI-BglII Restriction Fragment

The ~5 μg of ~0.88 kb PstI fragment isolated in Example 2D were added to and mixed with the ~50 μl of linker (~500 picomoles) constructed in Example 2E, 1 μl T4 DNA ligase (~10 units), 10 μl 10× ligase buffer, 10 μl 10 mM ATP, and 19 μl H₂O, and the resulting ligation reaction was incubated at 4° C. overnight.

The ligation reaction was stopped by a 10 minute incubation at 65° C. After precipitation of the ligated DNA, the DNA pellet was dissolved in 10 μl 10× ApaI reaction buffer, 5 μl (~50 units) restriction enzyme ApaI, and 85 μl of H₂O, and the reaction was placed at 37° for two hours. The reaction was then stopped and the DNA pelleted once again. The DNA pellet was dissolved in 10 μl 10× BglII reaction buffer (1M NaCl; 100 mM Tris-HCl, pH=7.4; 100 mM MgCl₂; and 100 mM 2-mercaptoethanol), 5 μl (~50 units) restriction enzyme BglII, and 85 μl H₂O, and the reaction was placed at 37° C. for two hours.

After the BglII digestion, the reaction mixture was loaded onto a 3.5% polyacrylamide gel, and the desired ~0.19 kb ApaI-BglII restriction fragment was isolated in substantial accordance with the teaching of Example 2A. Approximately 1 μg of the desired fragment was obtained, suspended in 10 μl of TE buffer, and stored at −20° C.

G. Isolation of HindIII-BglII-Digested Plasmid pSV2-gpt

Approximately 10 μg of plasmid pSV2-gpt DNA (ATCC 37145) were dissolved in 10 μl 10× HindIII reaction buffer, 5 μl (~50 units) restriction enzyme HindIII, and 85 μl H₂O, and the reaction was placed at 37° C. for 2 hours. The reaction mixture was then made 0.25M in NaOAc, and after adding two volumes of ethanol and chilling in a dry ice-ethanol bath, the DNA was pelleted by centrifugation.

The DNA pellet was dissolved in 10 μl 10× BglII buffer, 5 μl (~50 units) restriction enzyme BglII, and 85 μl H₂O, and the reaction was placed at 37° C. for two hours. After the BglII digestion, the reaction mixture was loaded onto a 1% agarose gel, and the fragments were separated by electrophoresis. After visualizing the gel with ethidium bromide and ultraviolet light, the band containing the desired ~5.1 kb HindIII-BglII fragment was cut from the gel and placed in dialysis tubing, and electrophoresss was continued until the DNA was out of the agarose. The buffer containing the DNA from the dialysis tubing was extracted with phenol and CHCl₃, and then the DNA was precipitated. The pellet was resuspended in 10 μl of TE buffer and constituted ~5 μg of the desired ~5.1 kb HindIII-BglII restriction fragment of plasmid pSV2-gpt.

H. Ligation of Fragments to Construct Plasmid pSV2-HPC8

Figure 2:
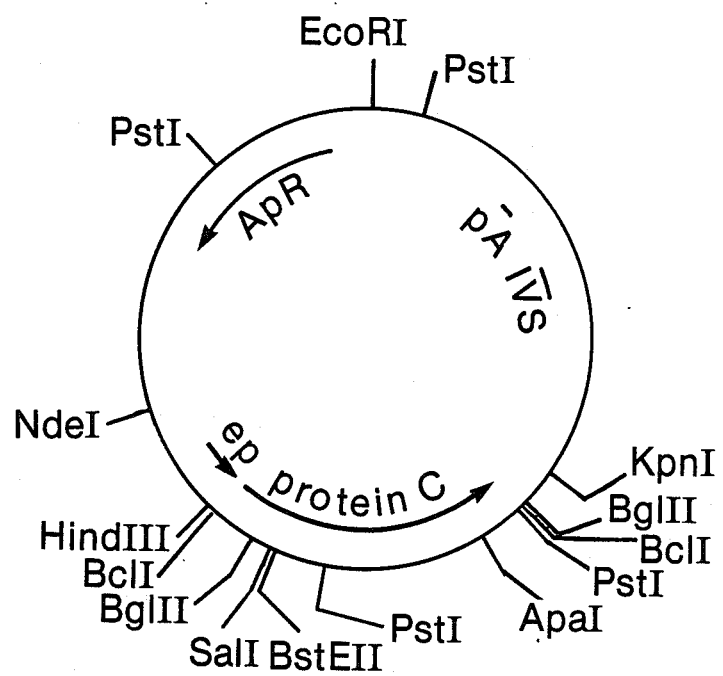
FIG. 2—the restriction site and function map of plasmid pSV2-HPC8.

Two μl of the ~1.23 kb HindIII-ApaI restriction fragment prepared in Example 2C, 3 μl of the ~0.19 kb ApaI-BglII fragment prepared in Example 2F, and 2 μl of the ~5.1 kb HindIII-BglII fragment prepared in Example 2G were mixed together and then incubated with 10 μl 10× ligase buffer, 10 μl 10 mM ATP, 1 μl T4 DNA ligase (~10 units), and 72 μl of H₂O at 16° C. overnight. The ligated DNA constituted the desired plasmid pSV2-HPC8; a restriction site and function map of the plasmid is presented in FIG. 2 of the accompanying drawings.

I. Construction of E. coli K12 RR1/pSV2-HPC8

A 50 ml culture of E. coli K12 RR1 (NRRL B-15210) in L-broth was grown to an O.D. at 590 nm of ~0.2. The culture was chilled on ice for ten minutes, and the cells were collected by centrifugation. The cell pellet was resuspended in 25 ml of cold 100 mM CaCl₂ and incubated on ice for 25 minutes. The cells were once again pelleted by centrifugation, and the pellet was resuspended in 2.5 ml of cold 100 mM CaCl₂ and incubated on ice overnight.

Two hundred μl of this cell suspension were mixed with the ligated DNA prepared in Example 2H and incubated on ice for 20 minutes. The mixture was then incubated at 42° C. for 2 minutes, followed by a 10 minute incubation at room temperature. Three ml of L-broth were added to the cell mixture, and then the cells were incubated in an air-shaker at 37° C. for two hours.

Aliquots of the cell mixture were plated on L-agar (L-broth with 15 g/l agar) plates containing 100 μg/ml ampicillin, and the plates were then incubated at 37° C. E. coli K12 RR1/pSV2-HPC8 transformants were verified by restriction enzyme analysis of their plasmid DNA. Plasmid DNA was obtained from the E. coli K12 RR1/pSV2-HPC8 in substantial accordance with the teaching of Example 1, except that ampicillin, not tetracycline, was the antibiotic used for selection.

EXAMPLE 3
Construction of Plasmid pL133

A. Isolation of the ~0.29 kb HindIII-SalI Restriction Fragment of Plasmid pSV2-HPC8

Fifty μg of plasmid pSV2-HPC8 were dissolved in 10 μl 10× HindIII reaction buffer, 5 μl (~50 units) restriction enzyme HindIII, and 85 μl H₂O, and the reaction was incubated at 37° C. for two hours. After the HindIII digestion, the DNA was precipitated, and the DNA pellet was dissolved in 10 μl 10× SalI reaction buffer (1.5M NaCl; 60 mM Tris-HCl, pH=7.9; 60 mM MgCl₂; 60 mM 2-mercaptoethanol; and 1 mg/ml BSA), 5 μl (~50 units) restriction enzyme SalI, and 85 μl of H₂O. The resulting SalI reaction mixture was incubated for 2 hours at 37° C.

The HindIII-SalI-digested plasmid pSV2-HPC8 was loaded onto a 3.5% polyacrylamide gel and electrophoresed until the desired ~0.29 kb HindIII-SalI restriction fragment was clearly separated from the other reaction products. The desired fragment was purified in substantial accordance with the teaching of Example 2A. The ~2 μg of fragment obtained were suspended in 10 μl of TE buffer and stored at −20° C.

Isolation of the ~1.15 kb SalI-BglII Restriction Fragment of Plasmid pSV2-HPC8

Fifty μg of plasmid pSV2-HPC8 were dissolved in 10 μl 10× BglII reaction buffer, 5 μl (50 units) restriction enzyme BglII, and 85 μl H₂O, and the reaction was incubated at 37° C. for two hours. After the BglII digestion, the DNA was precipitated, and the DNA pellet was dissolved in 10 μl 10× SalI reaction buffer, 5 μl restriction enzyme SalI, and 85 μl of H₂O. The resulting SalI reaction mixture was incubated for 2 hours at 37° C.

The SalI-BglII-digested plasmid pSV2-HPC8 was loaded onto a 3.5% polyacrylamide gel and electrophoresed until the desired ~1.15 kb SalI-BglII restriction fragment was clearly separated from the other reaction products. The desired fragment was purified in substantial accordance with the teaching of Example 2A. The ~8 μg of fragment obtained were suspended in 10 μl of TE buffer and stored at −20° C.

C. Isolation of the ~4.2 kb BglII-HindIII Restriction Fragment of Plasmid pSV2-β-globin The isolation of the desired ~4.2 kb BglII-HindIII restriction fragment of plasmid pSV2-β-globin (NRRL B-15928) was accomplished in substantial accordance with the teaching of Example 2G, with the exception that plasmid pSV2-β-globin, rather than plasmid pSV2-gpt, was used. The ~5 μg of DNA obtained were suspended in 10 μl of TE buffer and stored at −20° C.

D. Ligation of Fragments to Construct Plasmid pL133

Figure 3:
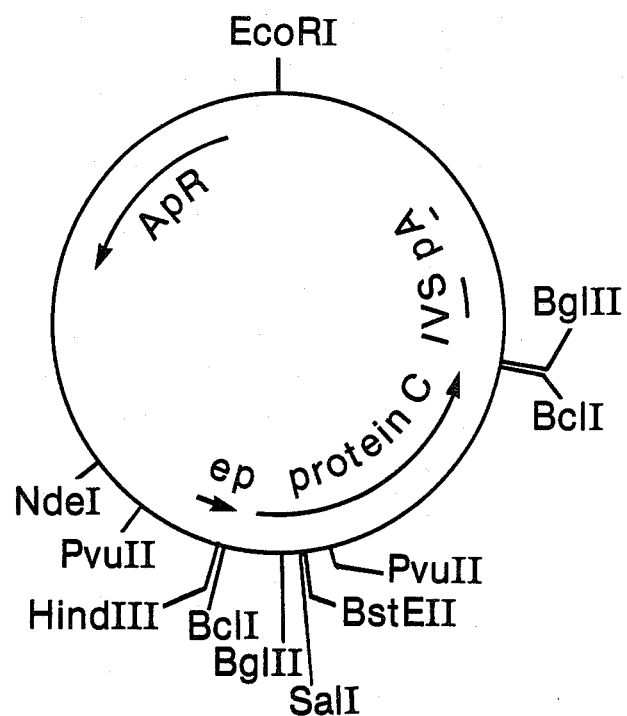
FIG. 3—the restriction site and function map of plasmid pL133.

Two μl of the fragment obtained in Example 3A, 2 μl of the fragment obtained in Example 3B, and 2 μl of the fragment obtained in Example 3C were mixed together and ligated in substantial accordance with the procedure of Example 2H. The ligated DNA constituted the desired plasmid pL133; a restriction site and function map of the plasmid is presented in FIG. 3 of the accompanying drawings.

E. Construction of E. coli K12 RR1/pL133

The desired E. coli K12 RR1/pL133 transformants were constructed in substantial accordance with the teaching of Example 2I, with the exception that plasmid pL133, rather than plasmid pSV2-HPC8, was used as the transforming DNA. Plasmid DNA was obtained from the E. coli K12 RR1/pL133 transformants in substantial accordance with the procedure of Example 1, except that the antibiotic used in culturing the cells was ampicillin, not tetracycline.

EXAMPLE 4
Construction of Plasmid pL132

A. Isolation of the ~5.7 kb HindIII-BglII Restriction Fragment of Plasmid pSV2-neo The isolation of the ~5.7 kb HindIII-BglII restriction fragment of plasmid pSV2-neo (ATCC 37149) was accomplished in substantial accordance with the teaching of Example 2G, with the exception that plasmid pSV2-neo, rather than plasmid pSV2-gpt, was used. The ~5 μg of DNA obtained were suspended in 10 μl of TE buffer and stored at −20° C.

B. Ligation of Fragments to Construct Plasmid pL132

Figure 4:
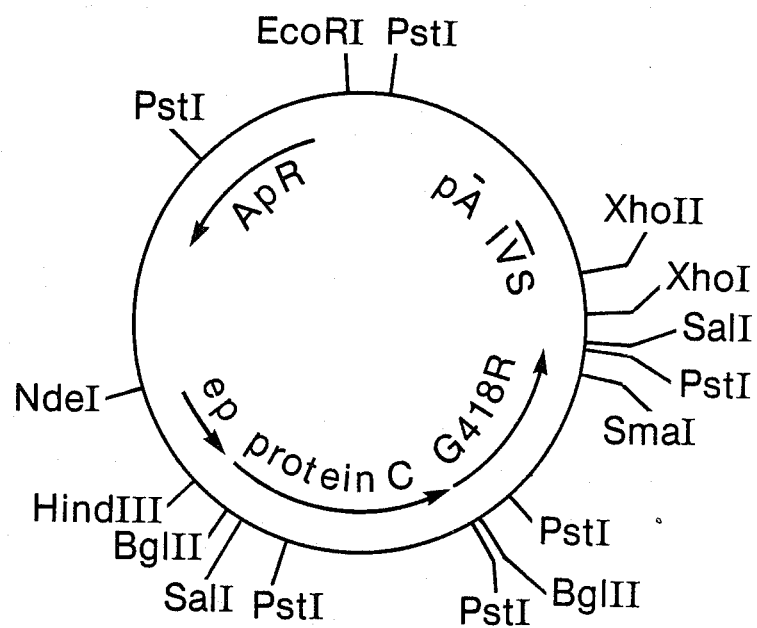
FIG. 4—the restriction site and function map of plasmid pL132.

Two μl of the ~5.7 kb HindIII-BglII restriction fragment of plasmid pSV2-neo (prepared in Example 4A), 2 μl of the ~0.29 kb HindIII-SalI restriction fragment of plasmid pSV2-HPC8 prepared in Example 3A, and 2 μl of the ~1.15 kb SalI-BglII restriction fragment of plasmid pSV2-HPC8 prepared in Example 3B were mixed together and ligated in substantial accordance with the procedure of Example 2H. The ligated DNA constituted the desired plasmid pL132; a restriction site and function map of the plasmid is presented in FIG. 4 of the accompanying drawings.

C. Construction of E. coli K12 RR1/pL132

The desired E. coli K12 RR1/pL132 transformants were constructed in substantial accordance with the teaching of Example 2I, with the exception that plasmid pL132, rather than plasmid pSV2-HPC8, was used as the transforming DNA. Plasmid DNA was obtained from the E. coli K12 RR1/pL132 transformants in substantial accordance with the procedure of Example 1, except that the antibiotic used in culturing the cells was ampicillin, not tetracycline.

EXAMPLE 5
Construction of Plasmid pL141

A. Construction of an XhoI Recognition Sequence on Plasmid pSV2-dhfr to Yield Plasmid pSV2-dhfr-X Ten μg of plasmid pSV2-dhfr (isolated from E. coli K12 HB101/pSV2-dhfr, ATCC 37146) were mixed with 10 μl 10× BamHI salts, 2 μl (~20 units) restriction enzyme BamHI, and 88 μl of H₂O, and the resulting reaction was incubated at 37° C. for two hours. The reaction was terminated by phenol and chloroform extractions, after which the BamHI-digested plasmid pSV2-dhfr DNA was precipitated and collected by centrifugation.

The DNA pellet was resuspended in 1 μl of 50 mM DTT, 4 μl of a solution 100 mM in each of the dNTPs, 1 μl of the Klenow fragment of DNA polymerase I (~5 units, New England Biolabs), 34 μl of H₂O, and 5 μl of 10× Klenow buffer (400 mM KPO₄, pH=7.5; 66 mM MgCl₂; and 10 mM 2-mercaptoethanol) and incubated at 14° C. for one hour. The reaction was stopped by the addition of 4 μl of 0.25M EDTA and a subsequent phenol extraction. The DNA was precipitated from the reaction mix and pelleted by centrifugation. The ~10 μg of DNA obtained were dissolved in 20 μl of TE buffer.

XhoI linkers (New England Biolabs, 32 Tozer Road, Beverly, MA 09195) of sequence:

were kinased and prepared for ligation by the following procedure. Four μl of linkers (~2 μg) were dissolved in 20.15 μl of H₂O and 5 μl of 10× kinase buffer (500 mM Tris-HCl, pH=7.6 and 100 mM MgCl₂), incubated at 90° C. for two minutes, and then cooled to room temperature. Five μl of γ-³²P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01 mM ATP and 5 more μl of kinase were added, and the reaction was continued for another 30 minutes at 37° C. The reaction was then stored at −20° C.

Six and eight-tenths μl (~3.4 μg) of the BamHI-digested, Klenow-treated, plasmid pSV2-dhfr and 10 μl (~0.4 μg) of the kinased XhoI linkers were mixed and incubated with 11.3 μl of water, 3.5 μl 10× ligase buffer, 1.4 μl 10 mM ATP, and 2 μl T4 DNA ligase (~10 units) at 16° C. overnight. The reaction was stopped by a 10 minute incubation at 65° C.

Ten μl 10× XhoI reaction buffer (1.5M NaCl; 60 mM Tris-HCl, pH=7.9; 60 mM MgCl₂; 60 mM 2-mercaptoethanol; and 1 mg/ml BSA), 5 μl restriction enzyme XhoI (~100 units), and 50 μl of H₂O were added to the reaction, which was then incubated at 37° C. for four hours. The reaction was loaded onto a 1% agarose gel, and the desired fragment was isolated in substantial accordance with the teaching of Example 2G. The ~2 μg of fragment obtained were suspended in 10 μl of TE buffer.

The BamHI-digested plasmid pSV2-dhfr with XhoI linkers attached was then ligated and transformed into E. coli K12 RR1 in substantial accordance with the teaching of Examples 2H and 2I, with the exception that the transforming DNA was plasmid pSV2-dhfr-X.

The resulting E. coli K12 RR1/pSV2-dhfr-X transformants were identified by their ampicillin-resistant phenotype and by restriction enzyme analysis of their plasmid DNA. Plasmid pSV2-dhfr-X was isolated from the transformants in substantial accordance with the procedure of Example 1, except that ampicillin was the antibiotic used during the culturing of the cells.

B. Isolation of the ~4.2 kb EcoRI-XhoI Restriction Fragment of Plasmid pSV2-dhfr-X Fifty μg of plasmid pSV2-dhfr-X were mixed with 10 μl 10× XhoI reaction buffer, 5 μl (~50 units) restriction enzyme XhoI; and 85 μl of H₂O, and the resulting reaction was incubated at 37° C. for two hours. After the reaction, the XhoI-digested plasmid pSV2-dhfr-X DNA was precipitated and collected by centrifugation. The DNA pellet was resuspended in 10 μl 10× EcoRI reaction buffer, 5 μl (~50 units) restriction enzyme EcoRI, and 85 μl of H₂O, and the resulting reaction was incubated at 37° C. for two hours. After the EcoRI reaction, the XhoI-EcoRI-digested plasmid pSV2-dhfr-X DNA was loaded onto a 1% agarose gel, and the desired ~4.2 kb EcoRI-XhoI restriction fragment was purified in substantial accordance with the procedure of Example 2G. The ~10 μg of the fragment obtained were suspended in 20 μl of TE buffer and stored at 20° C.

C. Construction of the XhoI-BstEII Restriction Fragment from the ~0.64 kb PvuII-BstEII Restriction Fragment of Plasmid pL133

Fifty μg of plasmid pL133 were mixed with 10 μl 10× PvuII reaction buffer (600 mM NaCl; 60 mM Tris-HCl, pH=7.5; 60 mM MgCl₂; 60 mM 2-mercaptoethanol; and 1 mg/ml BSA), 5 μl (~50 units) restriction enzyme PvuII, and 85 μl of H₂O, and the resulting reaction was incubated at 37° C. for two hours. After the reaction, the PvuII-digested plasmid pL133 DNA was precipitated and collected by centrifugation.

Approximately 5 μg of XhoI linker, the same as that used in Example 5A, were kinased and ligated to the PvuII-digested plasmid pL133 DNA in substantial accordance with the teaching of Example 5A. After the ligation reaction, the DNA was precipitated and collected by centrifugation.

The DNA pellet was resuspended in 20 μl 10× XhoI reaction buffer, 10 μl (~100 units) restriction enzyme XhoI, and 165 μl of H₂O, and the resulting reaction was incubated at 37° C. for 4 hours. Then, 5 μl (~50 units) of restriction enzyme BstEII were added to the reaction, which was then incubated at 60° C. for 4 hours under mineral oil. The XhoI-BstEII-digested DNA was loaded onto a 3.5% polyacylamide gel, and the desired ~0.64 kb XhoI-BstEII restriction fragment was purified in substantial accordance with the teaching of Example 2A. Approximately 3 μg of the fragment were obtained, resuspended in 6 μl of TE buffer, and stored at −20° C.

D. Isolation of the ~2.7 kb EcoRI-BstEII Restriction Fragment of Plasmid pL133

Fifty μg of plasmid pL133 were mixed with 10 μl 10× BstEII reaction buffer, 5 μl (~50 units) restriction enzyme BstEII, and 85 μl of H₂O, and the resulting reaction was incubated at 60° C. for two hours under mineral oil. After the reaction, the BstEII-digested plasmid pL133 DNA was precipitated and collected by centrifugation. The DNA pellet was resuspended in 10 μl 10× EcoRI reaction buffer, 5 μl (~50 units) restriction enzyme EcoRI, and 85 μl of H₂O, and the resulting reaction was incubated at 37° C. for two hours. After the EcoRI reaction, the BstEII-EcoRI-digested plasmid pL133 DNA was loaded onto a 1% agarose gel, and the desired ~2.7 kb EcoRI-BstEII restriction fragment was purified in substantial accordance with the procedure of Example 2G. The ~10 μg of the fragment obtained were suspended in 20 μl of TE buffer and stored at 20° C.

E. Ligation of Fragments to Construct Plasmid pL141 and Transformation of E. coli K12 RR1

Figure 5:
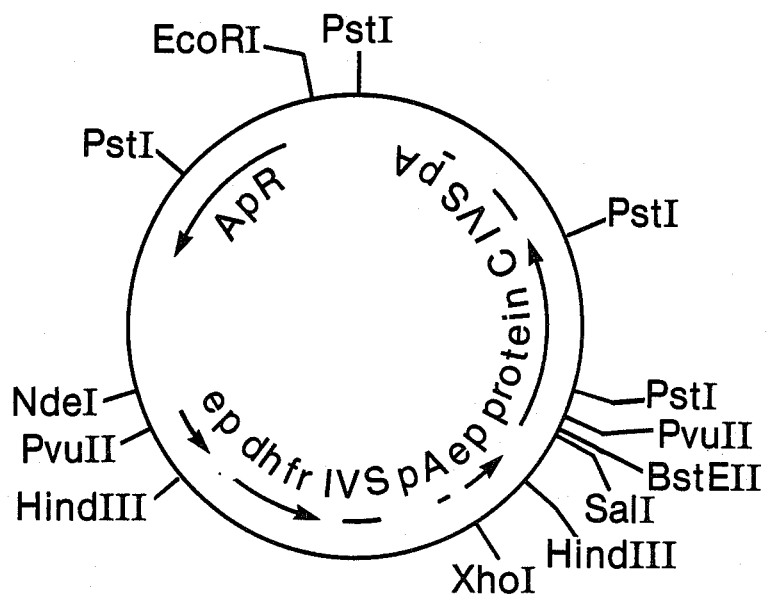
FIG. 5—the restriction site and function map of plasmid pL141.

Two μl of the ~4.2 kb ECoRI-XhoI restriction fragment of plasmid pSV2-dhfr-X prepared in Example 5B, 2 μl of the ~0.64 kb XhoI-BstEII restriction fragment constructed from plasmid pL133 in Example 5C, and 2 μl of the ~2.7 kb EcoRI-BstEII restriction fragment of plasmid pL133 prepared in Example 5D were mixed together, ligated, and the resulting plasmid pL141 DNA used to transform *E. coli* K12 RR1 in substantial accordance with the teaching of Examples 2H and 2I. The desired *E. coli* K12 RR1/pL141 transformants were identified by their ampicillin-resistant phenotype and by restriction enzyme analysis of their plasmid DNA. Plasmid pL141 was isolated from the transformants in substantial accordance with the procedure of Example 1, except that ampicillin was the antibiotic used in culturing the cells. A restriction site and function map of plasmid pL141 is presented in FIG. 5 of the accompanying drawings.

EXAMPLE 6

Construction of Plasmid pL142

A. Isolation of the ~0.76 kb NdeI-GindIII Restriction Fragment of Plasmid pRSVcat Fifty μg of plasmid pRSVcat (available from the ATCC in host *E. coli* HB110 under accession number ATCC 37152) were mixed with 10 μl 10× HindIII reaction buffer, 5 μl (~50 units) restriction enzyme HindIII, and 85 μl of $H_2O$, and the resulting digest was incubated at 37° C. for 2 hours. After the HindIII digestion, the DNA was precipitated and collected by centrifugation. The DNA pellet was dissolved in 10 μl 10× NdeI reaction buffer (1.5M NaCl; 100 mM Tris-HCl, pH=7.8; 70 mM $MgCl_2$; and 60 mM 2-mercaptoethanol), 10 μl (~30 units) restriction enzyme NdeI, and 85 μl of $H_2O$, and the resulting reaction was incubated at 37° C. until the digestion was complete.

The HindIII-NdeI-digested plasmid pRSVcat DNA was loaded onto a 3.5% polyacrylamide gel, and the ~0.76 kb NdeI-HindIII restriction fragment was isolated and purified in substantial accordance with the teaching of Example 2A. Approximately 5 μg of the fragment were obtained, suspended in 10 μl of TE buffer, and stored at −20° C. The fragment comprises the promoter activity of the long terminal repeat from Rous Sarcoma virus and functions as a promoter of DNA transcription in many eukaryotic cells.

B. Isolation of the ~5.1 kb NdeI-HindIII Restriction Fragment of Plasmid pL133

The isolation was accomplished in substantial accordance with the teaching of Example 6A, except that plasmid pL133, instead of plasmid pRSVcat, was digested. Furthermore the fragment was isolated from a 1% agarose gel, in substantial accordance with the teaching of Example 2G, instead of a 3.5% polyacrylamide gel. Approximately 5 μg of the desired fragment were obtained, suspended in 10 μl of TE buffer, and stored at −20° C.

C. Ligation of Fragments to Construct Plasmid pL142 and Transformation of *E. coli* K12 RR1

Figure 6:
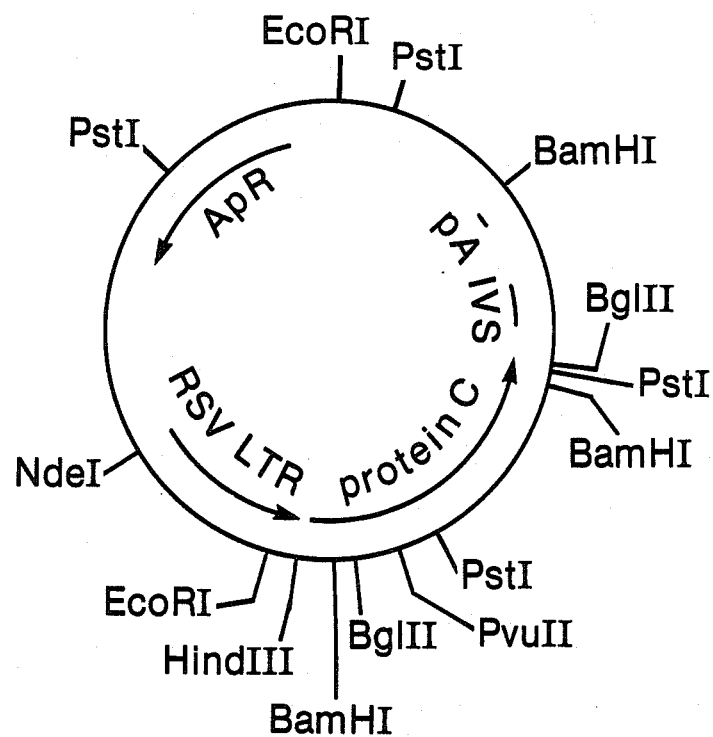
FIG. 6—the restriction site and function map of plasmid pL142.

Two μl of the ~0.76 kb NdeI-HindIII restriction fragment of plasmid pRSVcat isolated in Example 6A were ligated to 1 μl of the ~5.1 kb NdeI-HindIII restriction fragment of plasmid pL1 33 isolated in Example 6B. The ligation was carried out in substantial accordance with the teaching of Example 2H. The ligated DNA, constituting the desired plasmid pL142, was used to transform *E. coli* K12 RR1 in substantial accordance with the teaching of Example 2I. The *E. coli* K12 RR1/pL142 transformants were identified by their ampicillin-resistant phenotype and by restriction enzyme analysis of their plasmid DNA. A restriction site and function map of plasmid pL142 is presented in FIG. 6 of the accompanying drawings. Plasmid pL142 was isolated from the transformants in substantial accordance with the teaching of Example 1, with the exception that ampicillin was the antibiotic used in culturing the cells.

EXAMPLE 7

Construction of Plasmid pMSV-HPC

Ten μg of plasmid pMSVi (NRRL B-15929) were dissolved in 10 μl 10× BglII buffer, 2 μl (~20 units) restriction enzyme BglII, and 88 μl of $H_2O$, and the resulting reaction was incubated at 37° C. for 2 hours. After extracting the BglII-digested plasmid pMSVi DNA with both phenol and chloroform, the DNA was resuspended in 10 μl of $H_2O$.

Two μl of the BglII-digested plasmid pMSVi DNA were mixed with 2 μl of the ~1.425 kb BclI restriction fragment of plamid pSV2-HPC8 prepared in Example 8C, below, and the two fragments were ligated and transformed into *E. coli* K12 RR1 in substantial accordance with the procedure of Examples 2H and 2I.

Figure 7:
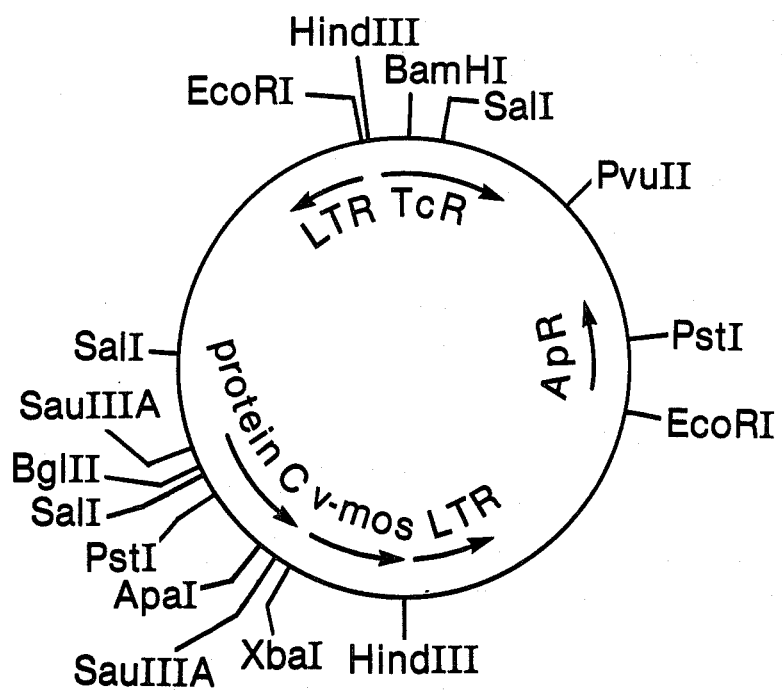
FIG. 7—the restriction site and function map of plasmid pMSV-HPC.

The desired pMSV-HPC transformants were identified by restriction enzyme analysis of their plasmid DNA and by their ampicillin-resistant and tetracycline-resistant phenotype. A restriction site and function map of plasmid pMSV-HPC is presented in FIG. 7 of the accompanying drawings. Due to the presence of the Murine Sarcoma virus sequences on the plasmid, plasmid pMSV-HPC can be encapsidated to become a transmissible vector with trans-acting functions provided by a helper virus with a broad host range (e.g., amphotropic murine leukemia viruses) or by a cell line harboring such helper functions. This process greatly enhances the transformability of the vector and widens the range of host cells wherein the vector can be expressed.

EXAMPLE 8

Construction of Plasmid pMMTΔBPV-HPC

A. Construction of Intermediate Plasmid pMMTΔBPV

About one μg of plasmid pdBPV-MMTneo (ATCC 37224) was mixed with 10 μl 10× BamHI reaction buffer, 5 μl (~50 units) restriction enzyme BamHI, and 85 μl of $H_2O$, and the resulting reaction was incubated at 37° C. for two hours.

After a five minute incubation at 65° C., the BamHI-digested plasmid pdBPV-MMTneo DNA was diluted to a concentration of about 0.1 μg/μl in ligase buffer and ligated with T4 DNA ligase, and the resulting plasmid pMMTAΔBPV DNA was used to transform *E. coli* K12 RR1 in substantial accordance with the teaching of Examples 2H and 2I. The *E. coli* K12 RR1/pMMTΔBPV transformants were identified by their ampicillin-resistant phenotype and by restriction enzyme analysis of their plasmid DNA. Plasmid pMMTΔBPV DNA was isolated from the transformants in substantial accordance with the teaching of Example 1, except that ampicillin was the antibiotic used during culturing of the cells.

B. Preparation of BglII-Digested Plasmid pMMTΔBPV

Ten μg of plasmid pMMTΔBPV DNA were dissolved in 10 μl 10× BglII buffer, 5 μl (~50 units) restriction enzyme BglII, and 85 μl of $H_2O$, and the resulting reaction was incubated at 37° C. for two hours. The reaction was then extracted once with phenol and once with chloroform, and the DNA was precipitated and collected by centrifugation. The ~10 μg of BglII-digested plasmid pMMTΔBPV DNA obtained by this procedure were suspended in 20 μl of TE buffer and stored at 20° C.

C. Isolation of the ~1.425 kb BclI Restriction Fragment of Plasmid pSV2-HPC8

In order to digest DNA completely with restriction enzyme BclI, the deoxyadenyl residue in the recognition sequence must not be methylated. When preparing plasmid DNA in *E. coli* for subsequent digestion with BclI, it is necessary to use a strain deficient in adenine methylase, such as *E. coli* K12 GM48 (NRRL B-15725).

*E. coli* K12 GM48 was prepared for transformation and then transformed with plasmid pSV2-HPC8 in substantial accordance with the procedure of Example 2I. Plasmid pSV2-HPC8 DNA was isolated from the *E. coli* K12 GM48/pSV2-HPC8 transformants in substantial accordance with the teaching of Example 1, except that ampicillin was the antibiotic used during culturing of the cells.

Fifty μg of the plasmid pSV2-HPC8 DNA isolated from the *E. coli* K12 GM48/pSV2-HPC8 transformants were dissolved in 10 μl 10× BclI reaction buffer (750 mM KCl; 60 mM Tris-HCl, pH=7.4; 100 mM MgCl₂; 10 mM dithiothreitol; and 1 mg/mL BSA), 5 μl (~50 units) restriction enzyme BclI, and 85 μl of H₂O, and the resulting reaction was incubated at 50° C. for two hours. The BclI-digested plasmid pSV2-HPC8 DNA was loaded onto a 1% agarose gel, and the desired ~1.425 kb BclI restriction fragment was isolated and purified in substantial accordance with the teaching of Example 2G. The ~5 μg of fragment obtained were dissolved in 10 μl of TE buffer and stored at −20° C.

D. Ligation to Construct Plasmid pMMTΔBPV-HPC and Transformation of *E. coli* K12 RR1

Figure 8:
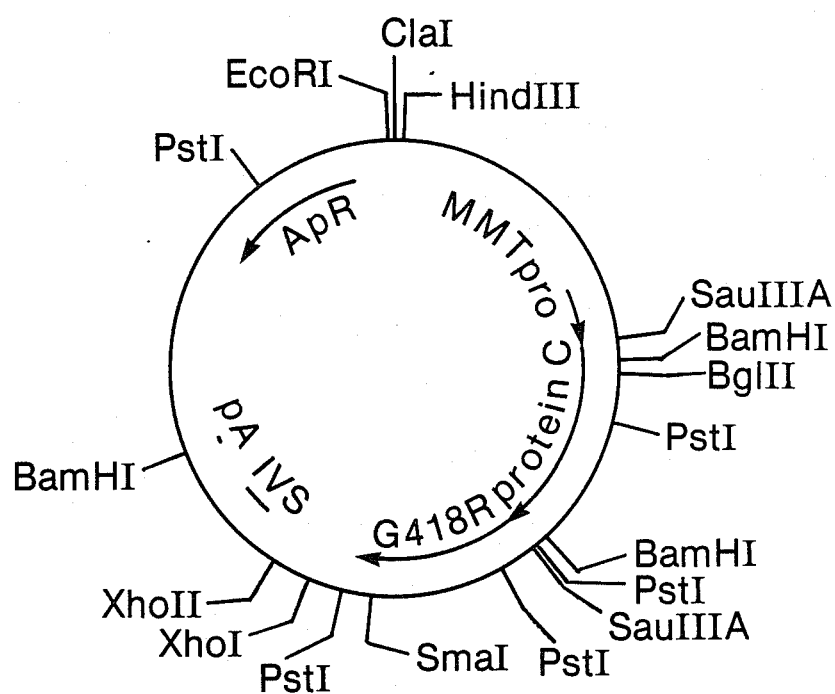
FIG. 8—the restriction site and function map of plasmid pMMTΔBPV-HPC.

Two μl of the BglII-digested plasmid pMMTΔBPV DNA prepared in Example 8B and 2 μl of the ~1.425 kb BclI restriction fragment of plasmid pSV2-HPC8 isolated in Example 8C were mixed together, ligated, and the resulting plasmid pMMTΔBPV-HPC DNA used to transform *E. coli* K12 RR1 in substantial accordance with the procedure of Examples 2H and 2I. The desired *E. coli* K12 RR1/pMMTΔBPV-HPC transformants were identified by their ampicillin-resistant phenotype and by restriction enzyme analysis of their plasmid DNA. Plasmid pMMTΔBPV-HPC was isolated from the transformants in substantial accordance with the procedure of Example 1, except that ampicillin was the antibiotic used during culturing. A restriction site and function map of plasmid pMMTΔBPV-HPC is presented in FIG. 8 of the accompanying drawings.

EXAMPLE 9

Construction of Plasmid pL151

A. Construction of an ~1.06 kb BstEII-XhoI Restriction Fragment Derived From Plasmid pL142

Fifty μg of plasmid pL142 DNA were dissolved in 10 μl 10× NdeI reaction buffer, 5 μl (~50 units) restriction enzyme NdeI, and 85 μl of H₂O, and the resulting reaction was placed at 37° C. for two hours. After the reaction, the DNA was precipitated and collected by centrifugation. The DNA pellet was resuspended in 65 μl Klenow buffer and the NdeI-digested DNA was treated with Klenow enzyme in substantial accordance with the procedure of Example 5A. After the Klenow reaction, the DNA was again precipitated and collected by centrifugation.

XhoI linkers (5′-CCTCGAGG-3′) were kinased, prepared for ligation, and ligated to the NdeI-digested, Klenow-treated plasmid pL142 DNA in substantial accordance with the procedure of Example 5A. After heat-inactivating the ligation reaction, the DNA was precipitated and collected by centrifugation.

The DNA pellet was dissolved in 20 μl 10× XhoI reaction buffer, 10 μl (~100 units) restriction enzyme XhoI, and 170 μl of H₂O, and the resulting reaction was incubated at 37° C. for two hours. Then, 5 μl (~50 units) restriction enzyme BstEII were added to the reaction, which was incubated at 60° C. for four hours under mineral oil. After phenol extraction, the digested DNA was loaded onto an acrylamide gel and the ~1.06 kb BstEII-XhoI restriction fragment was isolated and purified in substantial accordance with the procedure of Example 2A. Approximately 5 μg of the desired fragment were obtained, suspended in 10 μl of TE buffer, and stored at −20° C.

B. Ligation and Final Construction of Plasmid pL151 and *E. coli* K12 RR1/pL151

Two μl of the ~1.06 kb BstEII-XhoI restriction fragment derived from plasmid pL142 and prepared in Example 9A were ligated to 2 μl of the ~4.2 kb EcoRI-XhoI restriction fragment of plasmid pSV2-dhfr-X prepared in Example 5B, and to 2 μl of the ~2.74 kb BstEII-EcoRI restriction fragment of plasmid pL133 prepared in Example 5D. The ligation reaction was carried out in substantial accordance with the procedure of Example 2H.

Figure 9:
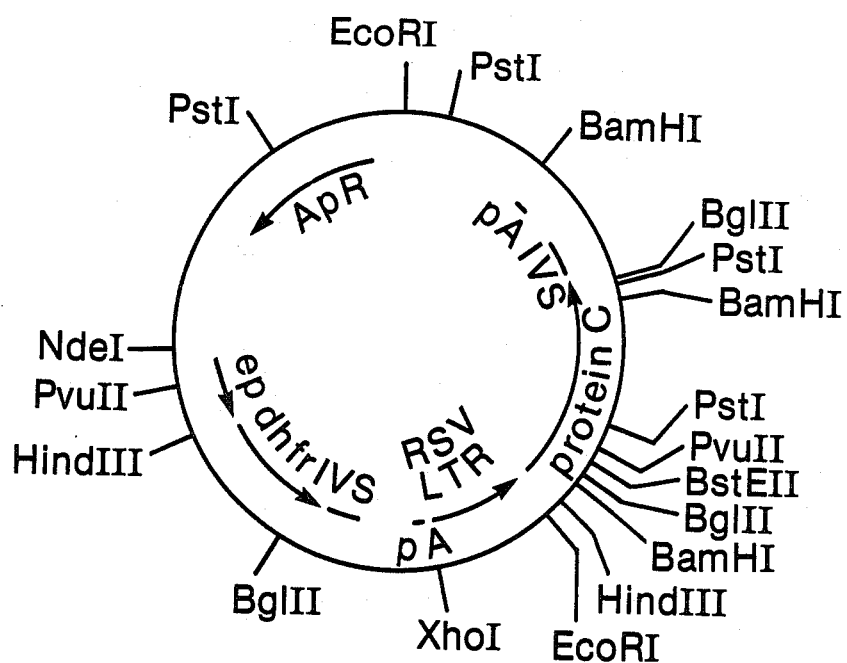
FIG. 9—the restriction site and function map of plasmid pL151.

The ligated DNA constituted the desired plasmid pL151 and was used to transform *E. coli* K12 RR1 in substantial accordance with the procedure of Example 2I. The desired *E. coli* K12 RR1/pL151 transformants were selected on ampicillin-containing media and identified by restriction enzyme analysis of their plasmid DNA. A restriction site and function map of plasmid pL151 is presented in FIG. 9 of the accompanying drawings.

EXAMPLE 10

Construction of Plasmid pNM789B

A. Construction of Plasmid pKEN021 and Isolation of the ~5.1 kb XbaI-BamHI Restriction Fragment The ~5.1 kb fragment produced by XbaI-BamHI cleavage of plasmid pKEN021 106 in FIG. 12) was used as starting material. Plasmid pKEN021 is a derivative of pKEN111 (101 in FIG. 10 and further described in Lee, et al., 1981, J. Bact. 146: 861–866 and Gwiebel, et al., 1981, J. Bact. 145: 654–656), which is on deposit in *E. coli* CC620 (NRRL B-15011) and which has a ~2.8 kb fragment which contains the lipoprotein gene of *E. coli*. A description of this fragment is provided in Nakamura and Inouye, 1979, Cell 18: 1109–1117.

In plasmid pKEN021, the 650 bp (base pair) sequence between the unique EcoRI and SalI restriction sites of pBR322 has been replaced by sequences taken from the lipoprotein gene of *E. coli*. The lipoprotein gene sequence (Nakamura and Inouye, 1979) includes a 462 bp AluI fragment, upstream from the first triplet (ATG) of the lipoprotein gene that contains the promoter, the 5′ untranslated region, and the ribosome-binding site. A unique XbaI restriction site is located within the ribosome-binding site 16 bp before the translation-initiating, methionine-encoding signal. A PvuII restriction site located 105 bp upstream from the translation termination codon of the structural gene was changed to a BamHI restriction site by the addition of a synthetic DNA linker (5'CCGGATCCGG3', obtained from Collaborative Research). The coding sequence for the last 35 amino acids of lipoprotein, the translation termination signal, and the sequence corresponding to the 3' untranslated region of the messenger RNA follow the BamHI site. Plasmid pKEN021 also includes some 850 bp of extraneous sequences unrelated to the lipoprotein gene and located downstream of it in the *E. coli* chromosome. These sequences were included as a consequence of the methods and restriction enzyme sites used in the original isolation of the gene.

Figure 10:
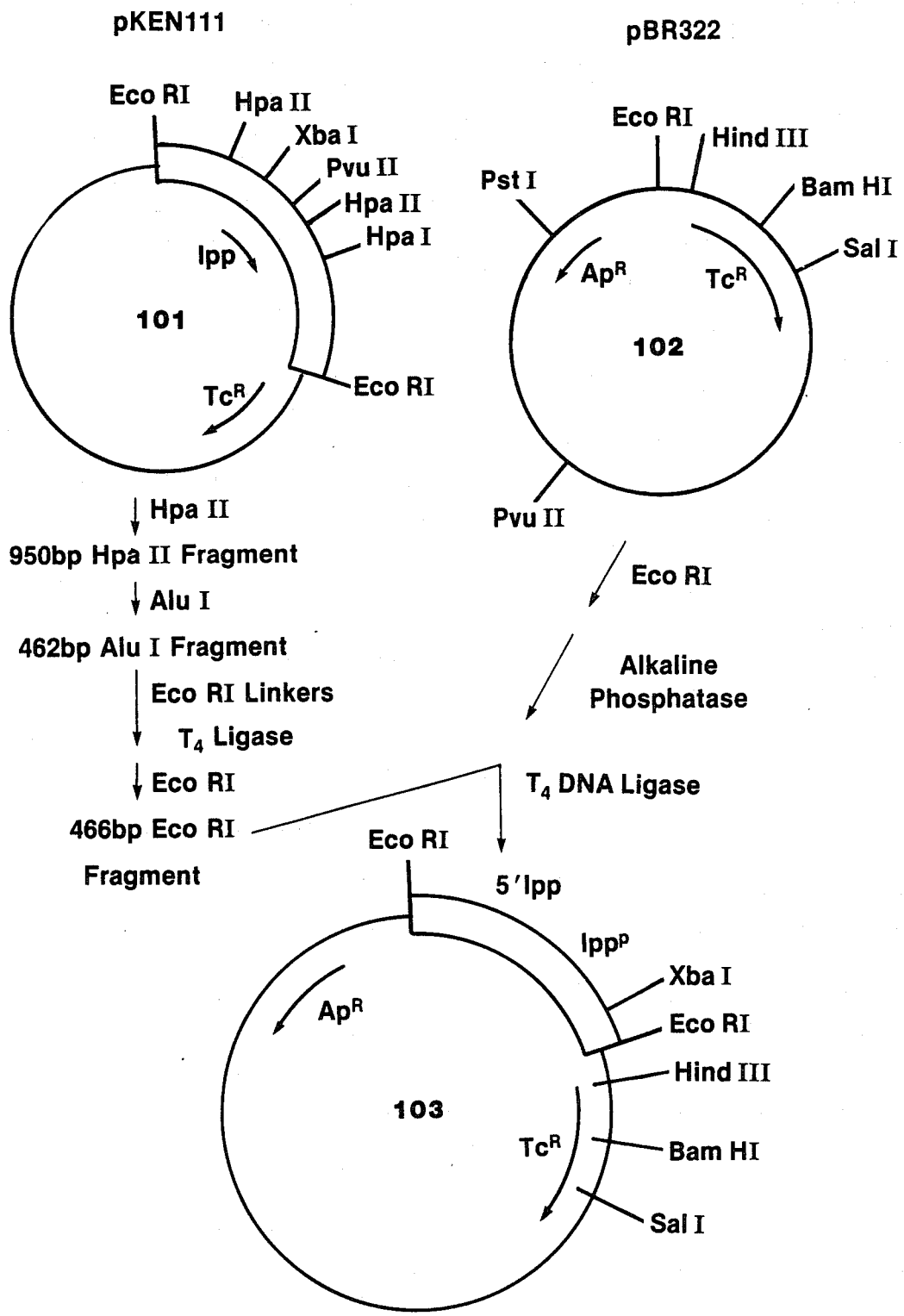
Figure 11:
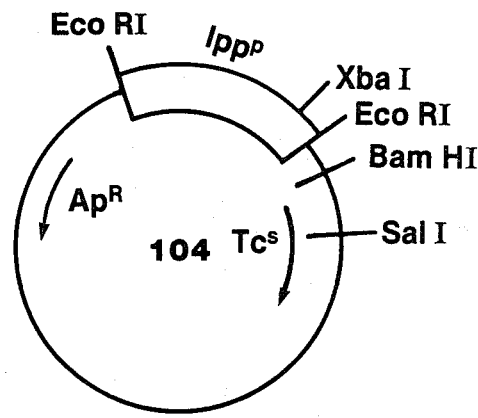
Figure 11:
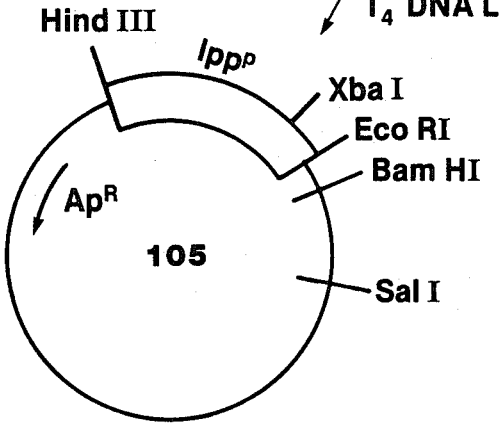

Referring to FIGS. 10, 11, and 12, plasmid pKEN021 is derived from pKEN111 in the following manner: About 50 μg of plasmid pKEN111 (101 in FIG. 10) are digested with 25 units of HpaII restriction enzyme in 300 μl of a buffer containing 20 mM Tris·HCl, pH 7.4; 10 mM MgCl$_2$; 6 mM KCl; and 1 mM dithiothreitol at 37° C. for 2 hours. The mixture is extracted twice with 300 μl of a 50:50 mixture of phenol and chloroform and the recovered aqueous phase is then precipitated, after chilling to −70° C., with 2.5 volumes of ethanol and 0.1 volume of 3M sodium acetate. The DNA pellet is dissolved in 100 μl of electrophoresis buffer and fractionated on a 5 percent polyacrylamide gel (acrylamide:bis ratio is 29:1 in all gels except where noted). The gel is stained in a solution containing 0.5 μg/ml of ethidium bromide and bands are visualized under long wavelength ultraviolet light. A 950 bp band is isolated and recovered from the gel by electroelution into a dialysis bag. After phenol/CHCl$_3$ extraction and ethanol precipitation, the recovered DNA (approximately 2.5 μg) is dissolved in 25 μl of TEN (10 mM NaCl; 10 mM Tris·HCl, pH 7.4; and 1 mM sodium ethylenedinitrilotetraacetate (EDTA), pH 8.0).

About 2 μg of the 950 bp HpaII fragment are digested with AluI restriction enzyme in 200 μl of a buffer containing 50 mM NaCl, 6 mM Tris HCl (pH 7.6), 6 mM MgCl$_2$, and 6 mM β-mercaptoethanol for 2 hours at 37° C. The DNA is fractionated on a 6 percent polyacrylamide gel and the 462 bp AluI fragment generated is recovered and purified by the method previously described. The 462 bp AluI fragment (approximately 1 μg) is dissolved in 10 μl of T4 DNA ligase buffer (50 mM Tris·HCl, pH 7.8; 10 mM MgCl$_2$; 20 mM dithiothreitol; and 1.0 mM ATP) containing 150 picomoles of phosphorylated EcoRI linker (5'GGAATTCC3' from Collaborative Research) and 2 units T4 DNA ligase. After incubation at 4° C. for 16 hours, the mixture is heated at 65° C. for 10 minutes and diluted to 100 μl with the addition of EcoRI buffer (100 mM Tris HCl, pH 7.5; 50 mM NaCl; 5 mM MgCl$_2$; and 6 mM β-mercaptoethanol) and 40 units EcoRI enzyme. After 2 hours at 37° C., the sample is conventionally phenol/CHCl$_3$ extracted and ethanol precipitated.

The DNA is then dissolved in 20 μl of T4 DNA ligase buffer containing 1 unit T4 DNA ligase and 0.1 μg pBR322 (102 in FIG. 10) which has been linearized with EcoRI and then treated with alkaline phosphatase. After ligation at 4° C. for 16 hours, the resultant DNA is used to conventionally transform *E coli* K12 RV308 (NRRL B-15624). Transformants are selected on agar plates containing 12 μg/ml of tetracycline and plasmids isolated from resistant colonies by the rapid alkaline extraction procedure described in Birnboim and Doly, 1979, Nucleic Acids Research 7: 1513–1523. A plasmid (103 in FIG. 10) containing a 466 bp XbaI-BamHI fragment is selected and used as the starting material for the step next described.

About two μg of this plasmid (103 in FIG. 11) are digested with 2 units of HindIII enzyme in 50 μl HindIII buffer (50 mM NaCl; 10 mM Tris·HCl, pH 8; 10 mM MgCl$_2$; and 6 mM β-mercaptoethanol) for 1 hour at 37° C. After phenol/CHCl$_3$ extraction and ethanol precipitation, the DNA is dissolved in 200 μl of a buffer containing 300 mM NaCl, 30 mM sodium acetate at pH 4.25, 1 mM ZnCl$_2$, and 200 units of S1 nuclease (Miles Laboratories). After 1 hour at 15° C., the reaction is stopped by phenol/CHCl$_3$ extraction and ethanol precipitation. The resultant DNA is dissolved in 10 μl T4 DNA ligase buffer containing 20 picomoles phosphorylated BamHI linkers (5'CCGGATCCGG3', from Collaborative Research) and 2 units T4 DNA ligase. After 16 hours at 4° C., the reaction mixture is heated at 65° C. for 10 minutes to inactivate the ligase and then diluted to 100 μl in BamHI buffer (150 mM NaCl; 6 mM Tris·HCl, pH 8.0; 6 mM MgCl$_2$; and 6 mM β-mercaptoethanol) containing 20 units BamHI enzyme. After 2 hours at 37° C., the mixture is purified on a 1 percent agarose gel.

The gel is stained and the larger fragment (~4.5 kb) is recovered by elution after freezing the gel and then purified by phenol/CHCl$_3$ extraction and ethanol precipitation. The recovered fragment with BamHI cohesive ends is dissolved in 20 μl of T4 DNA ligase buffer containing 1 unit T4 DNA ligase. After 16 hours at 4° C., the DNA is used to transform *E. coli* RV308. Transformants are selected by resistance to ampicillin (Ap$^r$) at 100 μg/ml and screened for sensitivity to 10 μg/ml tetracycline (Tc$^s$). Several plasmids, prepared by the previously described Birnboim procedure from colonies which are Ap$^r$Tc$^s$, are examined for the absence of a HindIII site and the presence of a single BamHI site. EcoRI and SalI sequential digestion yields a 466 bp and a 305 bp fragment. A plasmid (104 in FIG. 11) with these characteristics is selected and then modified to convert the EcoRI site, located upstream of the lpp promoter, to a HindIII restriction site.

Two micrograms of plasmid (104 in FIG. 11) are digested in 100 μl of EcoRI buffer with 0.2 units of EcoRI for 10 minutes at 37° C. The reaction is stopped by heating for 10 minutes at 65° C., and, after phenol/CHCl$_3$ extraction, the DNA is ethanol precipitated, dissolved in 200 μl of S1 nuclease buffer containing S1 nuclease at 1000 units/ml, and reacted at 12° C. for 1 hour. The reaction is stopped by phenol/CHCl$_3$ extraction and ethanol precipitation. The resultant DNA is resuspended in 10 μl of T4 DNA ligase buffer containing 20 picomoles phosphorylated HindIII linker (5'CCAAGCTTGG3', from Collaborative Research) and 2 units of T4 DNA ligase. After 16 hours at 4° C., the mixture is heated for 10 minutes at 65° C., diluted to 150 μl in HindIII buffer containing 10 units HindIII enzyme, incubated for 2 hours at 37° C., and then fractionated on a 1 percent agarose gel. The largest band (equivalent to singly-cut plasmid) is conventionally recovered and purified, dissolved in 20 μl T4 ligase buffer containing 2 units T4 ligase, incubated 16 hours at 4° C., and then used to transform *E. coli* RV308. Transformants are selected for ampicillin resistance and plasmid isolates conventionally analyzed by restriction enzyme analysis. A plasmid (105 in FIG. 11) with an EcoRI-HindIII fragment of 466 bp is selected and used as the cloning vector for addition of the 3' region of the lpp gene.

About two μg of plasmid (105 in FIG. 12) are digested in 50 μl of SalI restriction buffer (150 mM NaCl; 6 mM Tris·HCl, pH 7.9; 6 mM MgCl$_2$; and 6 mM β-mercaptoethanol) with 2 units of SalI for 1 hour at 37° C. and then diluted to 150 μl in BamHI buffer containing 2 units BamHI. After 1 hour at 37° C., 2.5 units of alkaline phosphatase are added and incubation continued for 1 hour at 65° C. The material is phenol/CHCl$_3$ extracted, ethanol precipitated, dissolved in TEN, and used as a cloning vector for the lpp 3' fragment.

To obtain the fragment containing the lpp 3' region, 10 μg of pKEN111 (101 in FIG. 12) are digested in 200 μl of HpaI buffer (20 mM KCl; 10 mM Tris·HCl, pH 7.4; 10 mM MgCl$_2$; and 6 mM β-mercaptoethanol) with 10 units of HpaI for 2 hours at 37° C. After phenol/CHCl$_3$ extraction and ethanol precipitation, the DNA is dissolved in 10 μl T4 DNA ligase buffer containing 20 picomoles phosphorylated SalI linker (5'GGTCGACC3', from Collaborative Research) and 2 units T4 DNA ligase and then incubated for 16 hours at 4° C. The ligase is inactivated by heating at 65° C. for 10 minutes. The resultant material is diluted to 100 μl in SalI buffer containing 10 units of SalI and incubated 1 hour at 37° C., and then diluted to 300 μl in PvuII buffer (60 mM NaCl; 6 mM Tris·HCl, pH 7.5; 6 mM MgCl$_2$; and 6 mM β-mercaptoethanol) containing 10 units PvuII restriction enzyme. After 1 hour at 37° C., the DNA is fractionated on a 5 percent polyacrylamide gel.

Approximately 0.5 μg of a 950 bp fragment is recovered, purified, and dissolved in TEN. Two-tenths microgram of the fragment is diluted into 20 μl T4 DNA ligase buffer containing 20 picomoles phosphorylated BamHI linker (5'CCGGATCCGG3', from Collaborative Research) and 2 units T4 DNA ligase and then incubated for 16 hours at 4° C. The resultant DNA is then heated for 10 minutes at 65° C., diluted to 100 μl in BamHI buffer containing 20 units BamHI, incubated at 37° C. for 2 hours, and then fractionated on a 5 percent polyacrylamide gel to remove excess linker molecules. The resultant 950 bp fragment having BamHI and SalI cohesive ends is conventionally purified and dissolved in 20 μl of T4 DNA ligase buffer containing both 0.2 μg of the BamHI-SalI-digested, alkaline phosphatase-treated plasmid 105 DNA and 2 units T4 DNA ligase. After incubation for 16 hours at 4° C., the DNA is used to transform *E. coli* K12 RV308. Plasmids are prepared from ampicillin resistant transformants and conventionally analyzed for the SalI-BamHI fragment. The desired plasmid (~5.2 kb) is designated pKEN021 (106 in FIG. 12).

Ten micrograms of pKEN021 were digested at 37° C. in 200 μl of XbaI/BamHI buffer (150 mM NaCl; 10 mM Tris·HCl, pH 8; 10 mM MgCl$_2$; and 6 mM β-mercaptoethanol) using 10 units of BamHI for 1 hour followed by 10 units of XbaI for an additional hour at 37° C. The desired XbaI-BamHI-digested DNA was then treated with 2.5 units of alkaline phosphatase for 1.5 hours at 65° C., phenol/CHCl$_3$ extracted, collected by ethanol precipitation, and dissolved in 50 μl of TEN for future use (107 in FIG. 12).

B. Construction of Plasmid pNM575

Figure 13:
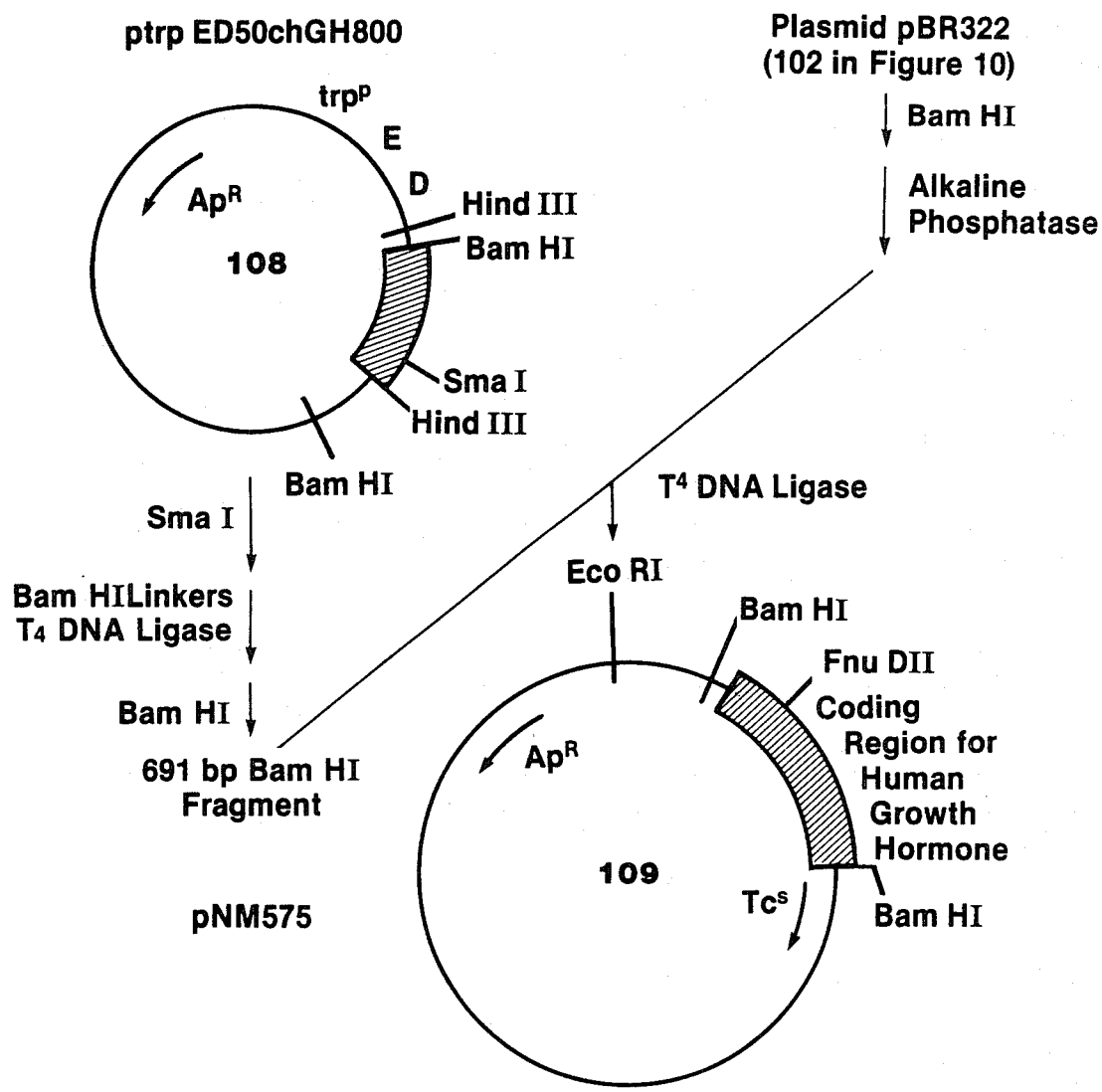

Plasmid ptrpED50chGH800 (108 in FIG. 13), described in Martial et al., 1979, Science 205: 602–607 was used as the source of a DNA fragment containing the coding sequence for a portion of the human growth hormone gene. This fragment can also be constructed synthetically (Itakura et al., 1977 and Crea et al., 1978) or can be obtained using recognized methodology described by Goodman et al., 1979, Methods in Enzymology 68:75–90, by isolating mRNA coding for human growth hormone from human pituitaries.

The human growth hormone gene portion of plasmid ptrpED50chGH800 contains a unique SmaI restriction site 6 bp downstream from the translation termination codon of the gene. This site was changed to a BamHI site using the following procedure: 6 μg of the plasmid were digested with 6 units of SmaI in 200 μl of SmaI restriction buffer (6 mM Tris·HCl, pH 8.0; 6 mM MgCl$_2$; 20 mM KCl; and 6 mM β-mercaptoethanol) for 1.5 at 37° C. After digestion was complete, phenol/CHCl$_3$ extraction was performed, and the DNA was recovered by ethanol precipitation and then dissolved in 24 μl of TEN. Forty picomoles of phosphorylated BamHI adapter fragment (Collaborative Research) were added to 0.5 μg (0.2 picomole ends) of the above-digested plasmid in 16 μl of ligase buffer containing 2 units T4 DNA ligase. The mixture was incubated 2 hours at 22° C., 16 hours at 4° C., and then 10 minutes at 65° C. BamHI cohesive termini were generated by conventional digestion with BamHI restriction enzyme.

The enzyme cleaved the linker sequence as well as the BamHI site located at the beginning of the cloned human growth hormone cDNA sequence. This cleavage yielded a 691 bp fragment with cohesive BamHI ends which was separated on a 6 percent polyacrylamide gel and then conventionally recovered. The recovered DNA fragment was ligated (using 2 units T4 DNA ligase in 20 μl of buffer under previously described conditions) with 0.2 μg of BamHI-digested and alkaline phosphatase-treated plasmid pBR322 (102 in FIG. 13). After 16 hours at 4° C., the material was used to transform *E. coli* strain JA221 (NRRL No. B-15014) in substantial accordance with the transformation procedure of Wensink et al., 1974, , Cell 3:315–325. Transformants were selected on agar plates containing 100 μg/ml ampicillin, and then plasmids were conventionally isolated and identified by restriction enzyme and gel electrophoretic analysis. Desired plasmids, designated as pNM575 (109 in FIG. 13), contain a BamHI fragment of approximately 700 bp and were conventionally amplified for future use.

Construction of Plasmid pNM702

The DNA sequence of mature human growth hormone contains one FnuDII site which is 47 bp from the first nucleotide of the coding sequence. Twenty-five micrograms of pNM575 were digested in 250 μl of BamHI buffer with 25 units of BamHI at 37° C. for 1 hour. The 691 bp fragment with BamHI cohesive termini was conventionally isolated from a 6 percent polyacrylamide gel and purified. After purification of the fragment, one-third of it (equivalent to 8 μg of plasmid) was digested in 100 μl of FnuDII buffer (6 mM NaCl; 6 mM Tris·HCl, pH 7.4; 6 mM MgCl$_2$; and 6 mM β-mercaptoethanol) with 2.5 units FnuDII for 1.5 hours at 37° C. Electrophoresis on a 6 percent polyacrylamide gel and standard recovery procedures were used to isolate a 538 bp DNA fragment containing the coding sequence for the last 175 amino acids of the gene followed by a translation stop signal.

Figure 14:
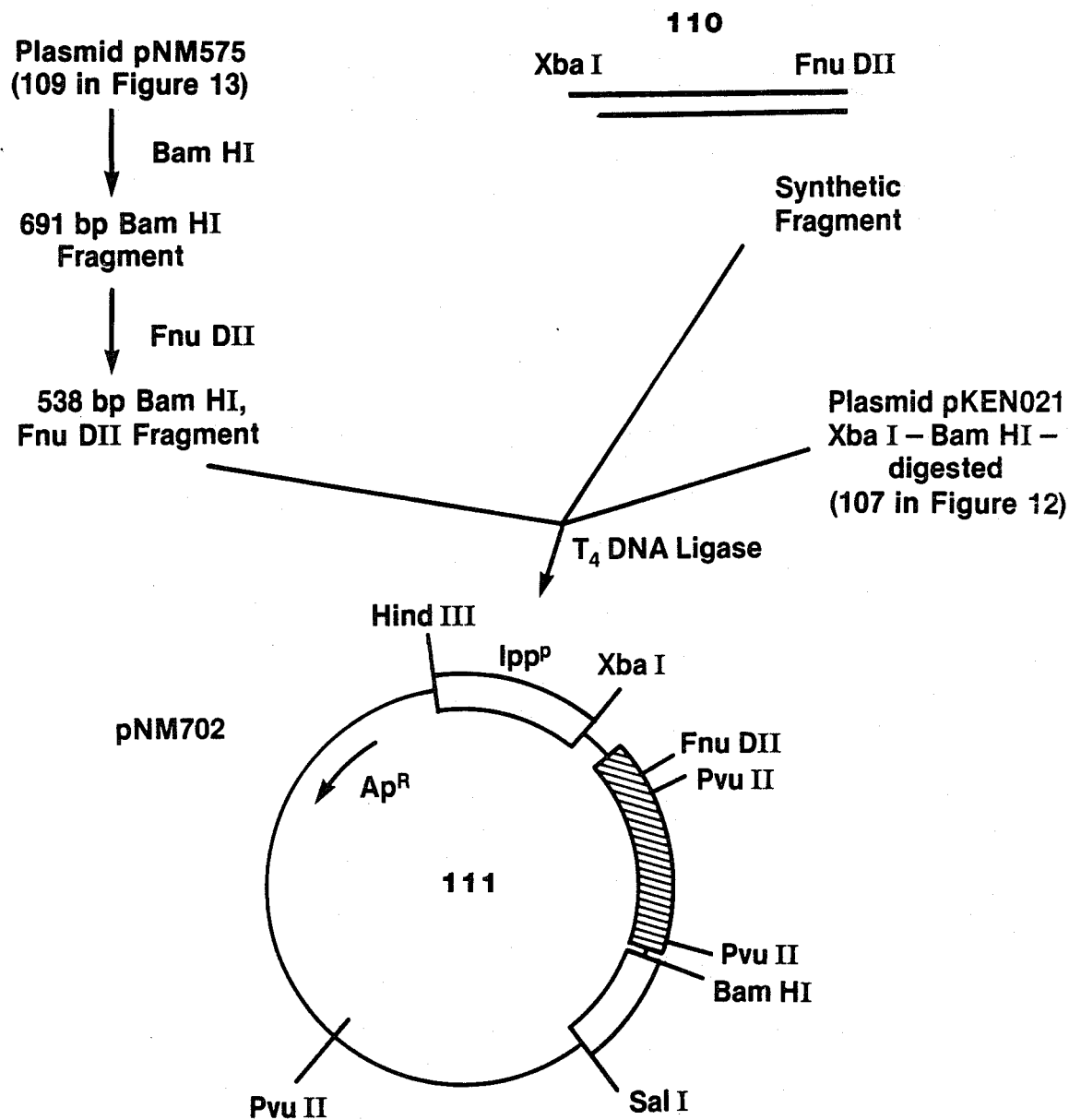

A double-stranded DNA fragment (110 in FIG. 14) was synthesized by the phosphotriester method to join the lpp promoter region with the human growth hormone coding region. The double-stranded DNA fragment (110 in FIG. 14) has the following sequence:

```
XBaI
    5'-CTAGAGGGTATTAATAATGTTCCC
       |||||||||||||||||||||||
    3'-    TCCCATAATTATTACAAGGG

ATTGGATGATGATGATAAGTTCCCA
       |||||||||||||||||||||||||
       TAACCTACTACTACTATTCAAGGGT

ACCATTCCCTTATCCAGGCTTTTTG
       |||||||||||||||||||||||||
       TGGTAAGGGAATAGGTCCGAAAAAC

FnuDII
       ACAACGCTATGCTCCG-3'
       ||||||||||||||||
       TGTTGCGATACGAGGC-5'
```

The fragment was prepared by ligating the following single-stranded DNA molecules, prepared by recognized phosphotriester methodology:
(1) CTAGAGGGTAT
(2) TAATAATGTTCC
(3) CATTGGATGAT
(4) GATGATAAGTTCC
(5) CAACCATTCCC
(6) TTATCCAGGC
(7) TTTTTGACAACG
(8) CTATGCTCCG
(9) CATTATTAATACCCT
(10) ATGGGAA
(11) CTTATCATCATCCA
(12) GGTTGGGAA
(13) GGATAAGGGAAT
(14) GTCAAAAAGCCT
(5) CGGAGCATAGCGTT Using the above-prepared segments, the T4 ligase catalyzed joining reactions were performed stepwise as described below:

(a) 5'-Unphosphorylated segment 1 was joined to 5-'phosphorylated segment 2 in the presence of 5'-phosphorylated segment 9 using T4 ligase to form DNA duplex 1 (Brown et al., 1979, Methods in Enzymology 109–151). The duplex was isolated by preparative gel electrophoresis on 15% polyacrylamide.

(b) 5'-Phosphorylated segment 3 was joined to 5'-phosphorylated segment 4 in the presence of 5'-phosphorylated segment 11 using T4 ligase to form DNA duplex 2 which was purified by 15% polyacrylamide gel electrophoresis.

(c) 5'-Phosphorylated segment 5 was joined to 5'-phosphorylated segment 6 in the presence of 5'phosphorylated segments 12 and 13 using T4 ligase to form DNA duplex 3 which was purified by 15% polyacrylamide gel electrophoresis.

(d) 5'-Phosphorylated segment 7 was joined to 5'-phosphorylated segment 8 in the presence of 5'-phosphorylated segment 14 and 5'-unphosphorylated segment 15 using T4 ligase to form DNA duplex 4 which was purified by 15% polyacrylamide gel electrophoresis.

(e) The DNA duplexes 2, 3 and 4 then were joined together by T4 ligase to form DNA duplex 5 which was purified by 15% polyacrylamide gel electrophoresis.

(f) 5'-phosphorylated segment 10 and DNA duplex 5 were added, in the presence of T4 ligase, to the DNA duplex 1. The resulting DNA duplex (110 in FIG. 5) was purified by 10% polyacrylamide gel electrophoresis. This DNA duplex then was enzymatically phosphorylated using T4 polynucleotide kinase and [γ-$^{32}$P]-ATP by following established procedure.

The expression plasmid pNM702 (111 in FIG. 14) was constructed by enzymatically joining 0.1 picomole (0.4 μg) of the XbaI-BamHI fragment of plasmid pKEN021 (107 in FIG. 14), 0.025 picomoles synthetic DNA fragment (110 in FIG. 14), and 0.3 picomoles (0.08 μg) of 538 bp fragment (from 109 in FIG. 14) in 24 μl of ligation buffer using 1.5 units T4 DNA ligase. After incubation for 16 hours at 4° C., the mixture was used to transform E. coli JA221 (NRRL B-15211) in the manner previously described. Transformants were selected on agar plates containing 100 μg/ml ampicillin and were conventionally cultured as a preferred source of the desired expression plasmid.

Expression of human growth hormone was detected by a standard radioimmunoassay procedure (Twomey et al., 1974, Clin. Chem. 20:389–391) and was determined to be at least 2 million molecules per cell.

D. Construction of Plasmid pNM789

Figure 15:
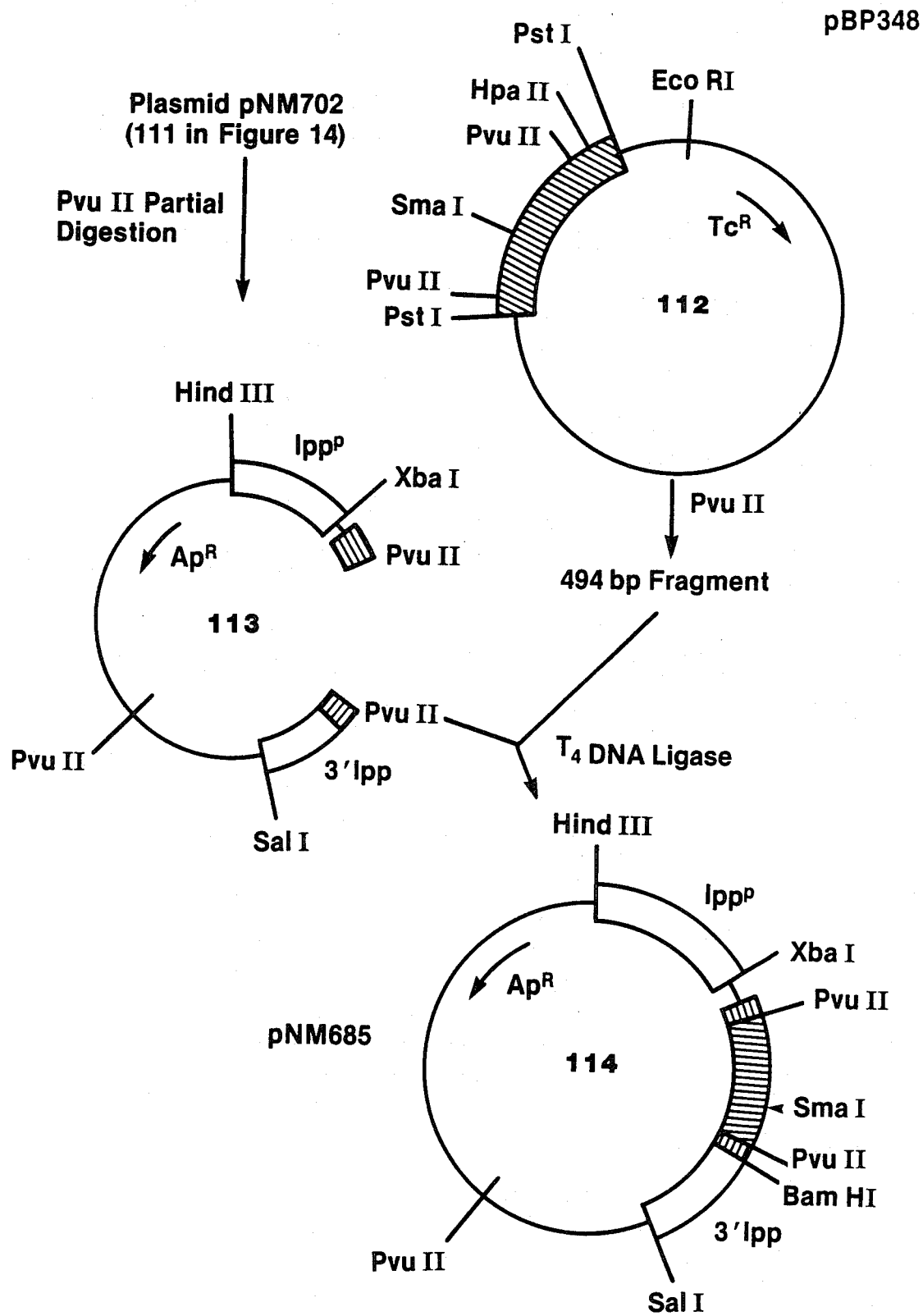

Plasmid pNM702 (111 in FIG. 15), the expression plasmid for huan growth hormone, was used as the starting material for construction of a plasmid expressing Met-Phe-Pro-Leu-Asp-Asp-Asp-Asp-Lys-bGH.

Plasmid pBP348 (112 in FIG. 15), described in Miller et al., 1980, J. Biol. Chem. 255:7521–7524, was used as the source of two DNA fragments containing the coding sequence for a portion of the bovine growth hormone gene. The plasmid contains an 831 bp. bovine growth hormone-encoding sequence cloned in the PstI restriction site of pBR322. As an alternative to the method described in Miller et al., 1980, the sequence for bovine growth hormone can be constructed synthetically (Itakura et al., 1977 and Crea et al., 1978) or can also be obtained from messenger RNA isolated from bovine pituitaries by the now routine procedures described by Goodman et al., 1979.

The coding sequences for human growth hormone and bovine growth hormone are very similar and show much homology. Particularly useful in the construction of the expression plasmid for bovine growth hormone were the fragments generated by digestion with the restriction enzyme PvuII. The size of the fragments produced are 497 bp in human growth hormone and 494 bp in bovine growth hormone and the corresponding restriction sites occur in the same reading frames in both sequences.

Ten micrograms of pNM702 (111 in FIG. 15) were partially digested with 1 unit of PvuII in 200 μl of PvuII restriction buffer for 10 minutes at 37° C. After the reaction was stopped by heating at 65° C. for 10 minutes, the DNA was treated with alkaline phosphatase and the fragments separated on a one percent agarose gel. The linear DNA fragment (113 in FIG. 15) of the size that corresponded to DNA with the 497 bp PvuII fragment missing (runs slightly faster than singly-cut plasmid) was conventionally excised, purified, and used in the construction of an intermediate plasmid (114 in FIG. 15).

A 494 bp PvuII fragment of plasmid pBP348 was prepared by digesting 10 μg of the plasmid in 200 μl PvuII buffer containing 10 units of PvuII for 1 hour at 37° C. The fragments were separated on a 6 percent polyacrylamide gel and the desired 494 bp fragment (from 112 in FIG. 15) was conventionally purified.

Intermediate plasmid (114 in FIG. 15) was constructed by reacting 0.2 μg of the plasmid pNM702 PvuII fragment with 0.05 μg of 494 bp fragment in 20 μl of T4 DNA ligase buffer containing 2 units T4 DNA ligase for 16 hours at 4° C. After transformation and selection of transformants for ampicillin resistance, the plasmids were conventionally analyzed for the presence and proper orientation of the 494 bp PvuII fragment. Plasmids with a 494 bp PvuII fragment and a 440 bp XbaI-SmaI fragment were selected for use in further constructions.

Figure 16:
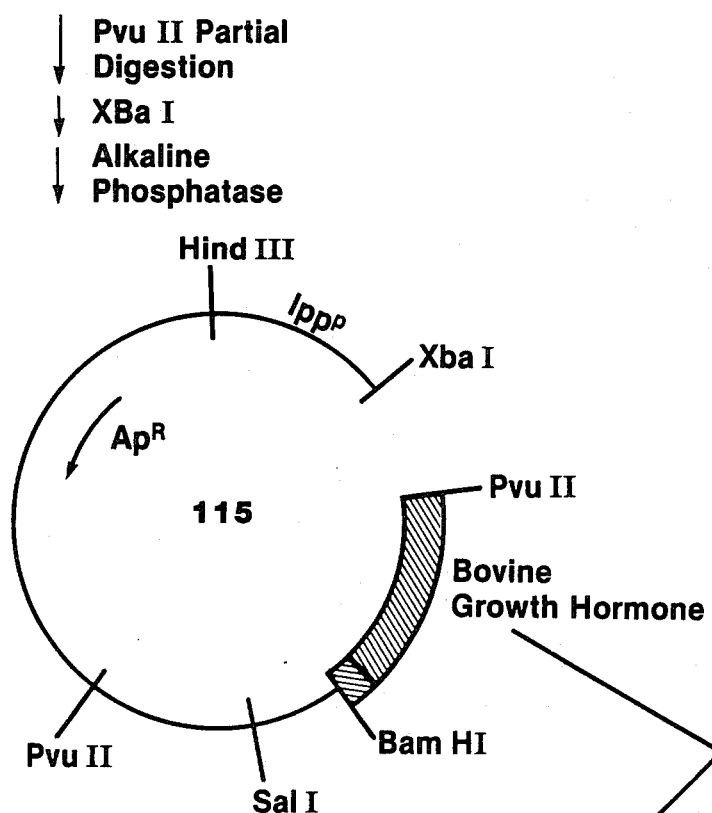
Figure 16:
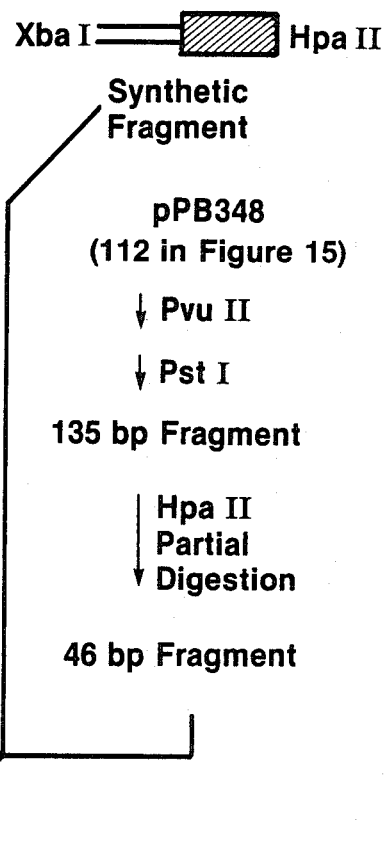
Figure 16:
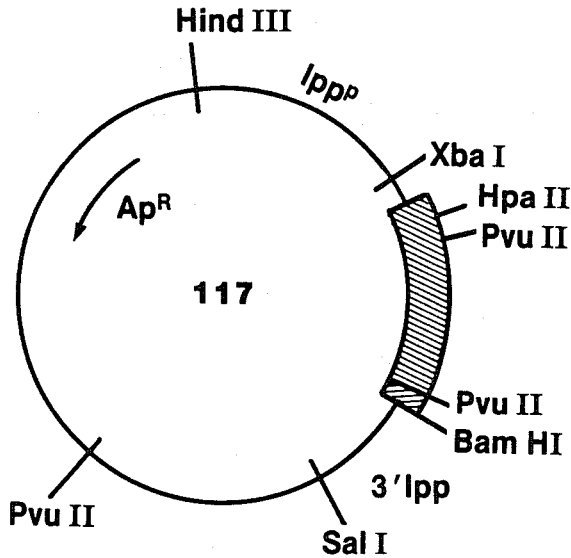

Ten micrograms of the intermediate plasmid (114 in FIG. 16) were digested with 1 unit PvuII in 200 μl PvuII buffer for 5 minutes at 37° C. After heating at 65° C. for 10 minutes, the mixture was electrophoresed on a 1 percent agarose gel and linear DNA having only a single PvuII cut per molecule was recovered and purified. This recovered material (approximately 3 μg) was digested completely with 5 units of XbaI and treated with alkaline phosphatase. The fragments were electrophoresed on a 1 percent agarose gel and the largest fragment (missing the 109 bp fragment between the XbaI and the first PvuII site in human and bovine growth hormone) was conventionally recovered (115 in FIG. 16).

The DNA sequence for the first 23 amino acids (69 bp) of bovine growth hormone up to the first PvuII site contains 2 HpaII restriction sites, the first of which is 23 bp from the first nucleotide of the coding sequence. A 63 bp fragment (116 in FIG. 16) was synthesized by the phosphotriester method. This fragment corresponds to the 19 bp sequence from the XbaI site in the lpp ribosome binding site through the ATG translational start signal followed by the coding sequence for Phe-Pro-Leu-Asp-Asp-Asp-Asp-Lys (24 bp) and 20 nucleotides of the coding sequence of bovine growth hormone (from Phe to the first HpaII site). The fragment has the following sequence:

```
XbaI
5'-CTAGAGGGTATTAATAATGTTCCC  ATTGGATGATGATGATAAGT  TCCCAGCCATGTCCTTGTC-3'  HpaII
   ||||||||||||||||||||||||  ||||||||||||||||||||  |||||||||||||||||||
3'-    TCCCATAATTATTACAAGGG  TAACCTACTACTACTATTCA  AGGGTCGGTACAGGAACAGGC-5'
```

In producing the 63 bp fragment, the following nine segments were prepared:
(1) CTAGAGGGTAT
(2) TAATAATGTTCC
(3) CATTGGATGAT
(4) GATGATAAGTTCC
(5) CAGCCATGTCCTTGTC
(6) ATGGGAACATTATTAATACCCT
(7) TTATCATCATCCA
(8) ATGGCTGGGAAC
(9) CGGACAAGGAC Using the above-prepared segments, the T4 ligase catalyzed joining reactions were performed stepwise as described below:

(a) 5'-Unphosphorylated segment 1 was joined to 5'-phosphorylated segment 2 in the presence of 5'-phosphorylated segment 6 using T4 ligase to form DNA duplex 1 which was purified by 15% polyacrylamide gel electrophoresis.

(b) 5'-Phosphorylated segments 3, 4 and 5 were joined in the presence of 5'-phosphorylated segments 7 and 8 and 5'-unphosphorylated segment 9 using T4 ligase to form DNA duplex 2 which was purified by 15% polyacrylamide gel electrophoresis.

(C) Duplexes 1 and 2 then were joined by T4 ligase to form a DNA duplex (116 in FIG. 16) which was purified by 15% polyacrylamide gel electrophoresis. This DNA duplex was then enzymatically phosphorylated using T4 polynucleotide kinase and [$\gamma$-$^{32}$P]ATP following established procedure.

The DNA fragment of 46 bp, the sequence from the above-described HpaII site to the PvuII site, can either be constructed synthetically or obtained from the original pBP348 plasmid. Accordingly, one hundred micrograms of plasmid pBP348 were digested in 400 μl of PvuII buffer with 50 units of PvuII for 2 hours at 37° C. After phenol extraction and ethanol precipitation, the DNA was dissolved in 400 μl of PstI buffer (100 mM NaCl; 10 mM Tris.HCl, pH 7.5; 10 mM MgCl$_2$; and 6 mM β-mercaptoethanol) with 50 units of PstI for 2 hours at 37° C. The DNA fragments were electrophoresed on a 6 percent polyacrylamide gel and the 135 bp fragment containing the desired 46 bp sequence was recovered and purified by standard procedures. The recovered DNA was subjected to limited digestion by 1 unit of HpaII restriction enzyme in 100 μl HpaII buffer for 10 minutes at 37° C. After heating at 65° C. for 10 minutes, the DNA fragments were run on a 5 percent acrylamide gel (acrylamide:bis ratio 19:1) along with an appropriate size marker. The desired 46 bp fragment yielded by HpaII partial digestion of the 135 bp fragment (from 112 in FIG. 16) was purified by standard procedures.

Two-tenths microgram of the XbaI-PvuII fragment of plasmid vector (115 in FIG. 16), 3.2 picomoles of synthetic 63 bp fragment (116 in FIG. 16), and 0.5 picomoles 46 bp fragment (from 112 in FIG. 116) were incubated in 10 μl ligation buffer with 2 units of T4 DNA ligase for 16 hours at 4° C. The ligation mixture was used to transform *E. coli* JA221, and the resultant transformants, which thus contained the desired plasmid pNM789, were selected on ampicillin-containing media. The identity of plasmid pNM789 (117 in FIG. 16) was confirmed by conventionally screening for the presence of both the 494 bp PvuII the 109 bp XbaI-PvuII fragments.

E. Final Construction of Plasmid pNM789B

Figure 17:
Figure 17:
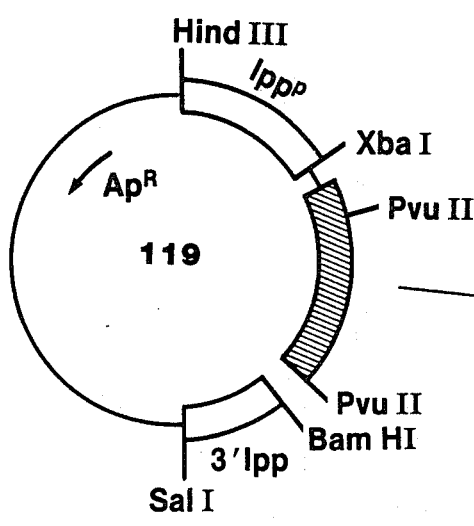
Figure 17:
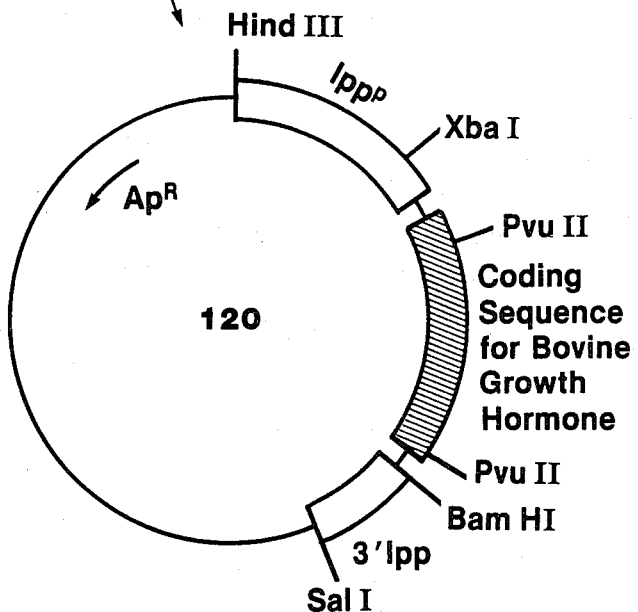

Plasmid pNM789 (117 in FIG. 17) requires one amino acid codon change for complete conversion to encode bovine growth hormone. This was accomplished by the removal of the 28 bp PvuII to BamHI fragment of plasmid pNM789 and replacement with a synthetic double stranded fragment having the following sequence (118 in FIG. 17):

Ten micrograms of plasmid pNM789 were digested with 1 unit of PvuII in 200 μl PvuII buffer for 5 minutes at 37° C. After heating 10 minutes at 65° C., the mixture was diluted to 300 μl with the addition of BamHI buffer, digested to completion with 10 units of BamHI for 1 hour at 37° C., treated with 5 units of alkaline phosphatase, and incubated for 1 hour at 65° C. The DNA fragments were separated on a 1 percent agarose gel, and a DNA fragment (119 in FIG. 17) about the size of linear plasmid pNM789 was conventionally purified. Two-tenths microgram of this fragment was ligated with 5 picomoles of synthetic fragment using 2 units of T4 ligase in 20 μl ligase buffer. The ligation was carried out overnight at 4° C. Following transformation, several plasmids were isolated and screened for the appropriate PvuII (494 bp) and XbaI-BamHI (628 bp) fragments. Plasmids comprising the aforementioned fragments constituted the desired plasmid pNM789B (120 in FIG. 17).

EXAMPLE 11

Construction of Plasmid pCZ101 and E. coli K12 RV308/pCZ101

A. Isolation of Plasmid pIM-I'-A3

The bacterium E. coli K12/pIM-I'-A3 (NRRL B-15733) was cultured in TY broth (1% tryptone, 0.5% yeast extract, 0.5% sodium chloride, and pH 7.4) with 50 μg/ml of kanamycin at 25° C. according to conventional microbiological procedures. After the culture was diluted 1:10 into fresh broth and after 3 hours incubation at 37° C., about 1.5 ml of the culture were transferred to a 1.5 ml Eppendorf tube and centrifuged for about 15 seconds. Unless otherwise indicated, all the manipulations were done at ambient temperature. The resultant supernatant was carefully removed with a fine-tip aspiratrr, and the cell pellet was resuspended in about 100 μl of freshly prepared lysozyme solution which contained 2 mg/ml lysozyme, 50 mM glucose, 10 mM EDTA, and 25 mM Tris.HCl at pH 8. About 200 μl of alkaline SDS (sodium dodecyl sulfate) solution (0.2N NaOH and 1% SDS) were added and the tube was gently inverted and then kept at 0° C. until lysis was complete (~5 minutes). Next, about 150 μl of 3M sodium acetate were added, and the contents of the tube mixed gently by inversion.

The tube was maintained at 0° C. for at least 60 minutes and then centrifuged for 15 minutes to yield an almost clear supernatant. The supernatant was transferred to a second centrifuge tube to which 3 volumes of cold 100% ethanol were added. After the tube was held on dry ice-ethanol for 5 minutes, the resultant precipitate was collected by centrifugation, and the supernatant was removed by aspiration. The pellet was dissolved in a solution of RNAse T1 and RNAse A, incubated at 65° C. for about 30 minutes, and then precipitated as before. The collected pellet was dissolved in 100 μl of TE (10 mM Tris.HCl, pH 8.0 and 1 mM EDTA) and constituted the desired plasmid pIM-I'-A3 DNA.

B. XbaI-BamHI Digestion of Plasmid pNM789B and generation of the ~0.6 kb XbaI-BamHI Fragment About 5 μg of plasmid pNM789B DNA in 50 μl Hi Salt buffer* were incubated with 10 units each of BamHI and XbaI restriction enzymes at 37° C. for about 1 hour. After the addition of 5 μl of 3M sodium acetate at pH 7.0, the DNA was precipitated with 3 volumes of 100% ethanol. The desired DNA digest was dissolved in 100 μl of TE buffer and stored at 0° C. for future use.
*Hi Salt buffer was conventionally prepared with the following composition:
100 mM NaCl
20 mM Tris.HCl, pH 8.0
10 mM MgCl₂
5 mM β-mercaptoethanol

C. XbaI-BamHI Digestion of Plasmid pIM-I'-A3

The desired digestion was carried out in substantial accordance with the procedure of Example 11B except that plasmid pIM-I'-A3, rather than plasmid pNM789B, was used. The desired DNA was dissolved in about 100 μl of TE buffer and stored at 0° C. for future use.

D. Ligation and Transformation

About 1 μg of the plasmid pIM-I'-A3 XbaI-BamHI digest, 1 μg of the plasmid pNM789B XbaI-BamHI digest, 40 μl water, 5 μl (5 mM) ATP, 5 μl ligation mix*, and 5 units T4 DNA ligase were mixed together and incubated at 20° C. for about 2 hours. After incubation at 65° C. for 2 minutes followed by cooling on ice, the resultant ligation mixture was used to transform, in substantial accordance with the transformation procedure of Wensink, 1974, Cell 3:315, E. coli K12 RV308 on TY plates (1% tryptone, 0.5% yeast extract, 0.5% sodium chloride, 1.5% agar, pH 7.4) containing 50 μg/ml of kanamycin. Bacterial strain E. coli K12 RV308 has been deposited and made part of the permanent stock culture collection of the Northern Regional Research Laboratory, Peoria, Ill., from which it is available to the public under the accession number NRRL B-15624.

Figure 18:
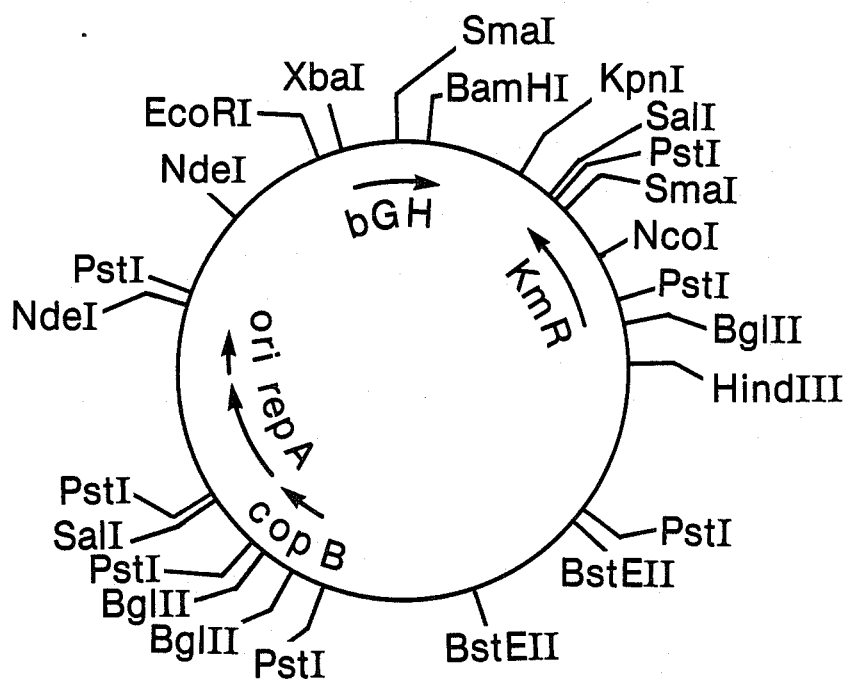
FIG. 18—the restriction site and function map of plasmid pCZ101.

Some of the resultant transformants, as conventionally shown by agarose gel electrophoresis (Maniatis et al., 1982) and other tests, contained only the desired ~10.8 kb plasmid. Such a transformant, herein designated as E. coli K12 RV308/pCZ101, was selected, plated on TY agar containing kanamycin, and then cultured using conventional microbiological techniques. The resultant cells were used to isolate plasmid pCZ101 in substantial accordance with the procedure of Example 11A. A restriction site and function map of plasmid pCZ101 is presented in FIG. 18 of the accompanying drawings.
*Ligation mix can be prepared with the following composition:
500 mM Tris.HCl, pH 7.8
200 mM Dithiothreitol
100 mM MgCl₂

EXAMPLE 12

Construction of Plasmid pCZ11

A. Construction of Intermediate Plasmid pCZ118

Ten μg of plasmid pCZ101 were dissolved in 10 μl 10× NdeI reaction buffer, 10 μl (~20 units) restriction enzyme NdeI, and 80 μl of H₂O, and the resulting reaction was incubated at 37° C. until the digestion was complete. The NdeI-digested plasmid pCZ101 DNA was precipitated and collected by centrifugation. The DNA pellet was dissolved in 10 μl 10× EcoRI reaction buffer, 2 μl (~20 units) restriction enzyme EcoRI, and 88 μl of H₂O, and the resulting reaction was incubated at 37° C. for two hours.

After again precipitating and collecting the DNA, the NdeI-EcoRI-digested plasmid pCZ101 DNA was treated with Klenow enzyme in substantial accordance with the teaching of Example 5A. The Klenow-treated DNA was diluted to a concentration of about 0.1 μg/μl in ligase buffer and then self-ligated in substantial accordance with the teaching of Example 2H to form plasmid pCZ118. DNA sequencing revealed that the Klenow enzyme was contaminated with nuclease, but, although some degradation did occur, the lpp promoter was not noticeably affected.

Competent *E. coli* K12 RV308 cells were prepared and then transformed with the plasmid pCZ118 DNA in substantial accordance with the teaching of Example 2I, except that the cells were not incubated at temperatures higher than 25° C. after the transforming DNA was added. Instead, the transforming DNA was mixed with the cells and incubated on ice for 30 minutes to one hour, and then the cells were collected by centrifugation. The cell pellet was resuspended in ~1 ml of L-broth, and the suspension was incubated at 25° C. for one hour before plating on selective plates. The *E. coli* K12 RV308/pCZ118 transformants were identified by their kanamycin-resistant phenotype and by restriction enzyme analysis of their plasmid DNA. Plasmid pCZ118 DNA was isolated from the transformants by culturing them at low temperature (~25° C.) in TY broth with kanamycin until the O.D. at 600 nm was between 0.5 and 1.0 and then incubating them at 37° C. for four or more hours. The cells were then collected and plasmid pCZ118 DNA isolated in substantial accordance with the procedure of Example 1B.

B. Construction of Intermediate Plasmid pCZ141

Ten μg of plasmid pCZ118 DNA were dissolved in 10 μl 10X BamHI buffer, 2 μl (~20 units) restriction enzyme BamHI, and 88 μl of H₂O, and the resulting reaction was placed at 37° C. for 2 hours. The BamHI-digested plasmid pCZ118 DNA was precipitated and collected by centrifugation. The DNA pellet was resuspended in Klenow buffer and treated with Klenow enzyme in substantial accordance with the teaching of Example 5B. The BamHI-digested, Klenow-treated plasmid pCZ118 DNA was then incubated at 65° C. for five minutes.

NdeI linkers (5'-CCATATGG-3' from New England Biolabs) were kinased, prepared for ligation, and ligated to the BamHI-digested, Klenow-treated plasmid pCZ118 DNA in substantial accordance with the teaching of Example 5A. After the linkers were ligated, sodium acetate (NaOAc) was added to a final concentration of 150 mM, along with 10 μl (~30 units) restriction enzyme NdeI, and the resulting reaction was incubated at 37° C. until complete NdeI digestion was observed. The NdeI-digested DNA was then loaded onto a 1% agarose gel, and the ~9.2 kb NdeI restriction fragment was isolated and purified in substantial accordance with the procedure of Example 2G. The ~5 μg of fragment obtained were suspended in 10 μl of TE buffer.

Four μl of the above-prepared DNA were self-ligated, and the resulting plasmid pCZ141 DNA was transformed into *E. coli* K12 RV308 in substantial accordance with the teaching of Example 12A. The *E. coli* K12 RV308/pCZ141 transformants were identified by their kanamycin-resistant phenotype and by restriction enzyme analysis of their plasmid DNA. Plasmid pCZ141 DNA was isolated from the transformants in substantial accordance with the teaching of Example 12A.

DNA sequencing of plasmid pCZ141 revealed that the BamHI overlaps were not "filled-in" as expected whn treating with Klenow enzyme. Instead, the BamHI overlaps and some adjoining sequences were removed from the plasmid pCZ118 DNA before the NdeI linkers were attached. This contaminating nuclease activity did not affect, in any material way, the subsequent steps in the construction of plasmid pCZ459.

C. Construction of Intermediate Plasmid pCZ10

Ten μg of plasmid pCZ141 were dissolved in 10 μl 10×XbaI reaction buffer (500 mM NaCl; 60 mM Tris-HCl, pH=7.9; 60 mM MgCl₂; and 1 mg/ml BSA), 5 μl (~50 units) restriction enzyme XbaI, and 85 μl of H₂O, and the resulting reaction was incubated at 37° C. for two hours. The XbaI-digested plasmid pCZ141 DNA was precipitated and collected by centrifugation. The DNA pellet was resuspended in 10 μl 10× NdeI reaction buffer, 10 μl (~30 units) restriction enzyme NdeI, and 80 μl of H₂O, and the resulting reaction was incubated at 37° C. until the digestion was complete.

The NdeI-XbaI-digested plasmid pCZ141 DNA was loaded onto a 1% agarose gel and the ~8.6 kb restriction fragment was isolated and purified in substantial accordance with the procedure of Example 2G. Approximately 5 μg of the fragment were obtained and suspended in 10 μl of TE buffer.

A DNA linker of sequence:

was synthesized, kinased, and prepared for ligation in substantial accordance with the teaching of Example 2B. The single-stranded DNA sequences located at both ends of the linker allow ligation with the ~8.6 kb NdeI-XbaI restriction fragment of plasmid pCZ141. The XbaI site of plasmid pCZ141 is located just downstream of the lpp promoter present on the plasmid. The linker depicted above is an adenyl- and thymidyl-rich sequence that encodes a strong ribosome-binding site for any structural gene inserted at the NdeI recognition sequence.

Figure 19:
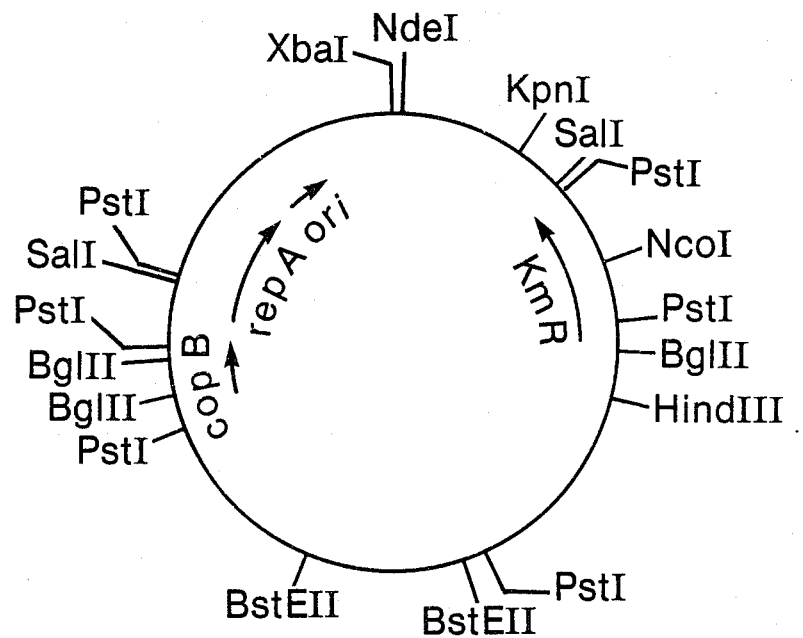
FIG. 19—the restriction site and function map of plasmid pCZ10.

Two μl of the ~8.6 kb XbaI-NdeI restriction fragment of plasmid pCZ141 and 100 picomoles of the above-described XbaI-NdeI linker were ligated, and the resulting plasmid pCZ10 DNA was transformed into *E. coli* K12 RV308 in substantial accordance with the teaching of Example 12A. The *E. coli* K12 RV308/pCZ10 transformants were identified by their kanamycin-resistant phenotype and by restriction enzyme analysis of their plasmid DNA. Plasmid pCZ10 was isolated from the transformants in substantial accordance with the procedure of Example 12A. A restriction site and function map of plasmid pCZ10 is presented in FIG. 19 of the accompanying drawings.

D. Construction of Intermediate Plasmid pCZ114

The construction of plasmid pCZ114 is disclosed in U.S. patent application Ser. No. 586,592, filed Mar. 6, 1984, in Example 3, and is incorporated by reference herein.

Ten μg of plasmid pCZ101 DNA were dissolved in 10 μl 10×XbaI reaction buffer, 2 μl (~20 units) restriction enzyme XbaI, and 88 μl of H₂O, and the resulting digest was incubated at 37° C. for 2 hours. The XbaI-digested plasmid pCZ101 DNA was precipitated and collected by centrifugation. The DNA pellet was dissolved in 10 μl 10× BamHI reaction buffer, 2 μl (~20 units) restriction enzyme BamHI, and 88 μl of H₂O, and the resulting reaction was incubated at 37° C. for 2 hours. The XbaI-BamHI-digested plasmid pCZ101

DNA was loaded onto a 1% agarose gel, and the ~10.2 kb, XbaI-BamHI restriction fragment was isolated and purified in substantial accordance with the procedure of Example 2G. Approximately 5 μg of the fragment were obtained, suspended in 10 μl of TE buffer, and stored at −20° C.

Fifty μg of plasmid pCZ101 DNA were dissolved in 20 μl 10× BamHI reaction buffer, 5 μl (~50 units) restriction enzyme BamHI, 5 μl (~50 units) restriction enzyme HgiAI, and 170 μl of H₂O, and the resulting reaction was incubated at 37° C. for 2 hours. The BamHI-HgiAI-digested plasmid pCZ101 DNA was loaded onto a 3.5% polyacrylamide gel, and the ~0.6 kb BamHI-HgiAI restriction fragment was isolated and purified in substantial accordance with the procedure of Example 2A. Approximately 5 μg of the fragment were obtained, suspended in 10 μl of TE buffer, and stored at −20° C.

A DNA linker of sequence:

```
5'-CTAGAGGGTATTAATA ATC TTC CCA TTG
   |||||||||||||||  ||| ||| ||| |||
3'-TCCCATAATTAT     TAG AAG GGT AAC

GAG GAT GAT TAA ATG TTC CCA GCC
   ||| ||| ||| ||| ||| ||| ||| |||
   CTC CTA CTA ATT TAC AAG GGT CGG

ATG TCC TTG TCC GGC CTG TTT GCC
   ||| ||| ||| ||| ||| ||| ||| |||
   TAC AGG AAC AGG CCC GAC AAA CGG

AAC GCT GTGCT-3'
   ||| ||| |
   TTG CGA C-5'
``` was constructed, kinased, and prepared for ligation in substantial accordance with the procedure of Example 2B. The above DNA linker has single-stranded DNA extensions compatible with XbaI-HgiAI-cleaved DNA.

Two μl of the ~10.2 kb XbaI-BamHI restriction fragment of plasmid pCZ101, 2 μl of the ~0.6 kb BamHI-HgiAI restriction fragment of plasmid pCZ101, and 100 picomoles of the above linker were ligated, and the resulting plasmid pCZ114 DNA was transformed into E. coli K12 RV308 in substantial accordance with the teaching of Example 12A. The E. coli K12 RV308/pCZ114 transformants were identified by their kanamycin-resistant phenotype and by restriction enzyme analysis of their plasmid DNA. Plasmid pCZ114 was isolated from the transformants in substantial accordance with the procedure of Example 12A. Plasmid pCZ114 has essentially the same restriction site and function map as plasmid pCZ101.

E. Construction of an ~0.9 kb NdeI-KpnI Restriction Fragment From Plasmid pCZ114

Fifty μg of plasmid pCZ114 DNA were dissolved in 10 μl 10×SmaI reaction buffer (1.5M NaCl; 60 mM Tris-HCl, pH=7.4; 60 mM MgCl₂; 100 mM 2-mercaptoethanol; and 1 mg/ml BSA), 5 μl (~50 units restriction enzyme SmaI, and 85 μl of H₂O, and the resulting reaction was incubated at 37° C. for 2 hours. The reaction was terminated by phenol and CHCl₃ extractions, after which the SmaI-digested plasmid pCZ114 DNA was collected by centrifugation.

NdeI linkers (5'-CCATATGG-3', New England Biolabs) were kinased and ligated to the SmaI-digested plasmid pCZ114 DNA in substantial accordance with the procedure of Example 12B. After the ligation was terminated by phenol and CHCl₃ extractions, the DNA was precipitated and collected. The DNA pellet was dissolved in 10 μl 10× KpnI reaction buffer (60 mM NaCl; 60 mM Tris-HCl, pH=7.5; 60 mM MgCl₂; 60 mM 2-mercaptoethanol; and 1 mg/ml BSA), 5 μl (~50 units) restriction enzyme KpnI, and 85 μl of H₂O, and the resulting reaction was incubated at 37° C. for 2 hours. The reaction was terminated by heating at 65° C. for 10 minutes. After cooling to room temperature, 20 μl of 10× NdeI reaction buffer, 15 μl (~45 units) restriction enzyme NdeI, and 65 μl of H₂O were added to the KpnI-digested DNA, and the resulting reaction was incubated at 37° C. for several hours.

The NdeI-KpnI digested DNA was loaded onto a 3.5% polyacrylamide gel, and the ~0.9 kb NdeI-KpnI restriction fragment was isolated and purified in substantial accordance with the procedure of Example 2A. Approximately 5 μg of the desired fragment were obtained, suspended in 10 μl, and stored at −20° C.

F. Final Construction of Plasmid pCZ11

Ten μg of plasmid pCZ10 DNA were dissolved in 10 μl 10× KpnI reaction buffer, 5 μl (~50 units) restriction enzyme KpnI, and 85 μl of H₂O, and the resulting reaction was incubated at 37° C. for 2 hours. The reaction was terminated by a 10 minute incubation at 65° C. The KpnI-digested DNA was then digested with NdeI by the addition of 20 μl 10× NdeI reaction buffer, 5 μl (~50 units) restriction enzyme NdeI, and 75 μl of H₂O, followed by a 2 hour incubation at 37° C.

The KpnI-NdeI-digested plasmid pCZ10 DNA was loaded onto a 1% agarose gel, and the ~7.9 kb NdeI-KpnI restriction fragment was purified in substantial accordance with the procedure of Example 2G. Approximately 5 μg of the fragment were obtained and suspended in 10 μl of TE buffer.

Two μl of the ~7.9 kb NdeI-KpnI restriction fragment of plasmid pCZ10 and 2 μl of the ~0.9 kb NdeI-KpnI restriction fragment of plasmid pCZ114 were ligated, and the resulting plasmid pCZ11 DNA was transformed into E. coli RV308 in substantial accordance with the procedure of Example 12A. The E. coli K12 RV308/pCZ11 transformants were identified by their kanamycin-resistant phenotype and by restriction enzyme analysis of their plasmid DNA. Plasmid pCZ11 was isolated from the transformants in substantial accordance with the procedure of Example 12A.

Plasmid pCZ11 was constructed to place a BamHI restriction enzyme recognition site "downstream" from the lpp promoter and synthetic ribosome-binding site present on plasmid pCZ10. This BamHI site allows insertion of a protein C activity-encoding DNA sequence into plasmid pCZ11, placing it under the control of the lpp promoter. This construction is described in Example 13, below.

EXAMPLE 13

Construction of Plasmid pCZ460 and Expression of a Protein C Derivative In E. coli A. Construction of Intermediate Plasmid pCZ451

Ten μg of plasmid pCZ11 were dissolved in 10 μl 10× BamHI reaction buffer, 5 μl (~10 units) restriction enzyme BamHI, 5 μl (~10 units) restriction enzyme NdeI, and 80 μl of H₂O, and the resulting reaction incubated at 37° C. for 2 hours. The NdeI-BamHI-digested plasmid pCZ11 DNA was loaded onto a 1% agarose gel, and the ~8.6 kb NdeI-BamHI restriction fragment was isolated and purified in substantial accordance with the procedure of Example 2G. Approximately 5 μg of the fragment were obtained and suspended in 10 μl of TE buffer.

A DNA linker of sequence:

was constructed, kinased, and prepared for ligation in substantial accordance with the procedure of Example 2B. The linker has single-stranded DNA extensions that allow ligation with the NdeI-BamHI-digested plasmid pCZ11 DNA prepared above. The linker was designed to encode a methionine codon and the codons for amino acid residues 33–39 of nascent human protein C. The linker was designed to be adenyl- and thymidyl-rich, yet still encode the same amino acid sequence as in native human protein C. As stated previously herein, the putative signal peptide-encoding region of the nascent human protein C structural gene was not included in the expression plasmids designed for prokaryotic host cells.

Two μl of the μ8.6 kb NdeI-BamHI restriction fragment of plasmid pCZ11 and 100 picomoles of the above linker were ligated, and the resulting plasmid pCZ451 DNA was used to transform E. coli K12 RV308 in substantial accordance with the procedure of Example 12A. The E. coli K12 RV308/pCZ451 transformants were identified by their kanamycin-resistant phenotype and by restriction enzyme analysis of their plasmid DNA. Plasmid pCZ451 DNA was isolated from the transformants in substantial accordance with the teaching of Example 12A.

Plasmid pCZ451 was partially sequenced and found to have two NdeI sites in tandem where the NdeI linkers were attached during the construction of plasmid pCZ11. Tandem NdeI sites were undesired and were removed as described in Example 13C.

B. Construction of Intermediate Plasmid pCZ455

Ten μg of plasmid pCZ451 were dissolved in 10 μl 10× BamHI reaction buffer, 2 μl (~20 units) restriction enzyme BamHI, and 88 μl of H2O, and the resulting reaction was incubated at 37° C. for 2 hours. The reaction was terminated by phenol and CHCl3 extractions, after which the DNA was precipitated and collected by centrifugation. The ~10 μg of BamHI-digested plasmid pCZ451 DNA were dissolved in 20 μl of TE buffer and stored at −20° C.

Due to the presence of a DNA restriction-modification system in E. coli K12 RV308 that is not present in E. coli K12 RR1, plasmid pHC7 DNA, as isolated in Example 1, must be transformed into and isolated from a host cell that modifies, but does not restrict, the plasmid DNA. In the present construction, such cycling is not necessary because the BamHI fragment isolated from plasmid pHC7 is not restricted by the E. coli K12 RV308 restriction system. In general, however, such cycling is necessary. E. coli K12 JA221 (NRRL B-15211) is a suitable host for such cycling.

Fifty μg of plasmid pHC7 DNA were dissolved in 10 μl 10× BamHI reaction buffer, 5 μl (~50 units) restriction enzyme BamHI, and 85 μl of H2O, and the resulting reaction was incubated at 37° C. for two hours. The BamHI-digested plasmid pHC7 DNA was loaded onto a 1% agarose gel, and the ~1.2 kb BamHI restriction fragment was isolated and purified in substantial accordance with the teaching of Example 2G. Approximately 5 μg of the fragment were obtained, dissolved in 10 μl of TE buffer, and stored at −20° C.

Two μl of the BamHI-digested plasmid pCZ451 and 2 μl of the ~1.2 kb BamHI restriction fragment of plasmid pHC7 were ligated, and the resulting plasmid pCZ455 DNA was used to transform E. coli K12 RV308 in substantial accordance with the procedure of Example 12A. The E. coli K12 RV308/pCZ455 transformants were identified by their kanamycin-resistant phenotype and by restriction enzyme analysis of their plasmid DNA. Plasmid pCZ455 was isolated from the transformants in substantial accordance with the teaching of Example 12A.

The ~1.2 kb BamHI restriction fragment of plasmid pHC7 could ligate with the BamHI-digested plasmid pCZ451 in either of two orientations. Only one of those orientations, designated plasmid pCZ455, correctly reconstructs the protein C-encoding DNA. Since the nucleotide sequence of protein C was available, restriction enzyme analysis readily identified the correct orientation. In plasmid pCZ455, the ~1.2 kb BamHI restriction fragment is oriented so that the BglII restriction enzyme recognition sequence located in the ~1.2 kb BamHI restriction fragment is placed as close to the XbaI restriction enzyme recognition sequence located at the 3' end of the lpp promoter as possible.

C. Construction of Intermediate Plasmid pCZ459

As described in Example 13A, the presence of tandem NdeI restriction sites in plasmids pCZ451 and pCZ455 was undesired. The tandem sites were located between the lpp promoter and the start triplet of the protein C-encoding DNA and could have caused out-of-frame reading of the mRNA transcript of the protein C coding sequence. Consequently, fifty μg of plasmid pCZ455 were dissolved in 10 μl 10× KpnI reaction buffer, 5 μl (~50 units) restriction enzyme KpnI, and 85 μl of H2O, and the resulting digest was incubated at 37° C. for two hours. The KpnI-digested plasmid pCZ455 DNA was then digested with NdeI by the addition of 20 μl 10×NdeI reaction buffer, 15 μl (~45 units) restriction enzyme NdeI, and 65 μl of H2O, followed by incubation of the resulting reaction at 37° C. until the NdeI digestion was complete.

The ~1.9 kb NdeI-KpnI restriction fragment was isolated from the reaction mix and purified in substantial accordance with the procedure of Example 2G. Approximately 5 μg of the fragment were obtained and suspended in 10 μl of TE buffer.

Figure 20:
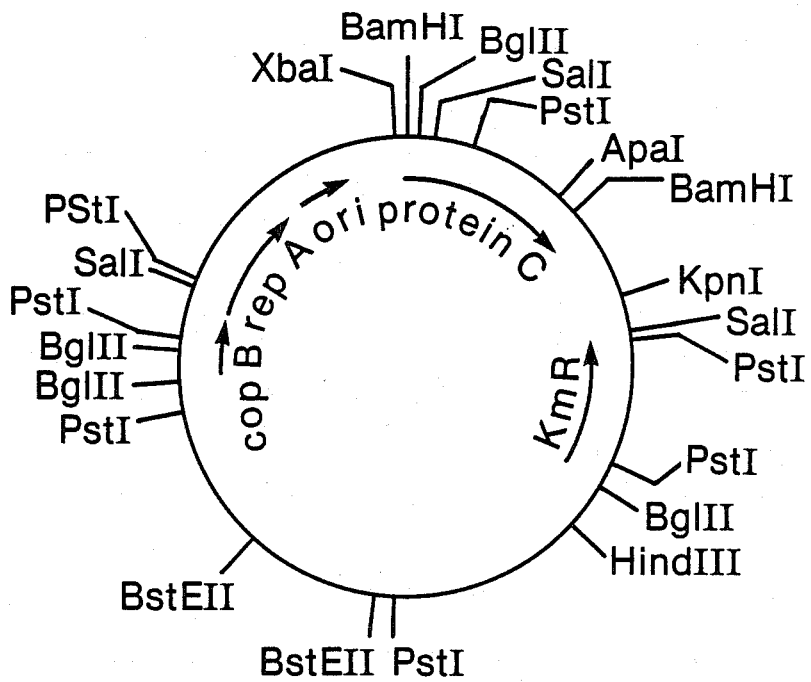
FIG. 20—the restriction site and function map of plasmid pCZ459.

Two μl of the ~7.9 kb NdeI-KpnI restriction fragment of plasmid pCZ10 prepared in Example 12F and 2 μl of the ~1.9 kb NdeI-KpnI restriction fragment of plasmid pCZ455 were ligated, and the resulting plasmid pCZ459 DNA was transformed into E. coli RV308 in substantial accordance with the procedure of Example 12A. The E. coli K12 RV308/pCZ459 transformants were identified by their kanamycin-resistant phenotype and by restriction enzyme analysis of their plasmid DNA. Plasmid pCZ459 was isolated from the transformants in substantial accordance with the procedure of Example 12A. A restriction site and function map of plasmid pCZ459 is presented in FIG. 20 of the accompanying drawings.

Plasmid pCZ459 comprises the lpp promoter positioned for expression of DNA encoding a methionine codon followed by DNA encoding the codons for amino acid residues 33–445 of nascent human protein C, as numbered above. Thus, plasmid pCZ459 comprises almost all of the nascent protein C structural gene, lacking only that portion encoding amino acid residues 2–32 of the eukaryotic signal peptide and the last 16 amino acid residues at the carboxy-terminus of protein C. The DNA located at the 3' end of the protein C-encoding portion of plasmid pCZ459 originated from the lipoprotein gene of E. coli and is transcribed along with the protein C-encoding DNA.

The mRNA transcribed from the lpp promoter of plasmid pCZ459 is translated into a polypeptide that has a methionyl residue at its amino terminus which is followed by amino acid residues 33–445 of nascent human protein C which are then followed by the amino acid sequence (using the definitions provided above):

ARG—LEU—SER—ASN—ASP—VAL—ASN—ALA—
    MET—ARG—SER—ASP—VAL—GLN—ALA—ALA—
    LYS—ASP—ASP—ALA—ALA—ARG—ALA—ASN—
    GLN—ARG—LEU—ASP—ASN—MET—ALA—THR—
                             LYS—TYR—ARG—LYS—COOH, which is encoded by the lipoprotein gene-derived DNA. This fused gene product has a calculated molecular weight of 50.5 kilodaltons (kd), and when E. coli K12 RV308/pCZ459 transformants are cultured at 37° C., they produce granules comprising this product.

The granules also comprise two distinct sub-fragments of the fused gene product, of observed molecular weights of about 35 kd and 22 kd. Theoretically, these subfragments are produced by cleavage of the fused gene product at the LYS-ARG sequence located between the light and heavy chains of human protein C (amino acid residues 198 and 199 of nascent human protein C), which yields polypeptides of calculated molecular weights of 31.7 kd and 18.8 kd. The fused gene product and both of the subfragments react with polyclonal antibody directed against native human protein C.

Construction of Intermediate Plasmid pUC19HC and Isolation of Its ~80 pp BamHI Restriction Fragement Ten μg of plasmid pUC19 (commercially available from Pharmacia P-L Biochemicals, Inc., 800 Centennial Ave., Piscataway, N.J. 08854) were dissolved in 10 μl 10× PstI reaction buffer, 2 μl (~20 units) restrictions enzyme PstI, and 88 μl of H2O, and the resulting reaction was incubated at 37° C. for 2 hours. The reaction was terminated by phenol and CHCl3 extractions, after which the DNA was precipitated and collected by centrifugation. The PstI-digested, plasmid pUC19 DNA pellet was dissolved in 20 μl of TE and stored at −20° C.

Two μl of the PstI-digested plasmid pUC19 DNA were ligated to 1 μl of the ~0.88 kb PstI restriction fragment of plasmid pHC7 prepared in Example 2D, and the resulting plasmid pUC19HC DNA was used to transform E. coli K12 RR1ΔM15 (NRRL B-15440) in substantial accordance with the procedure of Examples 2G and 2H. The transformed cells were plated on L-agar indicator plates containing 50 μg/ml ampicillin, 1 mM IPTG (isopropyl-β-D-thiogalactoside), and 50 μg/ml xG (5-bromo-4-chloro-3-indolyl-β-D-galactoside); cells transformed with plasmid pUC19 appeared blue on the indicator plates, whereas cells transformed with plasmid pUC19HC were white on the indicator plates.

Since the ~0.88 kb PstI restriction fragment of plasmid pHC7 could insert in either of two orientations, restriction enzyme analysis of the plasmid DNA was used to identify the E. coli K12 RR1ΔM15/pUC19HC transformants. Plasmid pUC19HC was designated to be that orientation which placed the BamHI restriction site located ~60 bp from one of the PstI overlaps of the ~0.88 kb PstI restriction fragment closest to the BamHI restriction site of the plasmid pUC19-derived DNA. Plasmid pUC19HC was isolated from the transformants in substantial accordance with the procedure of Example 1, except that ampicillin was the antibiotic used for selection, not tetracycline.

One hundred μg of plasmid pUC19HC DNA were dissolved in 10 μl 10× BamHI reaction buffer, 10 μl (~100 units) restriction enzyme BamHI, and 80 μl of H2O, and the resulting reaction was incubated at 37° C. for two hours. The BamHI-digested plasmid pUC19HC DNA was loaded onto a 6.5% polyacrylamide gel, and the ~80 bp BamHI restriction fragment was purified in substantial accordance with the procedure of Example 2A. Approximately 1 μg of the fragment was obtained, suspended in 5 μl of TE buffer, and stored at −20° C.

E. Preparation of BamHI-Digested Plasmid pCZ459 and Final Construction of Plasmid pCZ460

Five μg of plasmid pCZ459 were dissolved in 2 μl 10× BamHI reaction buffer, 1 μl (~5 units) restriction enzyme BamHI, and 17 μl of H2O, and the resulting reaction was incubated for 5 minutes at 37° C. The reaction was terminated by phenol and CHCl3 extractions; the reaction time was brief in order to obtain a partial BamHI digestion. After precipitating and collecting the partially BamHI-digested plasmid pCZ459, the DNA pellet was suspended in ligase buffer and ligated to 2 μl of the ~80 bp BamHI restriction fragment of plasmid pUC19HC in substantial accordance with the teaching of Example 2H.

The ligated DNA, constituting the desired plasmid pCZ460 DNA, was used to transform E. coli K12 RV308 in substantial accordance with the procedure of Example 12A. The E. coli K12 RV308/pCZ460 transformants were identified by their kanamycin-resistant phenotype and by restriction enzyme analysis of their plasmid DNA. Plasmid pCZ460 was obtained from the transformants in substantial accordance with the procedure of Example 12A.

The ~80 bp fragment could insert in either of two possible orientations and in either of the two BamHI restriction enzyme recognition sites of plasmid pCZ459. Thus, a variety of plasmids were produced in the above-described ligation. Plasmid pCZ460 was the designation given to the plasmid resulting from the insertion of the ~80 bp BamHI restriction fragment in both the proper BamHI site and also the orientation necessary to reconstruct the protein C-encoding DNA sequence. Thus, in plasmid pCZ460, amino acid residues 33–461 of nascent human protein C are properly encoded on a contiguous DNA segment located in transcriptional reading phase with the lpp promoter also present on the plasmid. Restriction enzyme analysis of plasmid pCZ460 revealed that more than one of the ~80 bp BamHI restriction fragments were ligated into the partially BamHI-digested plasmid pCZ459 starting material. Because the correct protein C-encoding DNA sequence was reconstructed properly, the additional fragments present on the plasmid neither interrupt nor extend protein C-encoding DNA sequences.

E. coli K12 RV308/pCZ460 (NRRL B-15927) transformants produce granules comprising the protein C derivative encoded on plasmid pCZ460. The protein C derivative has an observed molecular weight of about 50 kilodaltons, actually calculated from the DNA sequence to be about 48.3 kd. The *E. coli* K12 RV308/pCZ460 transformants produce three distinct polypeptides of observed molecular weights of 50 kd, 22 kd, and 34 kd that cross-react with anti-human protein C polyclonal or monoclonal antibody. The 22 kd and 34 kd polypeptides are believed to arise from cleavage of the 50 kd protein C derivative at the lysine and arginine residues (corresponding to residues 198 and 199 of the amino acid sequence given for nascent human protein C, above) that separate the light and heavy chains of active human protein C, which would yield polypeptides of calculated molecular weights of 29.5 kd and 18.8 kd.

EXAMPLE 14

Construction of HepG-2/pL133 Transformants

Although the following procedure describes the construction of HepG-2/pL133 transformants, it is equally applicable for the construction of HepG2 transformants of any of the other plasmids of the present invention, such as plasmids pSV2-HPC8, pL132, pL151, pMSV-HPC, pL141, pL142, and pMMTΔBPV-HPC. Furthermore, the procedure given is generally applicable to the cell lines listed as preferred cell lines in Table I of the present specification. Transformation procedures for eukaryotic host cells are well known in the art, i.e., Wigler et al., 1979, P.N.A.S. USA 76:1373 and Graham et al., 1973, Virology 52:456.

A. Preparation of the Cells

A culture of human hepatoblastoma cells, HepG-2 (ATCC # HB 8065) was passaged one to two days prior to the transformation, so as to provide 40-50% confluency on the day of the transformation. The media was changed two to three hours before the transformation. One 25 cm² flask of cells is needed for each transformation.

B. Preparation of the DNA

Ten to twenty µg of plasmid pL133 DNA were added to 62.5 µl of 2M CaCl$_2$ and 437.5 µl of H$_2$O. The 0.5 ml of DNA were then added dropwise to 0.5 ml of 2× HeBS (10 g/L Hepes, pH=7.5; 16 g/L NaCl; 0.74 g/L KCl; 0.25 g/L Na$_2$PO$_4$; and 2 g/L dextrose), forming a milky precipitate. The mixture was allowed to stand for 10-20 minutes at room temperature before it was added to the cells. A longer incubation time may result in a coarser precipitate that does not transform well, but sometimes a longer incubation time may be necessary to form a precipitate.

C. Transformation of the Cells

The 1 ml DNA solution prepared in Example 14B was added to a 25 cm² flask of HepG-2 cells with gentle agitation and incubated at 37° C. for 3-4 hours. Using care not to detach the cells, the cells were washed twice with serum-free growth media (Dulbecco's Modified Eagle Medium, Gibco). One ml of HeBS with 15% glycerol was added to the cells, which were then incubated at 37° C. for two minutes.

The "glycerol-shock" incubation was terminated by the addition of serum-free growth media, followed by two washes with serum-free growth media. Complete fresh growth media containing a serum-substitute (either bovine serum albumin or Ultroser-G, which is marketed by Reactiff I.B.F. Foc. Chim. (LKB), Pointet Girard, 92390 Villeneuvela Garenne, France) and 12.5 µg/ml vitamin K$_1$ was then added, and the cells were returned to a 37° C. incubator. Fetal calf serum was not used in the media, because it contains bovine factors and proteases that interfere with protein C assays.

For transient assays, usually terminated about 96 hours post-transformation, sodium butyrate was added at 5 mM final concentration. For transformations involving a plasmid that comprised a selectable marker, such as the G418R or dhfr gene, when selection of stable transformants was desired, the sodium butyrate was not added, and the selective agent (e.g., 400 µg/ml G418) was added about two to four days post-transformation. At this time complete media containing fetal calf serum is added, and cells are allowed to propagate in selection media for two to three weeks with a change of media every 5-7 days. Individual clones are then isolated for further analysis.

D. Assay for Protein C

HepG-2/pL133 transformants and HepG-2 mock-transformed cells were assayed for protein C about 96 hours after transformation. Mock-transformed cells have been subjected to the transformation procedure but have not been exposed to transforming DNA. The assay requires antibody directed against protein C, as described below. Purification of protein C, for subsequent use to prepare antibody against protein C, can be accomplished as described by Kisiel, 1979, J. Clin. Invest. 64:761. Polyclonal antibody can be prepared by the procedure disclosed in *Structural Concepts in Immunology and Immunochemistry* by E. A. Kabat, published in 1968 by Holt, Rhinehart, and Winston. Monoclonal antibody can be prepared as disclosed in Kohler and Milstein, 1975, Nature, 256:495.

Goat anti-human protein C polyclonal antibody was incubated overnight in a 96-well tissue culture dish to bind the antibody to the plastic. After washing the wells with buffer, media samples from HepG-2/pL133 transformants and from mock-transformed HepG-2 cells were added to the wells. The media samples were taken 96 hours post-transformation. After incubating the media samples in the wells for two hours at 37° C., the wells were rinsed with buffer, and mouse anti-human protein C monoclonal IgG was added to the wells and incubated overnight at 4° C.

After rinsing out the unbound monoclonal antibody with buffer, peroxidase-conjugated, sheep anti-mouse IgG was added to the wells and incubated at 37° C. for 2 hours. After rinsing with buffer, a solution of ABTS (2,2'-azino-di-3-ethylbenzthiazoline-sulfonate) was added to the wells, and incubation in the dark at room temperature was continued, with optical density of the samples being measured at 405 nm every 30 minutes for 2 hours.

In essence, the assay works by the protein C becoming bound to the polyclonal antibody which is attached to the dish. The monoclonal antibody then attaches to the protein C, and the peroxidase-conjugated, anti-mouse IgG becomes bound to the monoclonal antibody. The peroxidase reacts with ABTS in a time-dependent reaction to give a product that strongly absorbs at 405 nm. Simply stated, the more protein C in the sample, the higher the O.D. measurement at 405 nm.

The HepG-2/pL133 transformants gave readings up to ten fold higher than those from mock-transformed cells, indicating plasmid-driven expression of protein C in the HepG-2/pL133 transformants. Because HepG-2 cells comprise a chromosomal protein C structural gene, mRNA was isolated from the transformants to determine if plasmid-encoded, protein C message was present. The transformants were shown to have ~5× more plasmid-derived protein C mRNA than chromosomal-derived protein C mRNA. The readings correspond to about 100 ng to 300 ng of protein C per ml of conditioned media.

Similar assays were conducted with CHO-K1 (dhfr−)/pL141 transformants, and about 1.8 μg of protein C were observed per ml of conditioned media. CHO-K1(dhfr−) host cells, such as DXB11 host cells, lack the wild-type dihydrofolate reductase gene found in CHO-K1 cells. Such dhfr− CHO-K1 host cells can be generated in accordance with the procedure disclosed in Urlaub and Chasin, 1980, P.N.A.S. 77:4216. The DXB11/pL141 transformants express more protein C, because more copies of the recombinant protein C gene are present in DXB11/pL141 transformants than in HepG-2/pL133 transformants due to the amplification of the recombinant DNA. As stated above, this amplification is well known in the art (see U.S. Pat. No. 4,399,216, issued 8/16/83) and is accomplished by exposing the host cells transformed with a plasmid comprising a wild-type dhfr gene to increasing amounts of methotrexate. This methotrexate-mediated amplification can be accomplished in a wide variety of host cells and is not limited to dhfr− cell lines. Protein C assays conducted with LLC-MK$_2$/pL132 transformants showed about 25 ng of protein C per ml of conditioned media.

EXAMPLE 15

Activation of Recombinant Human Protein C Zymogen

This example applies to recombinant human protein C isolated from conditioned tissue culture medium from mammalian cells expressing and secreting recombinant human protein C. Protein C contained in conditioned tissue culture medium can also be activated directly, without prior purification.

The activation makes use of rabbit thrombomodulin complexed with bovine thrombin; the complex is immobilized on agarose beads. The agarose beads are sedimentable and are therefore readily removed from the activation mixture. The thrombomodulin-thrombin may be immobilized to agarose beads in the following manner. A monoclonal antibody with high binding affinity for rabbit thrombomodulin is covalently linked to crosslinked agarose beads with 6–8 carbon atom arms (e.g., Affigel ™ 102 or Affigel ™ 202, Bio Rad, Richmond, Calif.). The purified murine IgG monoclonal antibody, depending on the chemical structure of the arm of the crosslinked agarose, can be linked covalently via its free carboxyl or free amino groups using conventional carbodiimide compounds for covalent linkage. For example, approximately 0.15 OD units of IgG protein may be covalently linked to the agarose gel matrix. Next, a highly purified rabbit thrombomodulin preparation is diluted to 0.15 OD units/ml with a buffer that is 0.02M Tris-HCl, pH 7.4, and 0.15M in NaCl. Then, one volume of packed agarose beads with monoclonal anti-thrombomodulin antibody attached is mixed with one volume thrombomodulin and the mixture incubated overnight with gentle mixing.

The beads are then centrifuged, and the amount of thrombomodulin bound is estimated by determining the A$_{280}$ of the supernatant, assuming an E$_{1\%}$ (extinction coefficient) of 8.8 and a M$_r$ (molecular weight) of 75 kd for the purified protein. Bovine thrombin purified to apparent homogeneity (specific activity: 2,000 NIH U/mg) is added in amounts slightly in excess of the amount calculated to be equimolar to the immobilized thrombomodulin. The beads are then incubated from 30 minutes to overnight at 4° C. Following this incubation, the beads are washed 6–10 times with the 0.02M Tris-HCl, pH 7.4, and 0.15M NaCl buffer, and the beads are then stored at 4° C. in this buffer.

One ml of the purified protein C solution or protein C-containing tissue culture media is added to 50 microliters of packed beads and incubated on a rocker for 30 minutes at 37° C. The activation of the zymogen to the activated serine protease readily occurs in a variety of physiological pH and ionic strength buffers usually containing one mg/ml bovine serum albumin (radioimmunoassay grade, Sigma, St. Louis, MO). The activation reaction requires calcium, and therefore, CaCl$_2$ is usually added to the activation mixture to a final concentration of 0.005–0.025M.

At the end of the incubation period, the beads are removed by centrifugation, and human antithrombin III, purified to apparent homogeneity, is added to quench any free thrombin which is still present. Twenty μl of purified antithrombin III (1 OD unit/ml) is added to each 500 microliters of activation mixture. After 15 minutes incubation at room temperature, the activation mixture is then tested for activated protein C activity using the synthetic peptide paranitroanilide (pNA) substrate, H-D-Phe-Pip-Arg-pNA (S-2238, Kabi-Vitrum, Stockholm, Sweden), or other tripeptide paranitroanilide substrates sensitive to activated protein C.

By this technique, activation and expression of activated protein C activity is possible with protein C, irrespective of whether the post-translational γ-carboxylation modification has occurred. However, the activation rate of "gla-less" protein C is about 20% of the activation rate of the protein which has undergone post translational modifications. If the expressed product does not contain γ-carboxyglutamate residues, the activation incubation period is prolonged to the extent which takes this slower activation rate into account.

Alternatively, activated protein C activity can be measured in a clotting assay which utilizes bovine clotting factor Xa, purified to apparent homogeneity, and which measures the rate of inactivation of clotting factor Va, the obligatory, activated protein C-sensitive cofactor in the factor Xa mediated conversion of prothrombin into thrombin. Conditioned media from HepG-2/pL133 transformants has been subjected to the activation procedure described above and, as demonstrated by the clotting assays, has been shown to have ~2× to more activated protein C (~250 ng/ml) than mock-transformed HepG-2 cells (~125 ng/ml).

Protein C isolated from the medium of CHO-K1-(dhfr−)/pL141 transformants was activated in accordance with the procedure of this Example and tested in the clotting and amidolytic assays. The assays demonstrated that the protein C was active and indicated that the transformed CHO-K1 host cells possessed substantial γ-carboxylase activity. Because many polypeptides, including, but not limited to, vitamin K-dependent serine proteases, such as protein C, require γ-carboxylation for at least a portion of their biological activity, and because few cell lines, such as, for example, the HepG-2 and H4IIEC3 cell lines, possess γ-carboxylase activity, the expression of substantial γ-carboxylase activity in CHO-K1 host cells was unexpected. Therefore, the present invention also comprises a method for using

| | 5'-R¹N—RM—GCC | AAC | TCC | TTC | CTG | GAG | GAG | CTC | CGT | CAC | AGC |
|---|---|---|---|---|---|---|---|---|---|---|---|
| AGC | CTG | GAG | CGG | GAG | TGC | ATA | GAG | GAG | ATC | TGT | GAC | TTC | GAG |
| GAG | GCC | AAG | GAA | ATT | TTC | CAA | AAT | GTG | GAT | GAC | ACA | CTG | GCC |
| TTC | TGG | TCC | AAG | CAC | GTC | GAC | GGT | GAC | CAG | TGC | TTG | GTC | TTG |
| CCC | TTG | GAG | CAC | CCG | TGC | GCC | AGC | CTG | TGC | TGC | GGG | CAC | GGC |
| ACG | TGC | ATC | GAC | GGC | ATC | GGC | AGC | TTC | AGC | TGC | GAC | TGC | CGC |
| AGC | GGC | TGG | GAG | GGC | CGC | TTC | TGC | CAG | CGC | GAG | GTG | AGC | TTC |
| CTC | AAT | TGC | TCG | CTG | GAC | AAC | GGC | GGC | TGC | ACG | CAT | TAC | TGC |
| CTA | GAG | GAG | GTG | GGC | TGG | CGG | CGC | TGT | AGC | TGT | GCG | CCT | GGC |
| TAC | AAG | CTG | GGG | GAC | GAC | CTC | CTG | CAG | TGT | CAC | CCC | GCA | GTG |
| AAG | TTC | CCT | TGT | GGG | AGG | CCC | TGG | AAG | CGG | ATG | GAG | AAG | AAG |
| CGC | AGT | CAC | CTG | AAA | CGA | GAC | ACA | GAA | GAC | CAA | GAA | GAC | CAA |
| GTA | GAT | CCG | CGG | CTC | ATT | GAT | GGG | AAG | ATG | ACC | AGG | CGG | GGA |
| GAC | AGC | CCC | TGG | CAG | GTG | GTC | CTG | CTG | GAC | TCA | AAG | AAG | AAG |
| CTG | GCC | TGC | GGG | GCA | GTG | CTC | ATC | CAC | CCC | TCC | TGG | GTG | CTG |
| ACA | GCG | GCC | CAC | TGC | ATG | GAT | GAG | TCC | AAG | AAG | CTC | CTT | GTC |
| AGG | CTT | GGA | GAG | TAT | GAC | CTG | CGG | CGC | TGG | GAG | AAG | TGG | GAG |
| CTG | GAC | CTG | GAC | ATC | AAG | GAG | GTC | TTC | GTC | CAC | CCC | AAC | TAC |
| AGC | AAG | AGC | ACC | ACC | GAC | AAT | GAC | ATC | GCA | CTG | CTG | CAC | CTG |
| GCC | CAG | CCC | GCC | ACC | CTC | TCG | CAG | ACC | ATA | GTG | CCC | ATC | TGC |
| CTC | CCG | GAC | AGC | GGC | CTT | GCA | GAG | CGC | GAG | CTC | AAT | CAG | GCC |
| GGC | CAG | GAG | ACC | CTC | GTG | ACG | GGC | TGG | GGC | TAC | CAC | AGC | AGC |
| CGA | GAG | AAG | GAG | GCC | AAG | AGA | AAC | CGC | ACC | TTC | GTC | CTC | AAC |
| TTC | ATC | AAG | ATT | CCC | GTG | GTC | CCG | CAC | AAT | GAG | TGC | AGC | GAG |
| GTC | ATG | AGC | AAC | ATG | GTG | TCT | GAG | AAC | ATG | CTG | TGT | GCG | GGC |
| ATC | CTC | GGG | GAC | CGG | CAG | GAT | GCC | TGC | GAG | GGC | GAC | AGT | GGG |
| GGG | CCC | ATG | GTC | GCC | TCC | TTC | CAC | GGC | ACC | TGG | TTC | CTG | GTG |
| GGC | CTG | GTG | AGC | TGG | GGT | GAG | GGC | TGT | GGG | CTC | CTT | CAC | AAC |
| TAC | GGC | GTT | TAC | ACC | AAA | GTC | AGC | CGC | TAC | CTC | GAC | TGG | ATC |
| CAT | GGG | CAC | ATC | AGA | GAC | AAG | GAA | GCC | CCC | CAG | AAG | AGC | TGG |
| GCA | CCT | TAG—3' | | | | | | | | | | | |

CHO-K1 host cells, including the dhfr⁻ derivatives thereof, to produce γ-carboxylated polypeptides, especially the vitamin K-dependent serine proteases, such as human protein C.

Whether an amidolytic or clotting assay is utilized, calibration curves are typically established using highly purified activated protein C derived from human plasma as the standard.

The immobilized thrombomodulin-thrombin preparation is reuseable; full activating activity is readily regained after repeated washing of the beads in the 0.02M Tris-HCl, pH 7.4, and 0.15M NaCl buffer.

This technique is suitable for the activation of large quantities of protein C in large volumes. If large volumes are to be activated, the beads are packed into a column of appropriate size for the amount of protein C to be activated, and the protein C solution is passed over the column at low flow rates (e.g. 6–10 ml/h).

We claim:

1. A constructed DNA compound that comprises double-stranded deoxyribonucleic acid that encodes a polypeptide with human protein C activity, wherein the coding strand is:

wherein
A is deoxyadenyl,
G is deoxyguanyl,
C is deoxycytidyl,
T is thymidyl,
R is 5'-GCC CAC CAG GTG CTG CGG ATC CGC AAA CGT-3' or 5'-CAC CAG GTG CTG CGG ATC CGC AAA CGT-3'
R¹ is

| 5'-ATG TGG | CAG | CTC | ACA | AGC | CTC | CTG | CTG | TTC | GTG |
|---|---|---|---|---|---|---|---|---|---|
| GCC ACC | TGG | GGA | ATT | TCC | GGC | ACA | CCA | GCT | CCT |
| CTT GAC | TCA | GTG | TTC | TCC | AGC | AGC | GAG | CGT—3' | |
| or 5'-ATG TGG | CAG | CTC | ACA | AGC | CTC | CTG | CTG | TTC | GTG |
| GCC ACC | TGG | GGA | ATT | TCC | GGC | ACA | CCA | GCT | CCT |
| CTT GAC | TCA | GTG | TTC | TCC | AGC | AGC | GAG | CGT GCC—3' | |

M is 0 or 1, and
N is 0 or 1,
provided that when M is 0, N must necessarily also be 0 and that when
R is 5'-GCC CAC CAG GTG CTG CGG ATC CGC AAA CGT-3',
R¹ must necessarily be

| 5'-ATG TGG | CAG | CTC | ACA | AGC | CTC | CTG | CTG | TTC | GTG |
|---|---|---|---|---|---|---|---|---|---|
| GCC ACC | TGG | GGA | ATT | TCC | GGC | ACA | CCA | GCT | CCT |
| CTT GAC | TCA | GTG | TTC | TCC | AGC | AGC | GAG | CGT—3'; | | and that when
R is 5'-CAC CAG GTG CTG CGG ATC CGC AAA CGT-3',
R¹ must necessarily be

```
5'-ATG TGG CAG CTC ACA AGC CTC CTG CTG TTC GTG
   GCC ACC TGG GGA ATT TCC GGC ACA CCA GCT CCT
   CTT GAC TCA GTG TTC TCC AGC AGC GAG CGT GCC-3'.
```

2. A plasmid comprising the DNA of claim 1.
3. The plasmid of claim 2 that is plasmid pHC7.
4. The plasmid of claim 2 that is plasmid pSV2-HCP8.
5. The plasmid of claim 2 that is plasmid pMSV-HPC.
6. The plasmid of claim 2 that is plasmid pL133.
7. The plasmid of claim 2 that is plasmid pL132.
8. The plasmid of claim 2 that is plasmid pL151.
9. The plasmid of claim 2 that is plasmid pL141.
10. The plasmid of claim 2 that is plasmid pL142.
11. The plasmid of claim 2 that is plasmid pMMTΔBPV-HPC.
12. A method of producing a polypeptide with human protein C activity in a eukaryotic host cell, said method comprising:
   A. transforming said eukaryotic host cell with a recombinant DNA vector, said vector comprising:
      (i) a DNA sequence that provides for autonomous replication or chromosomal integration of said vector in said host cell;
      (ii) a promoter and translational activating sequence functional in said host cell; and
      (iii) a DNA compound of claim 1 positioned in transcriptional and translational reading phase with said promoter and translational activating sequence, provided that when N=1, said translational activating sequence does not encode a translational start codon;
   B. culturing said host cell transformed in step A under conditions suitable for gene expression.
13. The method of claim 12, wherein said host cell is selected from the group consisting of cells of HepG-2, *Aedes aegypti*, CV-1, LLC-MK₂, 3T3, CHO-K1, CHO-K1 (dhfr⁻), *Anthraea eucalypti*, HeLa, RPMI8226, H4IIEC3, C127I, and HS-Sultan.
14. The method of claim 13, wherein said host cell is selected from the cell line HepG-2.
15. The method of claim 13, wherein said host cell is selected from the cell line *Aedes aegypti*.
16. The method of claim 13, wherein said host cell is selected from the cell line C127I.
17. The method of claim 13, wherein said host cell is selected from the cell line LLC-MK₂.
18. The method of claim 13, wherein said host cell is selected from the cell line 3T3.
19. The method of claim 13, wherein said host cell is selected from the cell line H4IIEC3.
20. The method of claim 14, wherein the host cell cultured in step B is HepG-2/pL133.
21. The method of claim 14, wherein the host cell cultured in step B is HepG-2/pSV2-HPC8.
22. The method of claim 18, wherein the host cell cultured in step B is 3T3/pL142.
23. The method of claim 16, wherein the host cell cultured in step B is C127I/pSV2-HPC8.
24. The method of claim 12, wherein said recombinant DNA vector further comprises a selectable marker that functions in said eukaryotic host cell.
25. The method of claim 24, wherein the host cell cultured in step B is HepG-2/pL132.
26. The method of claim 24, wherein the host cell cultured in step B is HepG-2/pL151.
27. The method of claim 24, wherein the host cell cultured in step B is HepG-2/pL141.
28. The method of claim 24, wherein the host cell cultured in step B is HepG-2/pMSV-HPC.
29. The method of claim 24, wherein the host cell cultured in step B is RPMI8226/pL151.
30. The method of claim 24, wherein the host cell cultured in step B is RPMI8226/pL132.
31. The method of claim 24, wherein the host cell cultured in step B is RPMI8226/pMSV-HPC.
32. The method of claim 24, wherein the host cell cultured in step B is RPMI8226/pL141.
33. The method of claim 24, wherein the host cell cultured in step B is CV-1/pL132.
34. The method of claim 24, wherein the host cell cultured in step B is CV-1/pL151.
35. The method of claim 24, wherein the host cell cultured in step B is CV-1/pL141.
36. The method of claim 24, wherein the host cell cultured in step B is LLC-MK₂/pL132.
37. The method of claim 24, wherein the host cell cultured in step B is CHO-K1(dhfr⁻)/pL141.
38. The method of claim 24, wherein the host cell cultured in step B is LLC-MK₂/pL141.
39. The method of claim 24, wherein the host cell cultured in step B is LLC-MK₂/pL151.
40. The method of claim 24, wherein the host cell cultured in step B is 3T3/pL132.
41. The method of claim 24, wherein the host cell cultured in step B is CHO-K1/pL151.
42. The method of claim 24, wherein the host cell cultured in step B is 3T3/pMMTΔBPV-HPC.
43. The method of claim 24, wherein the host cell cultured in step B is CHO-K1/pL141.
44. The method of claim 24, wherein the host cell cultured in step B is CHO-K1(dhfr⁻)/pL151.
45. The method of claim 24, wherein the host cell cultured in step B is HeLa/pL132.
46. The method of claim 24, wherein the host cell cultured in step B is CHO-K1/pMSV-HPC.
47. The method of claim 24, wherein the host cell cultured in step B is H4IIEC3/pL132.
48. The method of claim 24, wherein the host cell cultured in step B is CHO-K1(dhfr⁻)/pMSV-HPC.
49. The method of claim 24, wherein the host cell cultured in step B is H4IIEC3/pMMTΔBPV-HPC.
50. The method of claim 24, wherein the host cell cultured in step B is H4IIEC3/pL141.
51. The method of claim 24, wherein the host cell cultured in step B is C127I/pL151.
52. The method of claim 24, wherein the host cell cultured in step B is C127I/pMMTΔBPV-HPC.
53. The method of claim 24, wherein the host cell cultured in step B is C127I/pL141.
54. The method of claim 24, wherein the host cell cultured in step B is HS-Sultan/pL132.
55. The method of claim 24, wherein the host cell cultured in step B is HS-Sultan/pL141.
56. The host cell used in the method of claim 20 which is HepG-2/pL133.
57. The host cell used in the method of claim 23 which is C127I/pSV2-HPC8.

58. The host cell used in the method of claim 25 which is HepG-2/pL132.

59. The host cell used in the method of claim 26 which is HepG-2/pL151.

60. The host cell used in the method of claim 27 which is HepG-2/pL141.

61. The host cell used in the method of claim 32 which is RPMI8226/pL141.

62. The host cell used in the method of claim 35 which is CV-1/pL141.

63. The host cell used in the method of claim 36 which is LLC-MK$_2$/pL132.

64. The host cell used in the method of claim 41 which is CHO-K1/pL151.

65. The host cell used in the method of claim 43 which is CHO-K1/pL141.

66. The host cell used in the method of claim 44 which is CHO-K1(dhfr$^-$)/pL151.

67. The host cell used in the method of claim 52 which is C127I/pMMTΔBPV-HPC.

68. The double-stranded deoxyribonucleic acid of claim 1, wherein N is 0 and M is 1.

69. A method of producing human protein C activity in a prokaryotic host cell, said method comprising:
  A. transforming said prokaryotic host cell with a recombinant DNA vector, said vector comprising:
    (i) a DNA sequence that provides for autonomous replication or chromosomal integration of said vector in said host cell;
    (ii) a promoter and translational activating sequence functional in said host cell;
    (iii) a DNA compound of claim 1, wherein N=0 and M=0 or 1, positioned in transcriptional and translational reading phase with said promoter and translational activating sequence; and
    (iv) a selectable marker;
  B. culturing said prokaryotic host cell under conditions suitable for gene expression.

70. The method of claim 69, wherein said prokaryotic host cell is selected from the group consisting of Bacillus, Streptomyces, and E. coli.

71. The method of claim 70, wherein said host cell is E. coli K12.

72. The method of claim 71, wherein said host cell is E. coli K12 RV308.

73. The method of claim 71, wherein said host cell is E. coli K12 MM294.

74. The method of claim 71, wherein said host cell is E. coli K12 RR1.

75. The method of claim 71, wherein said host cell is E. coli K12 RR1ΔM15.

76. A plasmid selected from the group consisting of pUC19HC, pCZ118, pCZ10, pCZ11, pCZ451, pCZ459, and pCZ455.

77. The plasmid of claim 2 that is plasmid pCZ460.

78. The host cell cultured in step B of the method of claim 72 that is E. coli K12 RV308/pCZ460.

79. The host cell cultured in step B of the method of claim 73 that is E. coli K12 MM294/pCZ460.

80. A method of claim 12, wherein said host cell is a CHO-K1 host cell, including the dhfr$^-$ derivatives thereof.

81. A constructed, recombinant DNA sequence that comprises the coding sequence for the active light chain of human protein C, said active light chain having the amino acid residue sequence:

| | | | | | | | | | | | | | | | |
|---|---|---|---|---|---|---|---|---|---|---|---|---|---|---|---|
| ALA | ASN | SER | PHE | LEU | GLU | GLU | LEU | ARG | HIS | SER | SER | LEU | GLU | ARG | GLU |
| CYS | ILE | GLU | GLU | ILE | CYS | ASP | PHE | GLU | GLU | ALA | LYS | GLU | ILE | PHE | GLN |
| ASN | VAL | ASP | ASP | THR | LEU | ALA | PHE | TRP | SER | LYS | HIS | VAL | ASP | GLY | ASP |
| GLN | CYS | LEU | VAL | LEU | PRO | LEU | GLU | HIS | PRO | CYS | ALA | SER | LEU | CYS | CYS |
| GLY | HIS | GLY | THR | CYS | ILE | ASP | GLY | ILE | GLY | SER | PHE | SER | CYS | ASP | CYS |
| ARG | SER | GLY | TRP | GLU | GLY | ARG | PHE | CYS | GLN | ARG | GLU | VAL | SER | PHE | LEU |
| ASN | CYS | SER | LEU | ASP | ASN | GLY | GLY | CYS | THR | HIS | TYR | CYS | LEU | GLU | GLU |
| VAL | GLY | TRP | ARG | ARG | CYS | SER | CYS | ALA | PRO | GLY | TYR | LYS | LEU | GLY | ASP |
| ASP | LEU | LEU | GLN | CYS | HIS | PRO | ALA | VAL | LYS | PHE | PRO | CYS | GLY | ARG | PRO |
| TRP | LYS | ARG | MET | GLU | LYS | LYS | ARG | SER | HIS | LEU | | | | | | wherein ALA is Alanine, ARG is Arginine, ASN is Asparagine, ASP is Aspartic Acid, CYS is Cysteine, GLN is Glutamine, GLU is Glutamic Acid, GLY is Glycine, HIS is Histidine, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

82. The DNA sequence of claim 81 wherein the coding strand is:

| | | | | | | | | | | | | |
|---|---|---|---|---|---|---|---|---|---|---|---|---|
| | | | 5'-GCC | AAC | TCC | TTC | CTG | GAG | GAG | CTC | CGT | CAC | AGC |
| AGC | CTG | GAG | CGG | GAG | TGC | ATA | GAG | GAG | ATC | TGT | GAC | TTC | GAG |
| GAG | GCC | AAG | GAA | ATT | TTC | CAA | AAT | GTG | GAT | GAC | ACA | CTG | GCC |
| TTC | TGG | TCC | AAG | CAC | GTC | GAC | GGT | GAC | CAG | TGC | TTG | GTC | TTG |
| CCC | TTG | GAG | CAC | CCG | TGC | GCC | AGC | CTG | TGC | TGC | GGG | CAC | GGC |
| ACG | TGC | ATC | GAC | GGC | ATC | GGC | AGC | TTC | AGC | TGC | GAC | TGC | CGC |
| AGC | GGC | TGG | GAG | GGC | CGC | TTC | TGC | CAG | CGC | GAG | GTG | AGC | TTC |
| CTC | AAT | TGC | TCG | CTG | GAC | AAC | GGC | GGC | TGC | ACG | CAT | TAC | TGC |
| CTA | GAG | GAG | GTG | GGC | TGG | CGG | CGC | TGT | AGC | TGT | GCG | CCT | GGC |
| TAC | AAG | CTG | GGG | GAC | CTC | CTG | CAG | TGT | CAC | CCC | GCA | GTG | |
| AAG | TTC | CCT | TGT | GGG | AGG | CCC | TGG | AAG | CGG | ATG | GAG | AAG | AAG |
| CGC | AGT | CAC | CTG-3' | | | | | | | | | | | wherein A is deoxyadenyl, G is deoxyguanyl, C is deoxycytidyl, and T is thymidyl.

* * * * *

UNITED STATES PATENT AND TRADEMARK OFFICE
CERTIFICATE OF CORRECTION

PATENT NO. : 4,775,624

DATED : October 4, 1988

INVENTOR(S) : Bang et al.

It is certified that error appears in the above-identified patent and that said Letters Patent is hereby corrected as shown below:

In column 3, line 20, please change "glutamic residues" to -- glutamic acid residues --.

In column 4, line 28, please change "cell grow" to -- cell that cannot grow --.

In column 6, line 1 of the amino acid sequence, please change "SER LEU LEU PHE" to -- SER LEU LEU LEU PHE --.

In column 7, please change amino acid 264 from "SRG" to -- ARG --.

In column 9, line 8, please change "3+" to -- 3' --.

In column 13, line 12, please change 'pMSV-PC" to -- pMSV-HPC --.

In column 13, line 50, after "C127I/pL151" please add -- 3T3/pMSV-HPC, 3T3/pMMTΔBPV-HPC, --.

In column 13, line 57, after "pMMTΔBPV-HPC," please add -- CHO-K1(dhfr⁻)/pL132, CHO-K1(dhfr⁻)/pL141, --.

In column 15, line 9, please change "teh" to -- the --.

In column 16, line 28, please change "a strain part" to -- a strain deposited and made part --.

UNITED STATES PATENT AND TRADEMARK OFFICE
CERTIFICATE OF CORRECTION

PATENT NO. : 4,775,624

DATED : October 4, 1988

INVENTOR(S) : Bang et al.

It is certified that error appears in the above-identified patent and that said Letters Patent is hereby corrected as shown below:

In column 18, line 25, please change "TAA" to -- TAA --.
                                          ' ' '        ' ' '
                                          ACT          ATT In column 22, line 55, please change "∿0" to -- 40 --.

In column 27, line 29, please change "Isolation of" to -- B. Isolation of --.

In column 29, line 13, please change 3'-GGAGTTCC-5' to -- 3'-GGAGCTCC-5' --.

In column 31, line 19, please change "110" to -- 101 --.

In column 32, line 50, please change "pMMTAΔBPV" to -- pMMTΔBPV --.

In column 43, line 31, please change "aspiratrr" to -- aspirator --.

In column 45, line 63, please change "whn" to -- when --

Signed and Sealed this

Eighth Day of January, 1991

Attest:

HARRY F. MANBECK, JR.

*Attesting Officer*   *Commissioner of Patents and Trademarks*